US011248055B2

(12) United States Patent
Pattyn et al.

(10) Patent No.: US 11,248,055 B2
(45) Date of Patent: Feb. 15, 2022

(54) POLYPEPTIDES INHIBITING CD40L

(71) Applicant: Ablynx N.V., Ghent-Zwijnaarde (BE)

(72) Inventors: Els Pattyn, Huise (BE); Ariëlla Van de Sompel, Oostakker (BE); Peter Meerts, Lokeren (BE); Marie-Ange Buyse, Merelbeke (BE); Maarten Dewilde, Aalst (BE); Gerald Beste, Ghent (BE); Jaromir Vlach, Westford, MA (US); Jonathan Hsu, Waltham, MA (US)

(73) Assignee: Ablynx N.V., Zwijnaarde (BE)

( * ) Notice: Subject to any disclaimer, the term of this patent is extended or adjusted under 35 U.S.C. 154(b) by 661 days.

(21) Appl. No.: 15/778,677

(22) PCT Filed: Nov. 28, 2016

(86) PCT No.: PCT/EP2016/079048
§ 371 (c)(1),
(2) Date: May 24, 2018

(87) PCT Pub. No.: WO2017/089618
PCT Pub. Date: Jun. 1, 2017

(65) Prior Publication Data
US 2018/0355050 A1  Dec. 13, 2018

Related U.S. Application Data

(60) Provisional application No. 62/345,967, filed on Jun. 6, 2016, provisional application No. 62/260,411, filed on Nov. 27, 2015.

(51) Int. Cl.
| | | |
|---|---|---|
| *C07K 16/28* | (2006.01) | |
| *A61K 39/395* | (2006.01) | |
| *C07K 16/18* | (2006.01) | |
| *A61K 39/00* | (2006.01) | |

(52) U.S. Cl.
CPC .......... *C07K 16/2875* (2013.01); *C07K 16/18* (2013.01); *A61K 2039/505* (2013.01); *C07K 2317/22* (2013.01); *C07K 2317/31* (2013.01); *C07K 2317/33* (2013.01); *C07K 2317/565* (2013.01); *C07K 2317/567* (2013.01); *C07K 2317/569* (2013.01); *C07K 2317/73* (2013.01); *C07K 2317/76* (2013.01); *C07K 2317/92* (2013.01); *C07K 2317/94* (2013.01); *C07K 2319/31* (2013.01)

(58) Field of Classification Search
None
See application file for complete search history.

(56) References Cited

U.S. PATENT DOCUMENTS

2011/0172400 A1* 7/2011 Grant .............. A61P 37/00
530/389.6

FOREIGN PATENT DOCUMENTS

| CL | 200100584 | 3/2001 |
|---|---|---|
| CL | 200700768 | 3/2007 |
| CL | 201400958 | 4/2014 |
| CL | 201800103 | 1/2018 |
| CL | 201800298 | 2/2018 |
| CN | 104245732 A | 12/2014 |
| JP | 2012-167112 A | 9/2012 |
| WO | WO 2001/068860 A1 | 9/2001 |
| WO | WO 2006/030220 A1 | 3/2006 |
| WO | 2006/122786 A2 | 11/2006 |
| WO | WO 2012/175400 A1 | 12/2012 |
| WO | WO 2013/024059 A2 | 2/2013 |
| WO | WO 2013/056068 A1 | 4/2013 |
| WO | WO 2015/044386 A1 | 4/2015 |
| WO | WO 2015/143209 A1 | 9/2015 |
| WO | WO 2017/011544 A1 | 1/2017 |
| WO | WO 2017/024146 A1 | 2/2017 |

OTHER PUBLICATIONS

Rudikoff et al., Proc Natl Acad Sci USA 79: 1979-1983 (1982). (Year: 1982).*
Colman, Research in Immunology 145: 33-36 (1994). (Year: 1994).*
Kussie et al., J. Immunol. 152: 146-152 (1994). (Year: 1994).*
Chen et al., EMBO J., 14:2784-2794 (1995). (Year: 1994).*
D'Angelo et al., Many Routes to an Antibody Heavy-Chain CDR3: Necessary, Yet Insufficient, for Specific Binding; Frontiers in Immunology vol. 9, Article 395 Mar. 2018; doi:10.3389/fimmu.2018. 00395. (Year: 2018).*
Piche-Nicholas et al., Changes in complemetarity-determining regions significantly alter IgG binding to the neonatal Fc receptor (FcRN) and pharmacokinetics; MABS 2018, vol. 10, No. 1, 81-94. (Year: 2018).*
Henry et al., Stability-Diversity Tradeoffs Impose Fundamental Constraints on Selection of Synthetic Human VH/VL Single-Domain Antibodies from In Vitro Display Libraries, Frontiers in Immunology, vol. 8, Article 1759, pp. 1-15, published: Dec. 12, 2017; doi: 10.3389/fimmu.2017.017959. (Year: 2017).*
Bondar et al., The role of CD40 receptor-ligand system in the development of diabetes mellitus and its complications. Diabetes Mellitus. Sep. 2011;14(3):21-25. Doi: 10.14341/2072-0351-6219.
Chen et al., Fusion protein linkers: property, design and functionality. Adv Drug Deliv Rev. Oct. 2013;65(10):1357-69. doi: 10.1016/j.addr.2012.09.039. Epub Sep. 29, 2012.
Cody et al., Specificity of human anti-variable heavy (VH) chain autoantibodies and impact on the design and clinical testing of a VH domain antibody antagonist of tumour necrosis factor-α receptor 1. Clin Exp Immunol. 2015;182(2): 139-148. doi:10.1111/cei.12680.
Frankel et al., Characterization of diphtheria fusion proteins targeted to the human interleukin-3 receptor. Protein Eng. Aug. 2000;13(8):575-81. doi: 10.1093/protein/13.8.575.

(Continued)

*Primary Examiner* — Phillip Gambel
(74) *Attorney, Agent, or Firm* — Wolf, Greenfield & Sacks, P.C.

(57) ABSTRACT

The present invention relates to immunoglobulins that specifically bind CD40L and more in particular to polypeptides, nucleic acids encoding such polypeptides; to methods for preparing such polypeptides; to compositions and in particular to pharmaceutical compositions that comprise such polypeptides, for prophylactic, therapeutic or diagnostic purposes. In particular, the immunoglobulins of the present invention inhibit the activity of CD40L and are safe.

Figure 1:
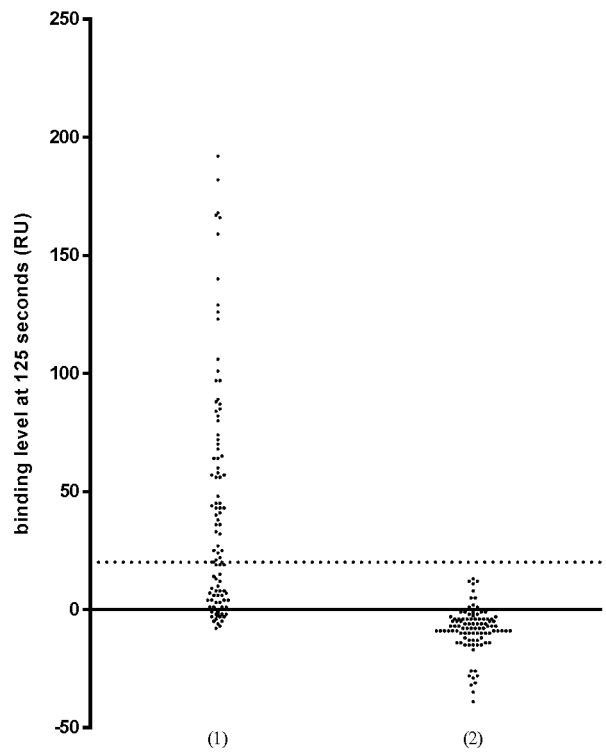

13 Claims, 4 Drawing Sheets
Specification includes a Sequence Listing.

(56) References Cited

OTHER PUBLICATIONS

Klein et al., Somatic mutations of the immunoglobulin framework are generally required for broad and potent HIV-1 neutralization. Cell. Mar. 28, 2013;153(1):126-38. doi:10.1016/j.cell.2013.03.018.
Maeda et al., Engineering of functional chimeric protein G-Vargula luciferase. Anal Biochem. Jul. 1, 1997;249(2):147-52. doi: 10.1006/abio.1997.2181.
Safdari et al., Antibody humanization methods—a review and update. Biotechnol Genet Eng Rev. 2013;29:175-86. doi: 10.1080/02648725.2013.801235. Epub Aug. 2, 2013.
Shock et al., CDP7657, an anti-CD40L antibody lacking an Fc domain, inhibits CD40L-dependent immune responses without thrombotic complications: an in vivo study. Arthritis Res Ther. Sep. 3, 2015;17:234. doi: 10.1186/s13075-015-0757-4.
Teplyakov et al., Antibody modeling assessment II. Structures and models. Proteins. Aug. 2014;82(8):1563-82. doi: 10.1002/prot.24554. Epub Mar. 31, 2014.
Xie et al, Engineering of a novel anti-CD40L domain antibody for treatment of autoimmune diseases. J Immunol. May 1, 2014;192(9):4083-92. doi: 10.4049/jimmunol. 1303239. Epub Mar. 26, 2014.
Search Report for Application No. CL 201801400, dated Feb. 28, 2020.
International Search Report and Written Opinion for Application No. PCT/EP2016/079048, dated May 11, 2017.
International Preliminary Report on Patentability for Application No. PCT/EP2016/079048, dated Jun. 7, 2018.
Korniluk et al., Multifunctional CD40L: pro—and anti-neoplastic activity. Tumour Biol. Oct. 2014;35(10):9447-57. doi: 10.1007/s13277-014-2407-x. Epub Aug. 13, 2014.
Pakula et al., Genetic analysis of protein stability and function. Annu Rev Genet. 1989;23:289-310. doi: 10.1146/annurev.ge.23.120189.001445.
Seyama et al., Mutations of the CD40 ligand gene and its effect on CD40 ligand expression in patients with X-linked hyper IgM syndrome. Blood. Oct. 1, 1998;92(7):2421-34.
Shen et al., Single variable domain-IgG fusion. A novel recombinant approach to Fc domain-containing bispecific antibodies. J Biol Chem. Apr. 21, 2006;281(16):10706-14. doi: 10.1074/jbc.M513415200. Epub Feb. 15, 2006.

\* cited by examiner

POLYPEPTIDES INHIBITING CD40L

RELATED APPLICATIONS

This Application is a national stage filing under 35 U.S.C. 371 of International Patent Application Serial No. PCT/EP2016/079048, filed Nov. 28, 2016, which claims the benefit under 35 USC 119(e) of U.S. Provisional Application Ser. No. 62/345,967, filed Jun. 6, 2016, and U.S. Provisional Application Ser. No. 62/260,411, filed Nov. 27, 2015, the contents of each of which is incorporated herein by reference in its entirety.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on May 24, 2018, is named A084870189US02-SEQ-JRV, and is 50,333 bytes in size.

1 FIELD OF THE INVENTION

The present invention relates to immunoglobulins that bind CD40L and more in particular to polypeptides, that comprise or essentially consist of one or more such immunoglobulins (also referred to herein as "immunoglobulin(s) of the invention", and "polypeptides of the invention", respectively).

The invention also relates to nucleic acids encoding such polypeptides (also referred to herein as "nucleic acid(s) of the invention"; to methods for preparing such polypeptides; to host cells expressing or capable of expressing such polypeptides; to compositions, and in particular to pharmaceutical compositions, that comprise such polypeptides, nucleic acids and/or host cells; and to uses of polypeptides, nucleic acids, host cells and/or compositions, in particular for prophylactic and/or therapeutic purposes, such as the prophylactic and/or therapeutic purposes mentioned herein.

Other aspects, embodiments, advantages and applications of the invention will become clear from the further description herein.

2 BACKGROUND OF THE INVENTION

CD40/CD40 ligand (CD40L, CD154) interactions have been shown to play a crucial role in the initiation (Grewal & Flavell, 1998 Annu. Rev. Immunol. 16:111-135; Yang & Wilson, 1996 Science 273:1862-1864) and maintenance (Grewal et al., 1996 Science 273:1864-1867; Buhlmann et al., 1999 J. Immunol. 162:4373-4376) of B- and T-cell responses. CD40 costimulatory molecule is expressed on the surface of a variety of antigen-presenting cells (APC) including dendritic cells (DCs), B-lymphocytes, macrophages and subsets of $CD34^+$ cell progenitors either constitutively or following in vitro activation (McLellan et al., 1996 Eur. J. Immunol. 26:1204-1210; Rondelli et al., 1999 Blood 94:2293-2300). CD40L is expressed on the surface of $CD4^+$ and some $CD8^+$ T-lymphocytes following T-cell receptor-mediated stimulation. The interaction between CD40 and CD40L leads to bidirectional signals affecting both APC and T-cell function. On one side, CD40L dependent stimulation of CD40 induces DC and macrophages to express T-cell costimulatory molecules such as CD80 and CD86, and to produce immunostimulatory cytokines such as IL-12, thus augmenting their ability to initiate both helper and cytotoxic T-cell responses (Kennedy et al., 1994 Eur. J. Immunol. 24:116-123; Caux et al., 1994 J. Exp. Med. 180:1263-1272). On the other side, CD40 dependent stimulation of CD40L delivers a costimulatory signal (Brenner et al., 1997 FEBS Letters 417:301-306) contributing to T-cell activation (Koppenhoefer et al., 1997 FEBS Letters 414: 444-448; Blotta et al., 1996 J. Immunol. 156:3133-3140). Evidence from animal models and humans support an essential role of CD40-CD40L interactions in the generation of pathogenic autoantibodies and tissue injury in a variety of autoimmune diseases, such as lupus nephritis, systemic lupus erythematosus (SLE), idiopathic thrombocytopenic purpura (ITP) and amyotrophic lateral sclerosis (ALS), also known as Lou Gehrig's disease and Charcot disease. These findings prompted the development of antibodies disrupting the CD40-CD40L interaction.

A humanized monoclonal antibody (mAb) directed against human CD40L (hu5C8 or ruplizumab, Biogen) has been shown to induce long term graft survival in most recipients in a non-human primate model of kidney transplantation from MHC (major histocompatibility complex) mismatched donors (Kirk et al., 1999 Nat. Med. 5:686-693). The same antibody has also been tested in a phase II trial in lupus nephritis. However, the study had to be terminated prematurely because of thromboembolic events (TE), including myocardial infarctions (Kawai et al., 2000 Nat. Med. 6:114).

The humanized anti-CD40L antibody toralizumab (IDEC-131, hu24-31) of IgG1 isotype is derived from the murine anti-CD40L hybridoma 24-31. Similar to ruplizumab, the multiple phase I and phase II trial which were planned for toralizumab were also stopped due to risk of thromboembolic events in human patients.

A third anti-CD40L antibody developed was AB1793, which is a human IgG1 derived from HUMAB® mice (Medarex Inc.). In this case, TE were already observed in rhesus and cynomolgus renal transplant models, because of which further development of AB1793 was stopped.

The thromboembolic events can be developed with antibodies against different epitopes, in various disease backgrounds and involved both venous and arterial territories in diverse sites including myocardium, pulmonary artery and peripheral veins. The exact mechanism underlying the anti-CD40L-induced TE, however, remains to be elucidated. The principal hypotheses are:
(i) Cross-linking of CD40L on platelets due to the bivalent nature of the IgG monoclonal antibody;
(ii) Interaction of the anti-CD40L antibody with platelet Fc receptors, thus promoting platelet aggregation and thrombosis.

In addition, immune responses to therapeutic protein products such as pre-existing antibodies (PEAs) and/or anti-drug antibodies (ADA), may pose problems for both patient safety and product efficacy. These immunologically based adverse events include anaphylaxis, cytokine release syndrome, "infusion reactions" and Non-Acute Reactions (delayed onset of fever, rash, arthralgia, myalgia, hematuria, proteinuria, serositis, central nervous system complications, and hemolytic anemia) as well as cross-reactive neutralization of endogenous proteins mediating critical functions. Unwanted immune responses to therapeutic protein products may also neutralize their biological activities and result in adverse events not only by inhibiting the efficacy of the therapeutic protein product, but also by cross-reacting to an endogenous protein counterpart, leading to loss of its physiological function. The safety consequences of immunogenicity may vary widely and are often unpredictable in patients administered therapeutic protein products. PEA and ADA can have severe consequences if cross-reacting to and inhibiting a non-redundant endogenous counterpart of the therapeutic protein product or related proteins (Macdougall et al., 2012 Kidney Int. 2012 81:727-32; Seidl et al., 2012 Pharm Res 29:1454-1467).

WO2013/056068 relates to dimeric fusion proteins composed of a modified Fc fragment of IgG1 linked to the C-terminus of a domain antibody (dAb) directed against CD40L. WO2013/056068 did not report on PEA, but reports that in monkeys ADAs were developed against the protein, resulting in a fast clearance (low plasma exposure and low serum $T_{1/2}$).

No reports on immunoglobulin single variable domain antibodies sufficiently effective have transpired. Biogen and UCB are currently collaborating to re-engineer a pre-existing anti-CD40L antibody as a Fab'-PEG molecule (CDP7657) attempting to overcome the TE events seen with hu5C8. In order to prolong the half-life, the Fab' moiety was coupled to polyethylene glycol (PEG). PEG has a wide variety of applications, from industrial manufacturing to medicine, because of which it is ubiquitously used. A recent finding demonstrated a 22-25% occurrence of anti-PEG antibodies in healthy blood donors. This development of anti-PEG antibodies, which may limit efficacy in some patients, is contrary to the general assumption that PEG is non-immunogenic. Hence, PEGylated therapeutic agents have potential implications for clinical use, especially in an immune-compromised disease setting. Moreover, it was reported that PEGylation of the Fab' molecule decreased its activity by 4-5 fold (US2010/0104573). Xie et al. describe the necessity of Fc formatting, which includes making the molecule bivalent, to improve potency (Xie et al., 2014 J. Immunol. 192:4083-4092).

Accordingly, there is a need for safe and efficacious anti-CD40L medicaments.

The present inventors hypothesized that a monovalent entity targeting CD40L without a functional Fc domain may represent a modality that would inhibit the CD40-CD40L T-cell costimulation without inducing adverse events through platelet aggregation and/or activation.

3 SUMMARY OF THE INVENTION

The present invention set out to provide polypeptides against CD40L with improved prophylactic, therapeutic and/or pharmacological properties, in addition to other advantageous properties (such as, for example, improved ease of preparation, good stability, and/or reduced costs of goods), compared to the prior art amino acid sequences and antibodies.

Based on unconventional screening, characterization and combinatory strategies, the present inventors unexpectedly observed that stand-in immunoglobulin single variable domains (ISVDs) exceptionally performed in in vivo efficacy studies and in vitro safety experiments.

Moreover, the present inventors were able to re-engineer the ISVDs to not only outperform the benchmark CDP7657 but to also retain this performance upon half-life extension. On the other hand, the ISVDs of the invention were also demonstrated to be significantly safer than the prior art antibodies.

Accordingly, the present invention relates to polypeptides that are directed against/and or that may specifically bind (as defined herein) to CD40L.

In particular, the present invention relates to a polypeptide comprising at least one immunoglobulin single variable domain (ISVD) specifically binding CD40L, wherein binding to CD40L modulates an activity of CD40L.

The present invention also relates to a polypeptide as described herein, wherein said ISVD specifically binding CD40L essentially consists of 4 framework regions (FR1 to FR4, respectively) and 3 complementarity determining regions (CDR1 to CDR3 respectively), in which
  (i) CDR1 is chosen from the group consisting of SEQ ID NOs: 33, 61, 40 and 68; and amino acid sequences that have 1, 2 or 3 amino acid difference(s) with SEQ ID NOs: 33, 40 61 or 68;
  (ii) CDR2 is chosen from the group consisting of SEQ ID NOs: 35, 63, 42 and 70; and amino acid sequences that have 1, 2 or 3 amino acid difference(s) with SEQ ID NOs: 35, 42, 63 or 70; and
  (iii) CDR3 is chosen from the group consisting of SEQ ID NO: 37, 65, 44 and 72; and amino acid sequences that have 1, 2, 3 or 4 amino acid difference(s) with SEQ ID NOs: 37, 65, 44 or 72;

The present invention also relates to a polypeptide as described herein, in which CDR1 is chosen from the group consisting of
  (a) SEQ ID NO: 61 and
  (b) amino acid sequences that have 1, 2 or 3 amino acid difference(s) with SEQ ID NO: 61, wherein
    at position 1 the G has been changed into E or R;
    at position 2 the R has been changed into H or G;
    at position 3 the T has been changed into I, A, S or P;
    at position 4 the P has been changed into 5;
    at position 5 the L has been changed into P;
    at position 6 the N has been changed into S, D or I;
    at position 7 the Y has been changed into H;
    at position 8 the H has been changed into N;
    at position 9 the M has been changed into K, T or V; and/or
    at position 10 the A has been changed into G, S or T.

The present invention also relates to a polypeptide as described herein, in which CDR2 is chosen from the group consisting of
  (a) SEQ ID NO: 63; and
  (b) amino acid sequences that have 1, 2 or 3 amino acid difference(s) with SEQ ID NO: 63, wherein
    at position 1 the A has been changed into G;
    at position 2 the I has been changed into V;
    at position 4 the S has been changed into N, R or G;
    at position 6 the L has been changed into I;
    at position 7 the G has been changed into S or D;
    at position 8 the S has been changed into G, I or F; and/or
    at position 9 the T has been changed into P or S.

The present invention also relates to a polypeptide as described herein, in which CDR3 is chosen from the group consisting of
  (a) SEQ ID NO: 65; and
  (b) amino acid sequences that have 1, 2, 3 or 4 amino acid difference(s) with SEQ ID NO: 65, wherein
    at position 1 the R has been changed into Q or L;
    at position 2 the E has been changed into D or K;
    at position 3 the T has been changed into S, M, A or K;
    at position 4 the T has been changed into I, S, A or R;
    at position 5 the H has been changed into Y or N;
    at position 6 the Y has been changed into I, H or N;
    at position 7 the S has been changed into T, G, N or I;
    at position 8 the T has been changed into I or A;
    at position 9 the S has been changed into N or R;
    at position 10 the D has been changed into A;
    at position 11 the R has been changed into S or G;

at position 13 the N has been changed into D, Y or 5;
at position 14 the E has been changed into V, A, D or N;
at position 15 the M has been changed into I, V, K or T;
at position 16 the R has been changed into K, S, W, M, G or T;
at position 17 the H has been changed into N, L, Q, R or D;
at position 19 the D has been changed into N; and/or
at position 20 the Y has been changed into H, F or N.

The present invention also relates to a polypeptide as described herein, in which
CDR1 is SEQ ID NO: 33, CDR2 is SEQ ID NO: 35 and CDR3 is SEQ ID NO: 37; or
CDR1 is SEQ ID NO: 61, CDR2 is SEQ ID NO: 63 and CDR3 is SEQ ID NO: 65.

The present invention also relates to a polypeptide as described herein, in which said ISVD is SEQ ID NO: 8 or SEQ ID NO: 6.

The present invention also relates to a polypeptide as described herein, in which CDR1 is chosen from the group consisting of
(a) SEQ ID NO: 40; and
(b) amino acid sequences that have 1, 2 or 3 amino acid difference(s) with SEQ ID NO: 40, wherein
at position 3 the T has been changed into S, N, A or I;
at position 4 the L has been changed into Q, S, M or G;
at position 8 the A has been changed into N or V;
at position 9 the I has been changed into L or V; and/or
at position 10 the G has been changed into A.

The present invention also relates to a polypeptide as described herein, 8, in which CDR2 is chosen from the group consisting of
(a) SEQ ID NO: 42; and
(b) amino acid sequences that have 1, 2 or 3 amino acid difference(s) with SEQ ID NO: 42, wherein
at position 2 the I has been changed into V;
at position 3 the S has been changed into G;
at position 5 the E has been changed into G;
at position 6 the G has been changed into 5;
at position 7 the S has been changed into G, N, T or I;
at position 8 the T has been changed into A, P, I or 5; and/or
at position 9 the S has been changed into I, R or G.

The present invention also relates to a polypeptide as described herein, in which CDR3 is chosen from the group consisting of
(a) SEQ ID NO: 44; and
(b) amino acid sequences that have 1, 2, 3 or 4 amino acid difference(s) with SEQ ID NO: 44, wherein
at position 4 the R has been changed into 5;
at position 7 the L has been changed into F, M or W;
at position 8 the G has been changed into D, A or 5;
at position 9 the S has been changed into G, N or R;
at position 10 the S has been changed into G, N, T or R;
at position 12 the D has been changed into G, N, E or V;
at position 13 the T has been changed into N or A;
at position 14 the Q has been changed into H, K, L or R;
at position 15 the S has been changed into P or T;
at position 16 the H has been changed into N or Y;
at position 17 the Q has been changed into L, R or H;
at position 18 the Y has been changed into F;
at position 19 the D has been changed into G; and/or
at position 20 the Y has been changed into F or N.

The present invention also relates to a polypeptide as described herein, in which CDR1 is SEQ ID NO: 40, CDR2 is SEQ ID NO: 42 and CDR3 is SEQ ID NO: 44.

The present invention also relates to a polypeptide as described herein, in which said ISVD is SEQ ID NO: 7 or SEQ ID NO: 3.

The present invention also relates to a polypeptide as described herein, wherein said polypeptide binds to CD40L with a KD between $1E^{-07}$ M and $1E^{-13}$ M, such as between $1E^{-07}$ M and $1E^{-12}$ M, preferably at most $1E^{-07}$ M, preferably lower than $1E^{-08}$ M or $1E^{-09}$ M, or even lower than $1E^{-10}$ M, such as $5E^{-11}$ M, $4E^{-11}$ M, $3E^{-11}$ M, $2E^{-11}$ M, $1.7E^{-11}$ M, $1E^{-11}$, or even $5E^{-12}$ M, $4E^{-12}$ M, $3E^{-12}$ M, $1E^{-12}$ M, for instance as determined by a KinExA.

The present invention also relates to a polypeptide as described herein, wherein said polypeptide binds to CD40L with an $IC_{50}$ between $1E^{-07}$ M and $1E^{-12}$ M, such as between $1E^{-08}$ M and $1E^{-11}$ M, for instance as determined by a B-cell proliferation assay or as determined by a B-cell signaling assay.

The present invention also relates to a polypeptide as described herein, wherein said polypeptide binds to CD40L with an $IC_{50}$ of at most $1E^{-07}$ M, preferably $1E^{-08}$ M, $1E^{-09}$ M, or $5E^{-10}$ M, $4E^{-10}$ M, $3E^{-10}$ M, $2E^{-10}$ M, such as $1E^{-10}$ M.

The present invention also relates to a polypeptide as described herein, wherein said polypeptide binds to CD40L with an off-rate of less than $5E^{-04}$ ($s^{-1}$), for instance as determined by SPR.

The present invention also relates to a polypeptide as described herein, wherein said CD40L, is preferably human CD40L, preferably SEQ ID NO: 18.

The present invention also relates to a polypeptide as described herein, wherein said polypeptide antagonizes an activity of CD40L.

The present invention also relates to a polypeptide as described herein, wherein said polypeptide blocks the binding of CD40L to CD40 of at least 20%, such as at least 30%, 40%, 50%, 60%, 70%, 80%, 90%, 95% or even more, for instance as determined by ligand competition, B-cell activation assay, ALPHASCREEN®, or competitive binding assays, such as competition ELISA or competition FACS).

The present invention also relates to a polypeptide as described herein, wherein said polypeptide antagonizes CD40 mediated induction of T-cell costimulatory molecules, such as CD80 and CD86 and/or immunostimulatory molecules such as IL12.

The present invention also relates to a polypeptide as described herein, wherein said polypeptide inhibits B-cell activation.

The present invention also relates to a polypeptide as described herein, wherein said polypeptide does not substantially induce JNK phosphorylation in Jurkat T cells or does not substantially induce IFNγ secretion by Jurkat T cells co-stimulated with anti-CD3 antibody.

The present invention also relates to a polypeptide as described herein, wherein said polypeptide inhibits B-cell activation, for instance as determined by a TT IgG assay.

The present invention also relates to a polypeptide as described herein, further comprising an ISVD binding serum albumin (ALB-NANOBODY®).

The present invention also relates to a polypeptide as described herein, wherein said ISVD binding serum albumin essentially consists of 4 framework regions (FR1 to FR4, respectively) and 3 complementarity determining regions (CDR1 to CDR3 respectively), in which CDR1 is SEQ ID NO: 74, CDR2 is SEQ ID NO: 75 CDR1 is SEQ ID NO: 76.

The present invention also relates to a polypeptide as described herein, wherein said ISVD binding serum albumin is chosen from the group consisting of ALB135 (SEQ ID NO: 15), ALB129 (SEQ ID NO: 13), ALB8 (SEQ ID NO: 11), ALB23 (SEQ ID NO: 12), and ALB132 (SEQ ID NO: 14).

The present invention also relates to a polypeptide as described herein, wherein said ISVD that specifically binds to CD40L and said ISVD binding serum albumin are directly linked to each other or are linked via a linker.

The present invention also relates to a polypeptide as described herein, wherein said linker is chosen from the group consisting of SEQ ID NOs: 18-29 and 77, preferably SEQ ID NO: 21.

The present invention also relates to a polypeptide as described herein, further comprising a C-terminal extension.

The present invention also relates to a polypeptide as described herein, wherein said C-terminal extension is a C-terminal extension $(X)n$, in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I).

The present invention also relates to a polypeptide as described herein, wherein said polypeptide further comprises an ISVD binding serum albumin as described herein, a linker as described herein, and a C-terminal extension as described herein.

The present invention also relates to a polypeptide as described herein, wherein said polypeptide has at least 80%, 90%, 95% or 100% sequence identity with C010003318 (SEQ ID NO: 9) or C010003313 (SEQ ID NO: 78).

The present invention also relates to a polypeptide as described herein, wherein said polypeptide does not substantially induce activation of primary endothelial cells.

The present invention also relates to a polypeptide as described herein, wherein said polypeptide does not substantially induce platelet activation or platelet aggregation, for instance as determined by a platelet activation assay or platelet aggregation assay.

The present invention also relates to a method of treating prevention of diseases or disorders in an individual, for instance in which inappropriate activation of a CD40L/CD40-mediated pathway is involved, the method comprising administering the polypeptide of the invention to said individual in an amount effective to treat or prevent a symptom of said disease or disorder.

The present invention also relates to a method as described herein, wherein said diseases or disorders comprises Systemic Lupus Erythematosus (SLE), Lupus Nephritis, Immune Thrombocytopenic Purpura (ITP), transplant rejection, Crohn's Disease, Sjögren's Syndrome, Inflammatory Bowel Disease (IBD), colitis, asthma/allergy, atherosclerosis, Myasthenia Gravis, Multiple Sclerosis, Psoriasis, Rheumatoid Arthritis, Ankylosing Spondylitis, Coronary Heart Disease, Type 1 Diabetes and immune response to recombinant drug products, e.g., factor VII in hemophilia.

The present invention also relates to a polypeptide as described herein for use as a medicament.

The present invention also relates to a polypeptide as described herein for use in treating or preventing a symptom of an autoimmune disease, Systemic Lupus Erythematosus (SLE), Lupus Nephritis, Immune Thrombocytopenic Purpura (ITP), transplant rejection, Crohn's Disease, Sjögren's Syndrome, Inflammatory Bowel Disease (IBD), colitis, asthma/allergy, atherosclerosis, Myasthenia Gravis, Multiple Sclerosis, Psoriasis, Rheumatoid Arthritis, Ankylosing Spondylitis, Coronary Heart Disease, Type 1 Diabetes and immune response to recombinant drug products, e.g., factor VII in hemophilia.

The present invention also relates to a polypeptide as described herein, wherein said polypeptide cross-blocks the binding to CD40L of at least one of the polypeptides 46603 (SEQ ID NO: 6), 28602 (SEQ ID NO: 3) C010003290 (SEQ ID NO: 8) and C010003318 (SEQ ID NO: 9) and/or is cross-blocked from binding to CD40L by at least one of the polypeptides 46603 (SEQ ID NO: 6), 28602 (SEQ ID NO: 3) C010003290 (SEQ ID NO: 8) and C010003318 (SEQ ID NO: 9).

The present invention also relates to a polypeptide cross-blocking binding to CD40L by at least one of 46603 (SEQ ID NO: 6), 28602 (SEQ ID NO: 3) C010003290 (SEQ ID NO: 8) and C010003318 (SEQ ID NO: 9) and/or is cross-blocked from binding to CD40L by at least one of 46603 (SEQ ID NO: 6), 28602 (SEQ ID NO: 3) C010003290 (SEQ ID NO: 8) and C010003318 (SEQ ID NO: 9), wherein said polypeptide comprises at least one VH, VL, dAb, immunoglobulin single variable domain (ISVD) specifically binding to CD40L, wherein binding to CD40L modulates an activity of CD40L.

4 FIGURE LEGENDS

FIG. 1: Plot showing data points obtained in Example 6.9.3 when 96 serum samples were tested for binding a representative NANOBODY® with an S112K mutation (Reference A+S 112K+C-terminal alanine, indicated as (2) in FIG. 1), compared to a reference NANOBODY® without an S112K mutation (Reference A, SEQ ID NO: 16, indicated as (1) in FIG. 1).

Figure 2:
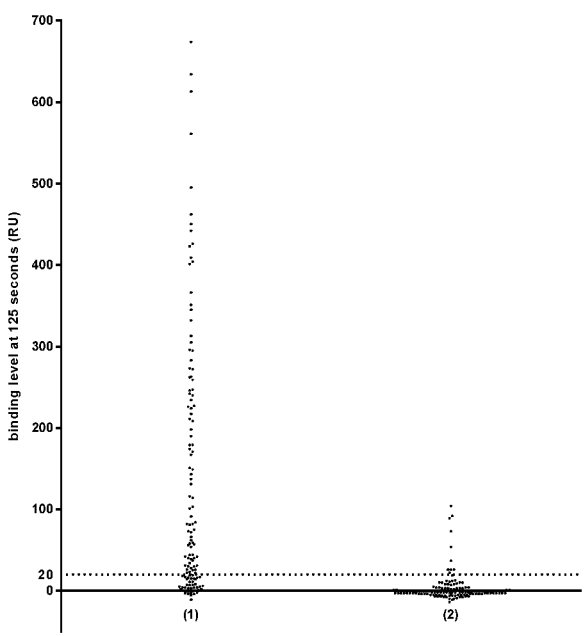
Figure 3:
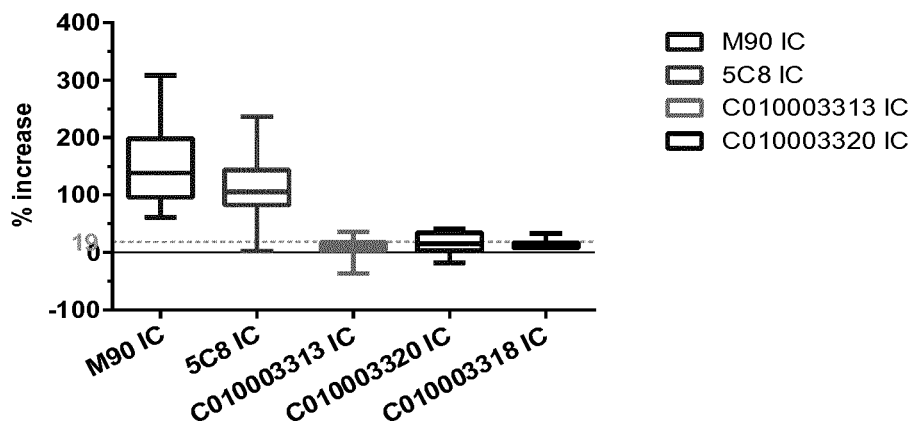
Figure 4:
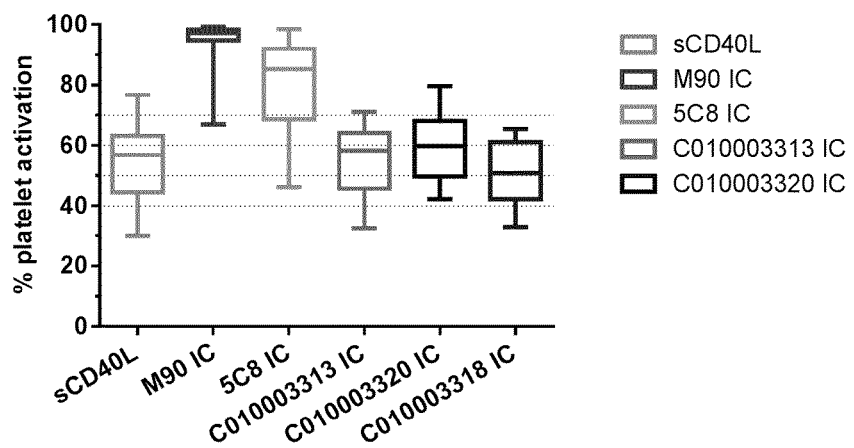
Figure 5:
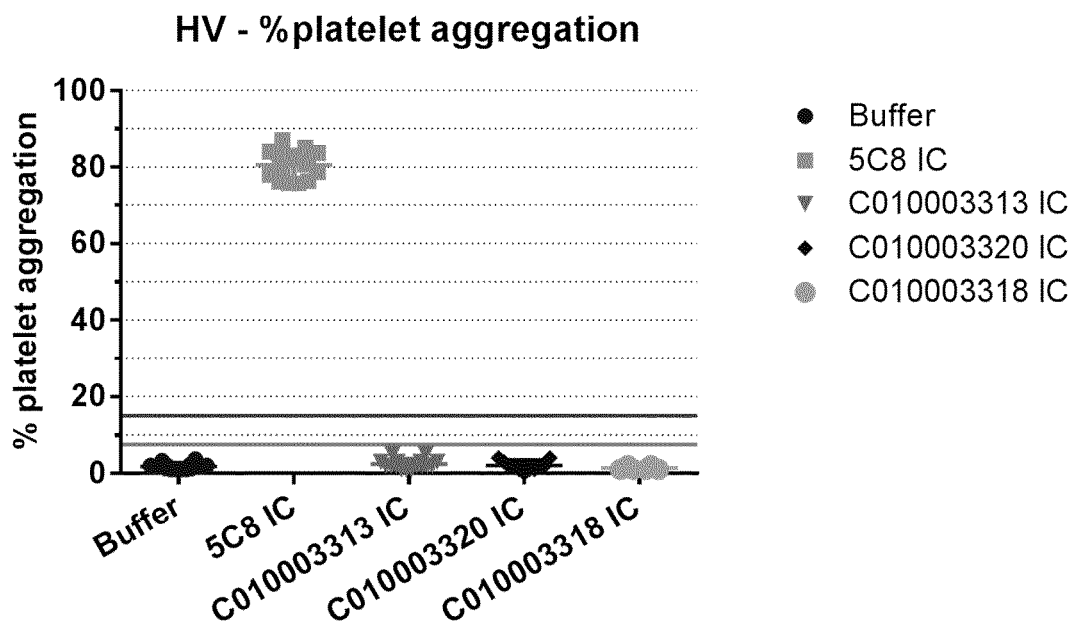
Figure 6:
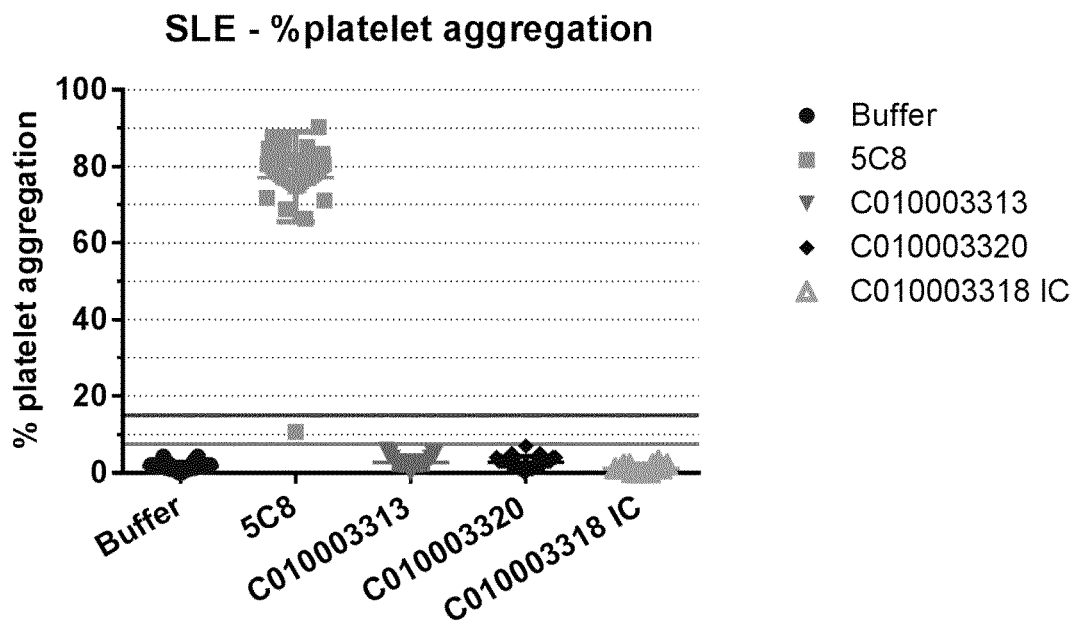
Figure 7:
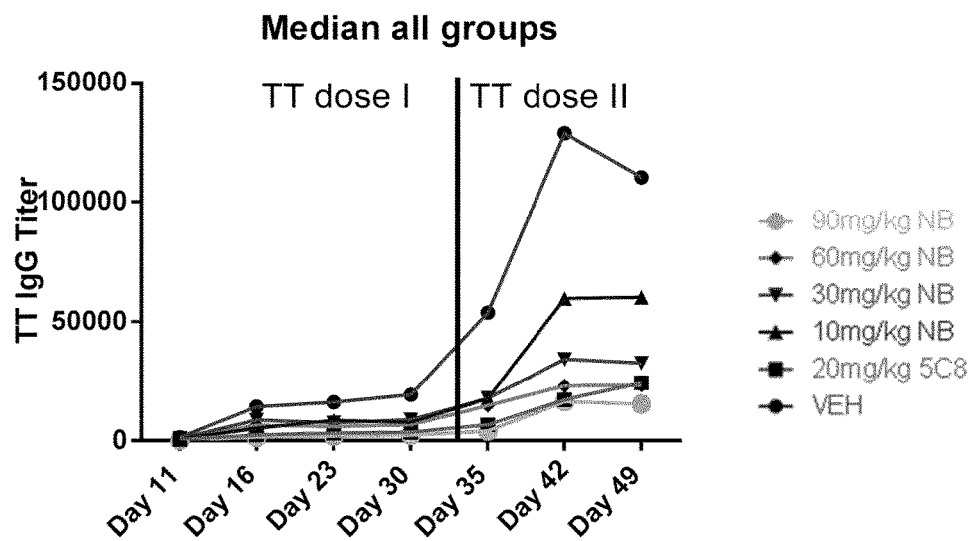
Figure 8:
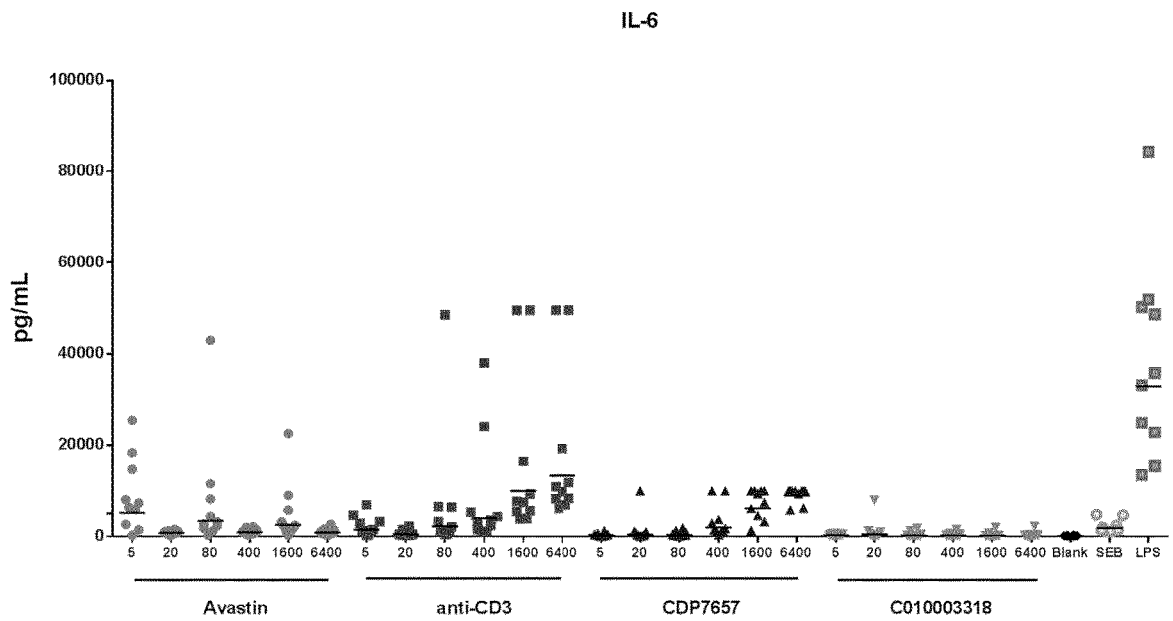

FIG. 2 Plot showing data points obtained in Example 6.9.3 when 129 serum samples were tested for binding a representative NANOBODY® with an V89T mutation (Reference A+L11V+V89T+C-terminal alanine, indicated as (2) in FIG. 2), compared to a reference NANOBODY® without an V89T mutation (Reference A, SEQ ID NO: 16, indicated as (1) in FIG. 2);

FIG. 3 Platelet activation data HV
FIG. 4 Platelet activation data SLE
FIG. 5 Platelet aggregation data HV
FIG. 6 Platelet aggregation data SLE
FIG. 7 Anti-CD40L NANOBODIES® impair the TT-IgG response
FIG. 8 IL-6 induction upon human PBMC stimulation with the different compounds at the indicated concentrations.

5 DETAILED DESCRIPTION

There remains a need for safe and efficacious anti-CD40L medicaments. These medicaments should comply with various and frequently opposing requirements. The format should be broadly applicable. In particular, the format should preferably be useful in a broad range of patients and preferably also against a broad range of CD40L mediated disorders. The format should preferably be safe and not induce any thromboembolic events. In addition, the format should preferably be patient friendly. For instance, the format should have an extended half-life, such that the format is not removed instantaneous upon administration by renal clearance. However, extending the half-life should preferably not introduce off-target activity and side effects, induce TEs or limit efficacy.

The present invention realizes at least one of these requirements.

Based on unconventional screening, characterization and combinatory strategies, the present inventors surprisingly observed that stand-in immunoglobulin single variable domains (ISVDs) performed exceptionally in in vivo efficacy studies and in vitro safety experiments.

Moreover, the present inventors were able to re-engineer the ISVDs to not only outperform the benchmark CDP7657 but to also retain this performance upon half-life extension. On the other hand, the ISVDs of the invention were also demonstrated to be significantly safer than the prior art antibodies.

The present invention provides polypeptides antagonizing CD40L with improved prophylactic, therapeutic and/or pharmacological properties, including a safer profile, compared to the prior art amino acid sequences and antibodies.

Accordingly, the present invention relates to polypeptides that are directed against/and or that may specifically bind (as defined herein) to CD40L, and modulate the activity thereof, in particular a polypeptide comprising at least one immunoglobulin single variable domain (ISVD) specifically binding CD40L, wherein binding to CD40L modulates an activity of CD40L.

Unless indicated or defined otherwise, all terms used have their usual meaning in the art, which will be clear to the skilled person. Reference is for example made to the standard handbooks, such as Sambrook et al. (Molecular Cloning: A Laboratory Manual (2nd. Ed.) Vols. 1-3, Cold Spring Harbor Laboratory Press, 1989), F. Ausubel et al. (Current protocols in molecular biology, Green Publishing and Wiley Interscience, New York, 1987), Lewin (Genes II, John Wiley & Sons, New York, N.Y., 1985), Old et al. (Principles of Gene Manipulation: An Introduction to Genetic Engineering (2nd edition) University of California Press, Berkeley, Calif., 1981); Roitt et al. (Immunology (6th. Ed.) Mosby/Elsevier, Edinburgh, 2001), Roitt et al. (Roitt's Essential Immunology ($10^{th}$ Ed.) Blackwell Publishing, U K, 2001), and Janeway et al. (Immunobiology (6th Ed.) Garland Science Publishing/Churchill Livingstone, New York, 2005), as well as to the general background art cited herein.

Unless indicated otherwise, all methods, steps, techniques and manipulations that are not specifically described in detail can be performed and have been performed in a manner known per se, as will be clear to the skilled person. Reference is for example again made to the standard handbooks and the general background art mentioned herein and to the further references cited therein; as well as to for example the following reviews Presta (Adv. Drug Deliv. Rev. 58 (5-6): 640-56, 2006), Levin and Weiss (Mol. Biosyst. 2(1): 49-57, 2006), Irving et al. (J. Immunol. Methods 248(1-2): 31-45, 2001), Schmitz et al. (Placenta 21 Suppl. A: S106-12, 2000), Gonzales et al. (Tumour Biol. 26(1): 31-43, 2005), which describe techniques for protein engineering, such as affinity maturation and other techniques for improving the specificity and other desired properties of proteins such as immunoglobulins.

It must be noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

The term "and/or" wherever used herein includes the meaning of "and", "or" and "all or any other combination of the elements connected by said term".

The term "about" or "approximately" as used herein means within 20%, preferably within 15%, more preferably within 10%, and most preferably within 5% of a given value or range.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having".

The term "sequence" as used herein (for example in terms like "immunoglobulin sequence", "antibody sequence", "variable domain sequence", "$V_{HH}$ sequence" or "protein sequence"), should generally be understood to include both the relevant amino acid sequence as well as nucleic acids or nucleotide sequences encoding the same, unless the context requires a more limited interpretation.

Amino acid residues will be indicated according to the standard three-letter or one-letter amino acid code. Reference is made to Table A-2 on page 48 of WO 08/020079.

A nucleic acid or amino acid is considered to be "(in) (essentially) isolated (form)"—for example, compared to the reaction medium or cultivation medium from which it has been obtained—when it has been separated from at least one other component with which it is usually associated in said source or medium, such as another nucleic acid, another protein/polypeptide, another biological component or macromolecule or at least one contaminant, impurity or minor component. In particular, a nucleic acid or amino acid is considered "(essentially) isolated" when it has been purified at least 2-fold, in particular at least 10-fold, more in particular at least 100-fold, and up to 1000-fold or more. A nucleic acid or amino acid that is "in (essentially) isolated form" is preferably essentially homogeneous, as determined using a suitable technique, such as a suitable chromatographical technique, such as polyacrylamide-gel electrophoresis.

When a nucleotide sequence or amino acid sequence is said to "comprise" another nucleotide sequence or amino acid sequence, respectively, or to "essentially consist of" another nucleotide sequence or amino acid sequence, this may mean that the latter nucleotide sequence or amino acid sequence has been incorporated into the first mentioned nucleotide sequence or amino acid sequence, respectively, but more usually this generally means that the first mentioned nucleotide sequence or amino acid sequence comprises within its sequence a stretch of nucleotides or amino acid residues, respectively, that has the same nucleotide sequence or amino acid sequence, respectively, as the latter sequence, irrespective of how the first mentioned sequence has actually been generated or obtained (which may for example be by any suitable method described herein). By means of a non-limiting example, when a polypeptide of the invention is said to comprise an immunoglobulin single variable domain, this may mean that said immunoglobulin single variable domain sequence has been incorporated into the sequence of the polypeptide of the invention, but more usually this generally means that the polypeptide of the invention contains within its sequence the sequence of the immunoglobulin single variable domains irrespective of how said polypeptide of the invention has been generated or obtained. Also, when a nucleic acid or nucleotide sequence is said to comprise another nucleotide sequence, the first mentioned nucleic acid or nucleotide sequence is preferably such that, when it is expressed into an expression product (e.g. a polypeptide), the amino acid sequence encoded by the latter nucleotide sequence forms part of said expression product (in other words, that the latter nucleotide sequence is in the same reading frame as the first mentioned, larger nucleic acid or nucleotide sequence).

By "essentially consist of" is meant that the immunoglobulin single variable domain used in the method of the invention either is exactly the same as the polypeptide of the invention or corresponds to the polypeptide of the invention which has a limited number of amino acid residues, such as 1-20 amino acid residues, for example 1-10 amino acid residues and preferably 1-6 amino acid residues, such as 1, 2, 3, 4, 5 or 6 amino acid residues, added at the amino terminal end, at the carboxy terminal end, or at both the amino terminal end and the carboxy terminal end of the immunoglobulin single variable domain.

For the purposes of comparing two or more nucleotide sequences, the percentage of "sequence identity" between a first nucleotide sequence and a second nucleotide sequence may be calculated by dividing [the number of nucleotides in the first nucleotide sequence that are identical to the nucleotides at the corresponding positions in the second nucleotide sequence] by [the total number of nucleotides in the first nucleotide sequence] and multiplying by [100%], in which each deletion, insertion, substitution or addition of a nucleotide in the second nucleotide sequence—compared to the first nucleotide sequence—is considered as a difference at a single nucleotide (position). Alternatively, the degree of sequence identity between two or more nucleotide sequences may be calculated using a known computer algorithm for sequence alignment such as NCBI Blast v2.0, using standard settings. Some other techniques, computer algorithms and settings for determining the degree of sequence identity are for example described in WO 04/037999, EP 0967284, EP 1085089, WO 00/55318, WO 00/78972, WO 98/49185 and GB 2357768. Usually, for the purpose of determining the percentage of "sequence identity" between two nucleotide sequences in accordance with the calculation method outlined hereinabove, the nucleotide sequence with the greatest number of nucleotides will be taken as the "first" nucleotide sequence, and the other nucleotide sequence will be taken as the "second" nucleotide sequence.

For the purposes of comparing two or more amino acid sequences, the percentage of "sequence identity" between a first amino acid sequence and a second amino acid sequence (also referred to herein as "amino acid identity") may be calculated by dividing [the number of amino acid residues in the first amino acid sequence that are identical to the amino acid residues at the corresponding positions in the second amino acid sequence] by [the total number of amino acid residues in the first amino acid sequence] and multiplying by [100%], in which each deletion, insertion, substitution or addition of an amino acid residue in the second amino acid sequence—compared to the first amino acid sequence—is considered as a difference at a single amino acid residue (position), i.e., as an "amino acid difference" as defined herein. Alternatively, the degree of sequence identity between two amino acid sequences may be calculated using a known computer algorithm, such as those mentioned above for determining the degree of sequence identity for nucleotide sequences, again using standard settings. Usually, for the purpose of determining the percentage of "sequence identity" between two amino acid sequences in accordance with the calculation method outlined hereinabove, the amino acid sequence with the greatest number of amino acid residues will be taken as the "first" amino acid sequence, and the other amino acid sequence will be taken as the "second" amino acid sequence.

Also, in determining the degree of sequence identity between two amino acid sequences, the skilled person may take into account so-called "conservative" amino acid substitutions, which can generally be described as amino acid substitutions in which an amino acid residue is replaced with another amino acid residue of similar chemical structure and which has little or essentially no influence on the function, activity or other biological properties of the polypeptide. Such conservative amino acid substitutions are well known in the art, for example from WO 04/037999, GB 335768, WO 98/49185, WO 00/46383 and WO 01/09300; and (preferred) types and/or combinations of such substitutions may be selected on the basis of the pertinent teachings from WO 04/037999 as well as WO 98/49185 and from the further references cited therein.

Such conservative substitutions preferably are substitutions in which one amino acid within the following groups (a)-(e) is substituted by another amino acid residue within the same group: (a) small aliphatic, nonpolar or slightly polar residues: Ala, Ser, Thr, Pro and Gly; (b) polar, negatively charged residues and their (uncharged) amides: Asp, Asn, Glu and Gln; (c) polar, positively charged residues: His, Arg and Lys; (d) large aliphatic, nonpolar residues: Met, Leu, Ile, Val and Cys; and (e) aromatic residues: Phe, Tyr and Trp. Particularly preferred conservative substitutions are as follows: Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

Any amino acid substitutions applied to the polypeptides described herein may also be based on the analysis of the frequencies of amino acid variations between homologous proteins of different species developed by Schulz et al. ("Principles of Protein Structure", Springer-Verlag, 1978), on the analyses of structure forming potentials developed by Chou and Fasman (Biochemistry 13: 211, 1974; Adv. Enzymol., 47: 45-149, 1978), and on the analysis of hydrophobicity patterns in proteins developed by Eisenberg et al. (Proc. Natl. Acad Sci. USA 81: 140-144, 1984), Kyte and Doolittle (J. Molec. Biol. 157: 105-132, 1981), and Goldman et al. (Ann. Rev. Biophys. Chem. 15: 321-353, 1986), all incorporated herein in their entirety by reference. Information on the primary, secondary and tertiary structure of NANOBODIES® is given in the description herein and in the general background art cited above. Also, for this purpose, the crystal structure of a $V_{HH}$ domain from a llama is for example given by Desmyter et al. (Nature Structural Biology, 3: 803, 1996), Spinelli et al. (Natural Structural Biology, 3: 752-757, 1996) and Decanniere et al. (Structure, 7 (4): 361, 1999). Further information about some of the amino acid residues that in conventional $V_H$ domains form the VH/VL interface and potential camelizing substitutions on these positions can be found in the prior art cited above.

Amino acid sequences and nucleic acid sequences are said to be "exactly the same" if they have 100% sequence identity (as defined herein) over their entire length.

In an embodiment, the polypeptide of the invention specifically binding CD40L has at least 80%, 90%, 95% or 100% sequence identity with C010003318 (SEQ ID NO: 9) or C010003313 (SEQ ID NO: 78), wherein binding to CD40L modulates an activity of CD40L.

When comparing two amino acid sequences, the term "amino acid difference" refers to an insertion, deletion or substitution of a single amino acid residue on a position of the first sequence, compared to the second sequence; it being understood that two amino acid sequences may contain one, two or more such amino acid differences. More particularly, in the amino acid sequences and/or polypeptides of the present invention, the term "amino acid difference" refers to an insertion, deletion or substitution of a single amino acid residue on a position of a CDR1, CDR2 and/or CDR3 sequence; it being understood that the CDR1 sequence may contain 1, 2 or maximal 3 such amino acid differences compared to the original CDR1 sequence, e.g. the CDR1 sequence exemplified by a specific sequence identifier (SEQ ID NO), such as for instance, SEQ ID NOs: 33, 61, 40 and 68; the CDR2 may contain 1, 2 or maximal 3 such amino acid differences compared to the original CDR2 sequence, e.g. the CDR2 sequence exemplified by a specific sequence identifier (SEQ ID NO:), such as for instance, SEQ ID NOs: 35, 63, 42 and 70, and the CDR3 sequence may contain 1, 2, 3 or maximal 4 such amino acid differences compared to the original CDR3 sequence, e.g. the CDR3 sequence exemplified by a specific sequence identifier (SEQ ID NO:), such as for instance, SEQ ID NOs: 37, 65, 44 and 72.

The "amino acid difference" may be any of one, two, three or maximal four substitutions, deletions or insertions, or any combination thereof, that either improve the properties of the ISVD of the invention or that at least do not detract too much from the desired properties or from the balance or combination of desired properties of the ISVD of the invention. In this respect, the resulting polypeptide of the invention should at least bind CD40L with the same, about the same, or preferably a higher affinity or potency compared to the polypeptide comprising the ISVD binding CD40L comprising one or more CDR sequences without the one, two, three or maximal four substitutions, deletions or insertions. Affinity may be measured for instance by surface plasmon resonance (SPR), for instance as expressed by the $K_{off}$ rate as used in the examples. Potency, e.g. as expressed by $IC_{50}$, may be measured by any suitable method known in the art, such as for instance in B-cell proliferation assays or B-cell signalling assays as used in examples.

In this respect, the amino acid sequence of the CDRs may be an amino acid sequence that is derived from an original CDR amino acid sequence by means of affinity maturation using one or more techniques of affinity maturation known per se, for instance via error prone PCR as used in the examples section. It was demonstrated in the examples section that the affinity and/or potency of the ISVDs of the invention were ameliorated, e.g. single amino acid differences in the CDRs resulted in 1.8 fold to 5.2 fold improved off-rates. Combinations of amino acid differences, e.g. one, two, three or maximal four substitutions, deletions or insertions, or any combination thereof, in the CDRs further improved the off-rates.

Accordingly, the present invention relates to polypeptides as described herein, wherein said polypeptide binds to CD40L with a $K_{off}$ better than 28602 and 46603, respectively, such as at least 1.5 fold, 2 fold, 3 fold, 4 fold, 5 fold or even more, such as 10 fold better, for instance as determined by SPR.

Accordingly, the present invention relates to polypeptides as described herein, wherein said polypeptide binds to CD40L with a $K_{off}$ of at most $5E^{-04}$ s), such as at most $4E^{-04}$ $(s^{-1})$, $3E^{-04}$ $(s^{-1})$, $2E^{-04}$ $(s^{-1})$, $2E^{-04}$ $(s^{-1})$, $1E^{-04}$ $(s^{-1})$, $9E^{-05}$ $(s^{-1})$, $8E^{-05}$ $(s^{-1})$, $7E^{-05}$ $(s^{-1})$, $6E^{-05}$ $(s^{-1})$, $5E^{-05}$ $(s^{-1})$, $4E^{-05}$ $(s^{-1})$, $3E^{-05}$ $(s^{-1})$, $2E^{-05}$ $(s^{-1})$, $10E^{-06}$ $(s^{-1})$, for instance as determined by SPR.

Accordingly, the present invention relates to polypeptides as described herein, wherein said polypeptide binds to CD40L with an $IC_{50}$ between $1E^{-07}$ M and $1E^{-12}$ M, such as between $1E^{-08}$ M and M, preferably at most $1E^{-07}$ M, preferably lower than $1E^{-08}$ M or $1E^{-09}$ M, or even lower than $5E^{-10}$ M, $4E^{-10}$ M, $3E^{-10}$ M, $2E^{-10}$ M, such as $1E^{-10}$ M, for instance as determined by a B cell proliferation assay or B cell signaling assay.

For example, and depending on the host organism used to express the polypeptide of the invention, such insertions, deletions and/or substitutions may be designed in such a way that one or more sites for post-translational modification (such as one or more glycosylation sites) are removed, as will be within the ability of the person skilled in the art.

Accordingly, the present invention relates to a polypeptide as described herein, wherein said ISVD specifically binding CD40L essentially consists of 4 framework regions (FR1 to FR4, respectively) and 3 complementarity determining regions (CDR1 to CDR3 respectively), in which
  (i) CDR1 is chosen from the group consisting of SEQ ID NOs: 33, 61, 40 and 68; and amino acid sequences that have 1, 2 or 3 amino acid difference(s) with SEQ ID NOs: 33, 61, 40 or 68;
  (ii) CDR2 is chosen from the group consisting of SEQ ID NOs: 35, 63, 42 and 70; and amino acid sequences that have 1, 2 or 3 amino acid difference(s) with SEQ ID NOs: 35, 63, 42 or 70; and
  (iii) CDR3 is chosen from the group consisting of SEQ ID NO: 37, 65, 44 and 72; and amino acid sequences that have 1, 2, 3 or 4 amino acid difference(s) with SEQ ID NOs: 37, 65, 44 or 72.

Accordingly, the present invention relates to a polypeptide as described herein, in which CDR1 is chosen from the group consisting of (a) SEQ ID NO: 40; and (b) amino acid sequences that have 1, 2 or 3 amino acid difference(s) with SEQ ID NO: 40, wherein
  at position 3 the T has been changed into S, N, A or I;
  at position 4 the L has been changed into Q, S, M or G;
  at position 8 the A has been changed into N or V;
  at position 9 the I has been changed into L or V; and/or
  at position 10 the G has been changed into A.

Accordingly, the present invention relates to a polypeptide as described herein, in which CDR2 is chosen from the group consisting of (a) SEQ ID NO: 42; and (b) amino acid sequences that have 1, 2 or 3 amino acid difference(s) with SEQ ID NO: 42, wherein
  at position 2 the I has been changed into V;
  at position 3 the S has been changed into G;
  at position 5 the E has been changed into G;
  at position 6 the G has been changed into 5;
  at position 7 the S has been changed into G, N, T or I;
  at position 8 the T has been changed into A, P, I or 5; and/or
  at position 9 the S has been changed into I, R or G.

Accordingly, the present invention relates to a polypeptide as described herein, in which CDR3 is chosen from the group consisting of (a) SEQ ID NO: 44; and (b) amino acid sequences that have 1, 2, 3 or 4 amino acid difference(s) with SEQ ID NO: 44, wherein
at position 4 the R has been changed into S;
at position 7 the L has been changed into F, M or W;
at position 8 the G has been changed into D, A or S;
at position 9 the S has been changed into G, N or R;
at position 10 the S has been changed into G, N, T or R;
at position 12 the D has been changed into G, N, E or V;
at position 13 the T has been changed into N or A;
at position 14 the Q has been changed into H, K, L or R;
at position 15 the S has been changed into P or T;
at position 16 the H has been changed into N or Y;
at position 17 the Q has been changed into L, R or H;
at position 18 the Y has been changed into F;
at position 19 the D has been changed into G; and/or
at position 20 the Y has been changed into F or N.

Accordingly, the present invention relates to a polypeptide as described herein, in which CDR1 is chosen from the group consisting of (a) SEQ ID NO: 61; and (b) amino acid sequences that have 1, 2 or 3 amino acid difference(s) with SEQ ID NO: 61, wherein
at position 1 the G has been changed into E or R;
at position 2 the R has been changed into H or G;
at position 3 the T has been changed into I, A, S or P;
at position 4 the P has been changed into S;
at position 5 the L has been changed into P;
at position 6 the N has been changed into S, D or I;
at position 7 the Y has been changed into H;
at position 8 the H has been changed into N;
at position 9 the M has been changed into K, T or V; and/or
at position 10 the A has been changed into G, S or T.

Accordingly, the present invention relates to a polypeptide as described herein, in which CDR2 is chosen from the group consisting of (a) SEQ ID NO: 63; and (b) amino acid sequences that have 1, 2 or 3 amino acid difference(s) with SEQ ID NO: 63, wherein
at position 1 the A has been changed into G;
at position 2 the I has been changed into V;
at position 4 the S has been changed into N, R or G;
at position 6 the L has been changed into I;
at position 7 the G has been changed into S or D;
at position 8 the S has been changed into G, I or F; and/or
at position 9 the T has been changed into P or S.

Accordingly, the present invention relates to a polypeptide as described herein, in which CDR3 is chosen from the group consisting of (a) SEQ ID NO: 65; and (b) amino acid sequences that have 1, 2, 3 or 4 amino acid difference(s) with SEQ ID NO: 65, wherein
at position 1 the R has been changed into Q or L;
at position 2 the E has been changed into D or K;
at position 3 the T has been changed into S, M, A or K;
at position 4 the T has been changed into I, S, A or R;
at position 5 the H has been changed into Y or N;
at position 6 the Y has been changed into I, H or N;
at position 7 the S has been changed into T, G, N or I;
at position 8 the T has been changed into I or A;
at position 9 the S has been changed into N or R;
at position 10 the D has been changed into A;
at position 11 the R has been changed into S or G;
at position 13 the N has been changed into D, Y or S;
at position 14 the E has been changed into V, A, D or N;
at position 15 the M has been changed into I, V, K or T;
at position 16 the R has been changed into K, S, W, M, G or T;
at position 17 the H has been changed into N, L, Q, R or D;
at position 19 the D has been changed into N; and/or
at position 20 the Y has been changed into H, F or N.

Accordingly, the present invention relates to a polypeptide as described herein, in which
CDR1 is SEQ ID NO: 33, CDR2 is SEQ ID NO: 35 and CDR3 is SEQ ID NO: 37; or
CDR1 is SEQ ID NO: 61, CDR2 is SEQ ID NO: 63 and CDR3 is SEQ ID NO: 65.

Accordingly, the present invention relates to a polypeptide as described herein, in which said ISVD is SEQ ID NO: 8 or SEQ ID NO: 6.

Accordingly, the present invention relates to a polypeptide as described herein, in which CDR1 is SEQ ID NO: 40, CDR2 is SEQ ID NO: 42 and CDR3 is SEQ ID NO: 44.

Accordingly, the present invention relates to a polypeptide as described herein, in which said ISVD is SEQ ID NO: 7 or SEQ ID NO: 3.

A "Nanobody family", "VHH family" or "family" as used in the present specification refers to a group of NANOBODIES® and/or VHH sequences that have identical lengths (i.e. they have the same number of amino acids within their sequence) and of which the amino acid sequence between position 8 and position 106 (according to Kabat numbering) has an amino acid sequence identity of at least 80%, such as for instance 85%, 90%, 95% or even more, e.g. 99%.

The terms "epitope" and "antigenic determinant", which may be used interchangeably, refer to the part of a macromolecule, such as a polypeptide or protein that is recognized by antigen-binding molecules, such as, immunoglobulins, conventional antibodies, immunoglobulin single variable domains, VHHs, NANOBODIES® and/or polypeptides of the invention, and more particularly by the antigen-binding site of said molecules. Epitopes define the minimum binding site for an immunoglobulin, and thus represent the target of specificity of an immunoglobulin.

The part of an antigen-binding molecule (such as an immunoglobulin, a conventional antibody, an immunoglobulin single variable domain and/or a polypeptide of the invention) that recognizes the epitope is called a "paratope".

A polypeptide (such as an immunoglobulin, an antibody, an immunoglobulin single variable domain, a polypeptide of the invention, or generally an antigen binding molecule or a fragment thereof) that may "bind to" or "specifically bind to", that "has affinity for" and/or that "has specificity for" a certain epitope, antigen or protein (or for at least one part, fragment or epitope thereof) is said to be "against" or "directed against" said epitope, antigen or protein or is a "binding" molecule with respect to such epitope, antigen or protein, or is said to be "anti"-epitope, "anti"-antigen or "anti"-protein (e.g., "anti"-CD40L).

The affinity denotes the strength or stability of a molecular interaction. The affinity is commonly given as by the $K_D$, or dissociation constant, which has units of mol/liter (or M). The affinity may also be expressed as an association constant, $K_A$, which equals $1/K_D$ and has units of $(mol/liter)^{-1}$ (or $M^{-1}$). In the present specification, the stability of the interaction between two molecules will mainly be expressed in terms of the $K_D$ value of their interaction; it being clear to the skilled person that in view of the relation $K_A=1/K_D$, specifying the strength of molecular interaction by its $K_D$ value may also be used to calculate the corresponding $K_A$ value. The $K_D$-value characterizes the strength of a molecular interaction also in a thermodynamic sense as it is related to the change of free energy (DG) of binding by the well-known relation $DG=RT \cdot \ln(K_D)$ (equivalently $DG=-RT\cdot\ln(K_A)$), where R equals the gas constant, T equals the absolute temperature and ln denotes the natural logarithm.

The $K_D$ for biological interactions which are considered meaningful (e.g. specific) are typically in the range of $10^{-10}$M (0.1 nM) to $10^{-5}$M (10000 nM). The stronger an interaction is, the lower is its $K_D$.

The $K_D$ may also be expressed as the ratio of the dissociation rate constant of a complex, denoted as $k_{off}$, to the rate of its association, denoted $K_{on}$ (so that $K_D=k_{off}/k_{on}$ and $K_A=k_{on}/k_{off}$). The off-rate $k_{off}$ has units s$^{-1}$ (where s is the SI unit notation of second). The on-rate $K_{on}$ has units M$^{-1}$s$^{-1}$. The on-rate may vary between $10^2$ M$^{-1}$s$^{-1}$ to about $10^7$ M$^{-1}$s$^{-1}$, approaching the diffusion-limited association rate constant for bimolecular interactions. The off-rate is related to the half-life of a given molecular interaction by the relation $t_{1/2}=\ln(2)/k_{off}$. The off-rate may vary between $10^{-6}$ s$^{-1}$ (near irreversible complex with a $t_{1/2}$ of multiple days) to 1 s$^{-1}$ ($t_{1/2}$=0.69 s).

The measured $K_D$ may correspond to the apparent $K_D$ if the measuring process somehow influences the intrinsic binding affinity of the implied molecules for example by artefacts related to the coating on the biosensor of one molecule. Also, an apparent $K_D$ may be measured if one molecule contains more than one recognition sites for the other molecule. In such situation the measured affinity may be affected by the avidity of the interaction by the two molecules.

Another approach that may be used to assess affinity is the 2-step ELISA (Enzyme-Linked Immunosorbent Assay) procedure of Friguet et al. (J. Immunol. Methods, 77, 305-19, 1985). This method establishes a solution phase binding equilibrium measurement and avoids possible artefacts relating to adsorption of one of the molecules on a support such as plastic.

However, the accurate measurement of $K_D$ may be quite labour-intensive and as consequence, often apparent $K_D$ values are determined to assess the binding strength of two molecules. It should be noted that as long as all measurements are made in a consistent way (e.g. keeping the assay conditions unchanged) apparent $K_D$ measurements may be used as an approximation of the true $K_D$ and hence in the present document $K_D$ and apparent $K_D$ should be treated with equal importance or relevance.

Finally, it should be noted that in many situations the experienced scientist may judge it to be convenient to determine the binding affinity relative to some reference molecule. For example, to assess the binding strength between molecules A and B, one may e.g. use a reference molecule C that is known to bind to B and that is suitably labelled with a fluorophore or chromophore group or other chemical moiety, such as biotin for easy detection in an ELISA or FACS (Fluorescent activated cell sorting) or other format (the fluorophore for fluorescence detection, the chromophore for light absorption detection, the biotin for streptavidin-mediated ELISA detection). Typically, the reference molecule C is kept at a fixed concentration and the concentration of A is varied for a given concentration or amount of B. As a result an $IC_{50}$ value is obtained corresponding to the concentration of A at which the signal measured for C in absence of A is halved. Provided $K_D$ ref, the $K_D$ of the reference molecule, is known, as well as the total concentration $c_{ref}$ of the reference molecule, the apparent $K_D$ for the interaction A-B may be obtained from following formula: $K_D=IC_{50}/(1+C_{ref}/K_{Dref})$. Note that if $c_{ref}\ll K_D$ ref, $K_D=IC_{50}$. Provided the measurement of the $IC_{50}$ is performed in a consistent way (e.g. keeping $c_{ref}$ fixed) for the binders that are compared, the strength or stability of a molecular interaction may be assessed by the $IC_{50}$ and this measurement is judged as equivalent to $K_D$ or to apparent $K_D$ throughout this text.

Specific binding of an antigen-binding protein, such as an ISVD, to an antigen or antigenic determinant may be determined in any suitable manner known per se, including, for example, Scatchard analysis and/or competitive binding assays, such as radio-immunoassays (RIA), enzyme immunoassays (EIA) and sandwich competition assays, and the different variants thereof known per se in the art; as well as the other techniques mentioned herein.

The affinity of a molecular interaction between two molecules may be measured via different techniques known per se, such as the well-known surface plasmon resonance (SPR) biosensor technique (see for example Ober et al., 2001, Intern. Immunology 13: 1551-1559) where one molecule is immobilized on the biosensor chip and the other molecule is passed over the immobilized molecule under flow conditions yielding $k_{on}$, $k_{off}$ measurements and hence $K_D$ (or $K_A$) values. This may for example be performed using the well-known BIACORE® instruments (Pharmacia Biosensor AB, Uppsala, Sweden). Kinetic Exclusion Assay (KinExA) (Drake et al., 2004, Analytical Biochemistry 328: 35-43) measures binding events in solution without labeling of the binding partners and is based upon kinetically excluding the dissociation of a complex.

It was demonstrated that the polypeptides of the present invention have outstanding affinities.

Accordingly, the present invention relates to polypeptides as described herein, wherein said polypeptide binds to CD40L with a $K_D$ between $1E^{-07}$M and $1E^{-13}$ M, such as between $1E^{-08}$ M and $1E^{-12}$ M, preferably at most $1E^{-07}$ M, preferably lower than $1E^{-08}$ M or $1E^{-09}$ M, or even lower than $1E^{-10}$ M, such as $5E^{-11}$ M, $4E^{-11}$ M, $3E^{-11}$ M, $2E^{-11}$ M, $1.7E^{-11}$ M, $1E^{-11}$, or even $5E^{-12}$ M, $4E^{-12}$ M, $3E^{-12}$ M, $1E^{-12}$ M, for instance as determined by a KinExA.

The Gyrolab™ immunoassay system provides a platform for automated bioanalysis and rapid sample turnaround (Fraley et al., 2013, Bioanalysis 5: 1765-74).

It will also be clear to the skilled person that the measured $K_D$ may correspond to the apparent $K_D$ if the measuring process somehow influences the intrinsic binding affinity of the implied molecules for example by artifacts related to the coating on the biosensor of one molecule. Also, an apparent $K_D$ may be measured if one molecule contains more than one recognition sites for the other molecule. In such situation the measured affinity may be affected by the avidity of the interaction by the two molecules.

The term "specificity" has the meaning given to it in paragraph n) on pages 53-56 of WO 08/020079; and as mentioned therein refers to the number of different types of antigens or antigenic determinants to which a particular antigen-binding molecule or antigen-binding protein (such as an immunoglobulin single variable domain and/or a polypeptide of the invention) may bind. The specificity of an antigen-binding protein may be determined based on affinity and/or avidity, as described on pages 53-56 of WO 08/020079 (incorporated herein by reference), which also describes some preferred techniques for measuring binding between an antigen-binding molecule (such as an immunoglobulin single variable domain and/or polypeptide of the invention) and the pertinent antigen. Typically, antigen-binding proteins (such as the immunoglobulin single variable domains and/or polypeptides of the invention) will bind to their antigen with a dissociation constant ($K_D$) of $10^{-5}$ to $10^{-12}$ moles/liter or less, and preferably $10^{-7}$ to $10^{-12}$ moles/ liter or less and more preferably $10^{-8}$ to $10^{-12}$ moles/liter (i.e. with an association constant ($K_A$) of $10^5$ to $10^{12}$ liter/moles or more, and preferably $10^7$ to $10^{12}$ liter/moles or more and more preferably $10^8$ to $10^{12}$ liter/moles). Any $K_D$ value greater than $10^{-4}$ mol/liter (or any $K_A$ value lower than $10^4$ M$^{-1}$) liters/mol is generally considered to indicate non-specific binding. Preferably, a monovalent polypeptide of the invention will bind to the desired antigen with an affinity less than 500 nM, preferably less than 200 nM, more preferably less than 10 nM, such as e.g., between 10 and 5 nM or less. Specific binding of an antigen-binding protein to an antigen or antigenic determinant may be determined in any suitable manner known per se, including, for example, Scatchard analysis and/or competitive binding assays, such as radioimmunoassays (RIA), enzyme immunoassays (EIA) and sandwich competition assays, and the different variants thereof known per se in the art; as well as the other techniques mentioned herein. As will be clear to the skilled person, and as described on pages 53-56 of WO 08/020079, the dissociation constant may be the actual or apparent dissociation constant. Methods for determining the dissociation constant will be clear to the skilled person, and for example include the techniques mentioned on pages 53-56 of WO 08/020079.

An immunoglobulin single variable domain and/or polypeptide is said to be "specific for" a first target or antigen, e.g. an epitope of CD40L, compared to a second target or antigen when it binds to the first antigen with an affinity (as described above, and suitably expressed as a $K_D$ value, $K_A$ value, $K_{off}$ rate and/or $K_{on}$ rate) that is at least 10 times, such as at least 100 times, and preferably at least 1000 times, and up to 10000 times or more better than the affinity with which the immunoglobulin single variable domain and/or polypeptide binds to the second target or antigen, i.e. different from the first target or antigen, e.g. different from the said epitope of CD40L. For example, the immunoglobulin single variable domain and/or polypeptide may bind to the first target or antigen with a $K_D$ value that is at least 10 times less, such as at least 100 times less, and preferably at least 1000 times less, such as 10000 times less or even less than that, than the $K_D$ with which said immunoglobulin single variable domain and/or polypeptide binds to the second target or antigen. Preferably, when an immunoglobulin single variable domain and/or polypeptide is "specific for" a first target or antigen compared to a second target or antigen, it is directed against (as defined herein) said first target or antigen, but not directed against said second target or antigen.

CD40L is also known as CD 154, gp39, TNF-related activation protein (TRAP), 5c8 antigen, or T-BAM. Relevant structural information for human CD40L may be found, for example, at UniProt Accession Number P29965. "Human CD40L" refers to the CD40L comprising the amino acid sequence of SEQ ID NO: 1. In an aspect the polypeptide of the invention specifically binds CD40L from Human *sapiens, Mus musculus, Canis familiaris, Bos taurus, Macaca mulatta, Macaca fascicularis, Macaca nemestrina, Aotus tivirgatus, Callithrix jacchus, Cercocebus torquatus atys, Rattus norvegicus, Gallus, Felis catus*, and/or *Sus scrofa*, which have also been sequenced, preferably human CD40L, preferably SEQ ID NO: 1.

The terms "(cross)-block", "(cross)-blocked", "(cross)-blocking", "competitive binding", "(cross)-compete", "(cross)-competing" and "(cross)-competition" are used interchangeably herein to mean the ability of an immunoglobulin, antibody, immunoglobulin single variable domain, polypeptide or other binding agent to interfere with the binding of other immunoglobulins, antibodies, immunoglobulin single variable domains, polypeptides or binding agents to a given target. The extent to which an immunoglobulin, antibody, immunoglobulin single variable domain, polypeptide or other binding agent is able to interfere with the binding of another to the target, and therefore whether it may be said to cross-block according to the invention, may be determined using competition binding assays, such as for instance by screening purified ISVDs against ISVDs displayed on phage in a competition ELISA as described in the examples. If an ISVD binding to CD40L fully competes with another ISVD binding to CD40L (e.g. the purified ISVD in the competition ELISA), said ISVDs belong to the same epitope bin. If an ISVD binding to CD40L does not compete or only partially competes with another ISVD binding to CD40L (e.g. the purified ISVD in the competition ELISA), said ISVDs belong to a different epitope bin. 7 different epitope bins were identified within the lead panel of ISVDs binding to CD40L.

Accordingly, the present invention relates to a polypeptide as described herein, such as SEQ ID NO: 3, 4, 5, 6, 7, 8, 9, 78, 79, 80, 81 or 82, wherein said polypeptide competes with a polypeptide, for instance as determined by competition ELISA.

The present invention relates to a method for determining competitors, such as polypeptides, competing with a polypeptide as described herein, such as SEQ ID NO: 3, 4, 5, 6, 7, 8, 9, 78, 79, 80, 81 or 82, wherein the polypeptide as described herein competes with or cross blocks the competitor polypeptide for binding to CD40L, such as, for instance hCD40L (SEQ ID NO: 1), wherein the binding to CD40L of the competitor is reduced by at least 5%, such as 10%, 20%, 30%, 40%, 50% or even more, such as 80%, 90% or even 100% (i.e. virtually undetectable in a given assay) in the presence of a polypeptide of the invention, compared to the binding to CD40L of the competitor in the absence of the polypeptide of the invention. Competition and cross blocking may be determined by any means known in the art, such as, for instance, competition ELISA or FACS assay. In an aspect the present invention relates to a polypeptide of the invention, wherein said polypeptide cross-blocks the binding to CD40L of at least one of the polypeptides 46B03 (SEQ ID NO: 6), 28B02 (SEQ ID NO: 3) C010003290 (SEQ ID NO: 8) and C010003318 (SEQ ID NO: 9) and/or is cross-blocked from binding to CD40L by at least one of the polypeptides 46603 (SEQ ID NO: 6), 28602 (SEQ ID NO: 3) C010003290 (SEQ ID NO: 8) and C010003318 (SEQ ID NO: 9).

The present invention also relates to competitors competing with a polypeptide as described herein, such as SEQ ID NO: 3, 4, 5, 6, 7, 8, 9, 78, 79, 80, 81 or 82, wherein the competitor competes with or cross blocks the polypeptide as described herein for binding to CD40L, wherein the binding to CD40L of the polypeptide of the invention is reduced by at least 5%, such as 10%, 20%, 30%, 40%, 50% or even more, such as 80%, or even more such as at least 90% or even 100% (i.e. virtually undetectable in a given assay) in the presence of said competitor, compared to the binding to CD40L by the polypeptide of the invention in the absence of said competitor. In an aspect the present invention relates to a polypeptide cross-blocking binding to CD40L by a polypeptide of the invention such as one of 46603 (SEQ ID NO: 6), 28602 (SEQ ID NO: 3) C010003290 (SEQ ID NO: 8) and C010003318 (SEQ ID NO: 9) and/or is cross-blocked from binding to CD40L by at least one of 46603 (SEQ ID NO: 6), 28602 (SEQ ID NO: 3) C010003290 (SEQ ID NO: 8) and C010003318 (SEQ ID NO: 9), wherein said polypeptide comprises at least one VH, VL, dAb, immunoglobulin single variable domain (ISVD) specifically binding to CD40L, wherein binding to CD40L modulates an activity of CD40L.

Suitable FACS assay for determining whether an immunoglobulin, antibody, immunoglobulin single variable domain, polypeptide or other binding agent cross-blocks or is capable of cross-blocking according to the invention is described below. It will be appreciated that the assay may be used with any of the immunoglobulins, antibodies, immunoglobulin single variable domains, polypeptides or other binding agents described herein. The FACS instrument (e.g. FACS Canto; Becton Dickinson) is operated in line with the manufacturer's recommendations.

To evaluate the "(cross)-blocking" or "(cross)-competition" between two binding agents (such as e.g. two immunoglobulin single variable domains and/or NANOBODIES®) for binding CD40L a FACS competition experiment may be performed using cells (such as e.g. CHO cells or HEK293H cells) overexpressing human CD40L and the parental cells as background cell line. Different detection reagents may be used including e.g. monoclonal ANTI-FLAG® M2 antibody (Sigma-Aldrich, cat #F1804), monoclonal anti-C-myc antibody (Sigma-Aldrich, cat #WH0004609M2), monoclonal ANTI-HIS TAG antibody (Sigma-Aldrich, cat #SAB1305538), each labeled differently.

A wide range of fluorophores may be used as labels in flow cytometry, known to the skilled person. Fluorophores, or simply "fluors", are typically attached to the antibody (e.g. the immunoglobulin single variable domains and/or NANOBODIES®) that recognizes CD40L or to the antibody that is used as detection reagent. Various conjugated antibodies are available, such as (without being limiting) for example antibodies conjugated to ALEXA FLUOR®, DYLIGHT®, Rhodamine, PE, FITC, and CY3®.

Other methods for determining whether an immunoglobulin, antibody, immunoglobulin single variable domain, polypeptide or other binding agent directed against a target (cross)-blocks, is capable of (cross)-blocking, competitively binds or is (cross)-competitive as defined herein are described e.g. in Xiao-Chi Jia et al. (Journal of Immunological Methods 288: 91-98, 2004), Miller et al. (Journal of Immunological Methods 365: 118-125, 2011) and/or the methods described herein (see e.g. Example 7).

An amino acid sequence is said to be "cross-reactive" for two different antigens or antigenic determinants (such as e.g., serum albumin from two different species of mammal, such as e.g., human serum albumin and cynomolgus ("cyno") serum albumin, such as e.g., CD40L from different species of mammal, such as e.g., human CD40L, cyno CD40L and rat CD40L) if it is specific for (as defined herein) these different antigens or antigenic determinants. It will be appreciated that an amino acid sequence or polypeptide may be considered to be cross-reactive although the binding affinity for the two different antigens can differ, such as by a factor, 2, 5, 10, 50, 100 or even more provided it is specific for (as defined herein) these different antigens or antigenic determinants.

In the context of the present invention, "modulating" or "to modulate" generally means altering an activity of CD40L, as measured using a suitable in vitro, cellular or in vivo assay (such as those mentioned herein). In particular, "modulating" or "to modulate" may mean either reducing or inhibiting an activity of, or alternatively increasing an activity of CD40L, as measured using a suitable in vitro, cellular or in vivo assay (for instance, such as those mentioned herein), by at least 1%, preferably at least 5%, such as at least 10% or at least 25%, for example by at least 50%, at least 60%, at least 70%, at least 80%, or 90% or more, compared to activity of CD40L in the same assay under the same conditions but without the presence of the immunoglobulin or polypeptide of the invention.

"Modulating" may also mean effecting a change with respect to one or more biological or physiological mechanisms, effects, responses, functions, pathways or activities in which CD40L (or in which its substrate(s), ligand(s) or pathway(s) are involved, such as its signalling pathway or metabolic pathway and their associated biological or physiological effects) is involved. Again, as will be clear to the skilled person, such an action may be determined in any suitable manner and/or using any suitable (in vitro and usually cellular or in vivo assay) assay known per se, such as the assays described herein or in the prior art cited herein. In particular, an action may be such that an intended biological or physiological activity is increased or decreased, respectively, by at least 1%, preferably at least 5%, such as at least 10% or at least 25%, for example by at least 50%, at least 60%, at least 70%, at least 80%, or 90% or more, compared to the biological or physiological activity in the same assay under the same conditions but without the presence of the immunoglobulin, ISVD or polypeptide of the invention. Modulation may involve the reduction and/or inhibition of B-cell and/or T-cell activation and/or proliferation. Modulation may involve the reduction, inhibition and/or suppression of (unwanted) immune responses.

"CD40L activities" and "activities by CD40L" (these terms are used interchangeably herein) include, but are not limited to, costimulation and activation an APC in association with T-cell receptor stimulation by MHC molecules on the APC, secretion of all immunoglobulin isotypes in the presence of cytokines, stimulation of B-cell proliferation, B-cell activation, cytokine production, antibody class switching and affinity maturation. For example, patients with X-linked hyper-IgM syndrome express functional CD40 on their B-cells, but their activated T-cells have a defective CD40L protein, resulting in its inability to activate B-cells and induce immunoglobulin isotype switching (Aruffo et al., 1993 Cell 72:291-300).

CD40L activities may be mediated by interaction with other molecules. "CD40L activities" include the functional interaction between CD40L and the following molecules: CD40 (CD40L receptor; e.g. hCD40 SEQ ID NO: 2), α5β1 integrin, and αI3/4β3. For example, CD40L binds its receptor, CD40, which is expressed on a variety of APCs, such as B cells, macrophages, and dendritic cells, as well as on stromal cells, vascular endothelial cells, and platelets. As such, CD40L activities include CD40 mediated induction of T-cell costimulatory molecules such as CD80 and CD86 and immunostimulatory molecules such as IL12.

As used herein, the terms "activate", "activates" and "activated" refer to an increase in a given measurable CD40L activity by at least 10% relative to a reference, for example, at least 10%, 25%, 50%, 75%, or even 100%, or more. A CD40L activity is "antagonized" if the activity is reduced by at least 10%, and in an exemplary embodiment, at least 20%, 30%, 40%, 50%, 60%, 70%, 80%, 90%, 95%, 97%, or even 100%) (i.e., no detectable activity), relative to the absence of the antagonist. For example, a polypeptide of the invention may antagonize some or all CD40L activity. In one embodiment, the polypeptide of the invention does not activate B cell proliferation. In another embodiment, the polypeptide of the invention does not activate cytokine secretion by T cells or dendritic cells (DCs), where the cytokine is at least one cytokine selected from the group consisting of IL-2, IL-6, IL-10, IL-12, IL-13, IL-17, IL-23, TNF-α, and IFN-γ.

Accordingly, the present invention relates to a polypeptide as described herein, wherein said polypeptide modulates the activity of CD40L by antagonizing an activity of CD40L.

Accordingly, the present invention relates to a polypeptide as described herein, wherein said polypeptide blocks the binding of CD40L to CD40, preferably by at least 70%, such as 80%, 90%, 95% or even more, as determined by ligand competition/as determined by (B cell activation FACS; as determined by ALPHASCREEN®, see also Examples section).

Accordingly, the present invention relates to a polypeptide as described herein, wherein said polypeptide antagonizes CD40 mediated induction of T-cell costimulatory molecules such as CD80 and CD86 and immunostimulatory molecules such as IL12.

Accordingly, the present invention relates to a polypeptide as described herein, wherein said polypeptide antagonizes B-cell activation.

Accordingly, the present invention relates to a polypeptide as described herein, wherein said polypeptide does not substantially induce JNK phosphorylation in Jurkat T-cells or does not substantially induce IFN-γ secretion by Jurkat T-cells co-stimulated with anti-CD3 antibody.

Accordingly, the present invention relates to a polypeptide as described herein, wherein said polypeptide antagonizes B-cell activation, for instance as determined by a TT IgG assay, e.g. in a mouse or a monkey.

In an embodiment, the polypeptide of the invention does not substantially induce activation of primary endothelial cells.

In an embodiment, the polypeptide of the invention does not substantially induce platelet activation or platelet aggregation, for instance as determined by a platelet activation assay or platelet aggregation assay.

The term "potency" of a polypeptide of the invention, as used herein, is a function of the amount of polypeptide of the invention required for its specific effect to occur. It is measured simply as the inverse of the $IC_{50}$ for that polypeptide. It refers to the capacity of said polypeptide of the invention to modulate and/or partially or fully inhibit an activity of CD40L. More particularly, it may refer to the capacity of said polypeptide to reduce or even totally inhibit the activity of CD40L activity as defined herein. As such, it may refer to the capacity of said polypeptide to inhibit proliferation of T-cells and/or suppress activation of T-cells resulting in the inhibition of certain immune responses in vivo.

The potency may be measured by any suitable assay known in the art or described herein.

The "efficacy" of the polypeptide of the invention measures the maximum strength of the effect itself, at saturating polypeptide concentrations. Efficacy indicates the maximum response achievable from the polypeptide of the invention. It refers to the ability of a polypeptide to produce the desired (therapeutic) effect.

Amino acid sequences are interpreted to mean a single amino acid or an unbranched sequence of two or more amino acids, depending of the context. Nucleotide sequences are interpreted to mean an unbranched sequence of 3 or more nucleotides.

Amino acids are those L-amino acids commonly found in naturally occurring proteins and are commonly known in the art. Those amino acid sequences containing D-amino acids are not intended to be embraced by this definition. Any peptide or protein that may be expressed as a sequence modified linkages, cross links and end caps, non-peptidyl bonds, etc., is embraced by this definition.

The terms "protein", "peptide", "protein/peptide", and "polypeptide" are used interchangeably throughout the disclosure and each has the same meaning for purposes of this disclosure. Each term refers to an organic compound made of a linear chain of two or more amino acids. The compound may have ten or more amino acids; twenty-five or more amino acids; fifty or more amino acids; one hundred or more amino acids, two hundred or more amino acids, and even three hundred or more amino acids. The skilled artisan will appreciate that polypeptides generally comprise fewer amino acids than proteins, although there is no art-recognized cut-off point of the number of amino acids that distinguish a polypeptides and a protein; that polypeptides may be made by chemical synthesis or recombinant methods; and that proteins are generally made in vitro or in vivo by recombinant methods as known in the art.

By convention, the amide bond in the primary structure of polypeptides is in the order that the amino acids are written, in which the amine end (N-terminus) of a polypeptide is always on the left, while the acid end (C-terminus) is on the right.

The polypeptide of the invention comprises at least one immunoglobulin single variable domain (ISVD) binding CD40L and preferably also an ISVD binding serum albumin. In a polypeptide of the invention, the ISVDs may be directly linked or linked via a linker. Even more preferably, the polypeptide of the invention comprises a C-terminal extension. As will be detailed below, the C-terminal extension essentially prevents/removes binding of pre-existing antibodies/factors in most samples of human subjects/patients. The C-terminal extension is present C-terminally of the last amino acid residue (usually a serine residue) of the last (most C-terminally located) ISVD.

The relative affinities may depend on the location of the ISVDs in the polypeptide. It will be appreciated that the order of the ISVDs in a polypeptide of the invention (orientation) may be chosen according to the needs of the person skilled in the art. The order of the individual ISVDs as well as whether the polypeptide comprises a linker is a matter of design choice. Some orientations, with or without linkers, may provide preferred binding characteristics in comparison to other orientations. For instance, the order of a first ISVD (e.g. ISVD 1) and a second ISVD (e.g. ISVD 2) in the polypeptide of the invention may be (from N-terminus to C-terminus): (i) ISVD 1 (e.g. NANOBODY® 1)-[linker]-ISVD 2 (e.g. NANOBODY® 2)-[C-terminal extension]; or (ii) ISVD 2 (e.g. NANOBODY® 2)-[linker]-ISVD 1 (e.g. NANOBODY® 1)-[C-terminal extension]; (wherein the moieties between the square brackets, i.e. linker and C-terminal extension, are optional). All orientations are encompassed by the invention. Polypeptides that contain an orientation of ISVDs that provides desired binding characteristics may be easily identified by routine screening, for instance as exemplified in the examples section. The preferred order is from N-terminus to C-terminus: ISVD binding CD40L-[linker]-ISVD binding serum albumin-[C-terminal extension], wherein the moieties between the square brackets are optional.

In the polypeptides of the invention, the two or more ISVDs, such as NANOBODIES®, may be directly linked to each other (as for example described in WO 99/23221) and/or may be linked to each other via one or more suitable linkers, or any combination thereof. Suitable linkers for use in the polypeptides of the invention will be clear to the skilled person, and may generally be any linker used in the art to link amino acid sequences. Preferably, said linker is suitable for use in constructing proteins or polypeptides that are intended for pharmaceutical use.

Some particularly preferred linkers include the linkers that are used in the art to link antibody fragments or antibody domains. These include the linkers mentioned in the publications cited above, as well as for example linkers that are used in the art to construct diabodies or ScFv fragments (in this respect, however, it should be noted that, whereas in diabodies and in ScFv fragments, the linker sequence used should have a length, a degree of flexibility and other properties that allow the pertinent $V_H$ and $V_L$ domains to come together to form the complete antigen-binding site, there is no particular limitation on the length or the flexibility of the linker used in the polypeptide of the invention, since each ISVD, such as a NANOBODY® by itself forms a complete antigen-binding site).

For example, a linker may be a suitable amino acid or amino acid sequence, and in particular amino acid sequences of between 1 and 50, preferably between 1 and 30, such as between 1 and 10 amino acid residues. Some preferred examples of such amino acid sequences include gly-ser linkers, for example of the type $(gly_xser_y)_z$, such as (for example $(gly_4ser)_3$ or $(gly_3ser_2)_3$, as described in WO 99/42077 and the GS30, GS15, GS9 and GS7 linkers described in the applications by Ablynx mentioned herein (see for example WO 06/040153 and WO 06/122825), as well as hinge-like regions, such as the hinge regions of naturally occurring heavy chain antibodies or similar sequences (such as described in WO 94/04678). Preferred linkers are depicted in Table 1.

Some other particularly preferred linkers are poly-alanine (such as AAA), as well as the linkers GS30 (SEQ ID NO: 85 in WO 06/122825) and GS9 (SEQ ID NO: 84 in WO 06/122825). In a preferred aspect the linker is chosen from the group consisting of SEQ ID NOs: 18-29 and 77, preferably SEQ ID NO: 21.

It is encompassed within the scope of the invention that the length, the degree of flexibility and/or other properties of the linker(s) used (although not critical, as it usually is for linkers used in ScFv fragments) may have some influence on the properties of the final polypeptide of the invention, including but not limited to the affinity, specificity or avidity for a chemokine, or for one or more of the other antigens. Based on the disclosure herein, the skilled person will be able to determine the optimal linker(s) for use in a specific polypeptide of the invention, optionally after some limited routine experiments.

When two or more linkers are used in the polypeptides of the invention, these linkers may be the same or different. Again, based on the disclosure herein, the skilled person will be able to determine the optimal linkers for use in a specific polypeptide of the invention, optionally after some limited routine experiments.

In the polypeptides of the invention, the ISVDs may be preceded by an N-terminal extension. In the context of the present invention, the N-terminal extension consists of an amino acid sequence of at least one amino acid residue to maximal 40 amino acid residues, preferably between 2 and 30 amino acid residues, such as between 2 and 20 amino acid residues, such as for instance, 2, 3, 4, 5, 6, 7, 8, 9 or 10 amino acid residues. The N-terminal extension is present N-terminally of the first (i.e. most N-terminally located, generally designated by amino acid 1 according to the Kabat numbering) amino acid residue of the first (i.e. most N-terminally located) ISVD in the polypeptide of the invention. Accordingly, the present invention relates to a first polypeptide and/or said second polypeptide comprising an N-terminal extension.

As further elaborated infra, the ISVDs may be derived from a $V_{HH}$, $V_H$ or a $V_L$ domain, however, the ISVDs are chosen such that they do not form complementary pairs of $V_H$ and $V_L$ domains in the polypeptides of the invention of the invention. The NANOBODY®, $V_{HH}$, and humanized $V_{HH}$ are unusual in that they are derived from natural camelid antibodies which have no light chains, and indeed these domains are unable to associate with camelid light chains to form complementary $V_{HH}$ and $V_L$ pairs. Thus, the polypeptides of the present invention do not comprise complementary ISVDs and/or form complementary ISVD pairs, such as, for instance, complementary $V_H/V_L$ pairs.

The present invention relates to a polypeptide as described herein, wherein said linker is chosen from the group consisting of SEQ ID NOs: 18-29 and 77.

It is also contemplated that the polypeptide according to the invention may be conjugated with a further molecule. The further molecule may be conjugated to the polypeptide directly or via a spacer of suitable length. For therapeutic purposes, conjugation with a therapeutic effector group, such as a radioactive group, i.e. a group consisting of or comprising a radioisotope or radionuclide (e.g. $^3$H, $^{14}$C, $^{15}$N, $^{33}$P, $^{35}$S, $^{90}$Y, $^{99}$Tc, $^{111}$In, $^{123}$I, $^{125}$I, $^{131}$I, $^{201}$Tl, $^{213}$Bi), a toxin, or a cytotoxic group, e.g. a cell growth inhibitor may be suitable. In another aspect, the polypeptide of the invention may be coupled to a labeling group (labeled polypeptide), which may then be used e.g. for diagnostic purposes. Suitable labeling groups may be selected from radioisotopes (e.g. those mentioned supra) or groups containing a radioisotope, radionuclides, fluorescent groups (e.g. fluorescent proteins such as GFP, RFP etc., ALEXA FLUOR® dyes, rhodamines, fluorescein and its derivatives such as FITC, cyanine dyes such as CY3® and CY5®), enzymatic groups (e.g. horseradish peroxidase, alkaline phosphatase, β-galactosidase), chemiluminescent groups, biotinyl groups, metal particles, (e.g. gold particles), magnetic particles (e. g. with a core containing magnetite ($Fe_3O_4$) and/or maghemite ($Fe_2O_3$)), predetermined polypeptide groups, etc.

Unless indicated otherwise, the terms "immunoglobulin" and "immunoglobulin sequence"—whether used herein to refer to a heavy chain antibody or to a conventional 4-chain antibody—is used as a general term to include both the full-size antibody, the individual chains thereof, as well as all parts, domains or fragments thereof (including but not limited to antigen-binding domains or fragments such as $V_{HH}$ domains or VH/VL domains, respectively).

The term "domain" (of a polypeptide or protein) as used herein refers to a folded protein structure which has the ability to retain its tertiary structure independently of the rest of the protein. Generally, domains are responsible for discrete functional properties of proteins, and in many cases may be added, removed or transferred to other proteins without loss of function of the remainder of the protein and/or of the domain.

The term "immunoglobulin domain" as used herein refers to a globular region of an antibody chain (such as e.g., a chain of a conventional 4-chain antibody or of a heavy chain antibody), or to a polypeptide that essentially consists of such a globular region. Immunoglobulin domains are characterized in that they retain the immunoglobulin fold characteristic of antibody molecules, which consists of a twolayer sandwich of about seven antiparallel beta-strands arranged in two beta-sheets, optionally stabilized by a conserved disulphide bond.

The term "immunoglobulin variable domain" as used herein means an immunoglobulin domain essentially consisting of four "framework regions" which are referred to in the art and herein below as "framework region 1" or "FR1"; as "framework region 2" or "FR2"; as "framework region 3" or "FR3"; and as "framework region 4" or "FR4", respectively; which framework regions are interrupted by three "complementarity determining regions" or "CDRs", which are referred to in the art and herein below as "complementarity determining region 1" or "CDR1"; as "complementarity determining region 2" or "CDR2"; and as "complementarity determining region 3" or "CDR3", respectively. Thus, the general structure or sequence of an immunoglobulin variable domain may be indicated as follows: FR1-CDR1-FR2-CDR2-FR3-CDR3-FR4. It is the immunoglobulin variable domain(s) that confer specificity to an antibody for the antigen by carrying the antigen-binding site.

Preferred CDRs are depicted in Table A-2, i.e. CDR1 is chosen from SEQ ID NOs: 40, 47, 54, 61, 68, and 33, CDR2 is chosen from SEQ ID NOs: 42, 49, 56, 63, 70 and 35; and CDR3 is chosen from SEQ ID NOs: 44, 51, 58, 65, 72 and 37. Preferably, CDR1, CDR2 and CDR3 are chosen from one clone, e.g.

CDR1 is SEQ ID NO: 33, CDR2 is SEQ ID NO: 35 and CDR3 is SEQ ID NO: 37;
CDR1 is SEQ ID NO: 61, CDR2 is SEQ ID NO: 63 and CDR3 is SEQ ID NO: 65;
CDR1 is SEQ ID NO: 40, CDR2 is SEQ ID NO: 42 and CDR3 is SEQ ID NO: 44;
CDR1 is SEQ ID NO: 68, CDR2 is SEQ ID NO: 70 and CDR3 is SEQ ID NO: 72;
CDR1 is SEQ ID NO: 47, CDR2 is SEQ ID NO: 49 and CDR3 is SEQ ID NO: 51; or
CDR1 is SEQ ID NO: 54, CDR2 is SEQ ID NO: 56 and CDR3 is SEQ ID NO: 58.

The term "immunoglobulin single variable domain", interchangeably used with "single variable domain", defines molecules wherein the antigen binding site is present on, and formed by, a single immunoglobulin domain. This sets immunoglobulin single variable domains apart from "conventional" immunoglobulins or their fragments, wherein two immunoglobulin domains, in particular two variable domains, interact to form an antigen binding site. Typically, in conventional immunoglobulins, a heavy chain variable domain ($V_H$) and a light chain variable domain ($V_L$) interact to form an antigen binding site. In this case, the complementarity determining regions (CDRs) of both $V_H$ and $V_L$ will contribute to the antigen binding site, i.e. a total of 6 CDRs will be involved in antigen binding site formation.

Preferred ISVDs are depicted in Table A-1, i.e. SEQ ID NOs: 3, 4, 5, 6, 7, 8, 9, 78, 79, 80, 81 and 82, most preferably SEQ ID NOs: 8, 6, 7 and 3.

In view of the above definition, the antigen-binding domain of a conventional 4-chain antibody (such as an IgG, IgM, IgA, IgD or IgE molecule; known in the art) or of a Fab fragment, a F(ab')2 fragment, an Fv fragment such as a disulphide linked Fv or a scFv fragment, or a diabody (all known in the art) derived from such conventional 4-chain antibody, would normally not be regarded as an immunoglobulin single variable domain, as, in these cases, binding to the respective epitope of an antigen would normally not occur by one (single) immunoglobulin domain but by a pair of (associating) immunoglobulin domains such as light and heavy chain variable domains, i.e., by a $V_H$-$V_L$ pair of immunoglobulin domains, which jointly bind to an epitope of the respective antigen.

In contrast, immunoglobulin single variable domains are capable of specifically binding to an epitope of the antigen without pairing with an additional immunoglobulin variable domain. The binding site of an immunoglobulin single variable domain is formed by a single VHH, VH or $V_L$ domain. Hence, the antigen binding site of an immunoglobulin single variable domain is formed by no more than three CDRs.

As such, the single variable domain may be a light chain variable domain sequence (e.g., a $V_L$-sequence) or a suitable fragment thereof; or a heavy chain variable domain sequence (e.g., a $V_H$-sequence or VHH sequence) or a suitable fragment thereof; as long as it is capable of forming a single antigen binding unit (i.e., a functional antigen binding unit that essentially consists of the single variable domain, such that the single antigen binding domain does not need to interact with another variable domain to form a functional antigen binding unit).

In one embodiment of the invention, the immunoglobulin single variable domains are heavy chain variable domain sequences (e.g., a $V_H$-sequence); more specifically, the immunoglobulin single variable domains may be heavy chain variable domain sequences that are derived from a conventional four-chain antibody or heavy chain variable domain sequences that are derived from a heavy chain antibody.

For example, the immunoglobulin single variable domain may be a (single) domain antibody (or an amino acid that is suitable for use as a (single) domain antibody), a "dAb" or dAb (or an amino acid that is suitable for use as a dAb) or a NANOBODY® (as defined herein, and including but not limited to a VHH); other single variable domains, or any suitable fragment of any one thereof.

In particular, the immunoglobulin single variable domain may be a NANOBODY® (as defined herein) or a suitable fragment thereof. [Note: NANOBODY®, NANOBODIES® and NANOCLONE® are registered trademarks of Ablynx N.V.] For a general description of NANOBODIES®, reference is made to the further description below, as well as to the prior art cited herein, such as e.g. described in WO 08/020079 (page 16).

"VHH domains", also known as VHHs, $V_H$H domains, VHH antibody fragments, and VHH antibodies, have originally been described as the antigen binding immunoglobulin (variable) domain of "heavy chain antibodies" (i.e., of "antibodies devoid of light chains"; Hamers-Casterman et al. 1993 Nature 363: 446-448). The term "$V_{HH}$ domain" has been chosen in order to distinguish these variable domains from the heavy chain variable domains that are present in conventional 4-chain antibodies (which are referred to herein as "$V_H$ domains" or "VH domains") and from the light chain variable domains that are present in conventional 4-chain antibodies (which are referred to herein as "$V_L$ domains" or "VL domains"). For a further description of VHH's and NANOBODIES®, reference is made to the review article by Muyldermans (Reviews in Molecular Biotechnology 74: 277-302, 2001), as well as to the following patent applications, which are mentioned as general background art: WO 94/04678, WO 95/04079 and WO 96/34103 of the Vrije Universiteit Brussel; WO 94/25591, WO 99/37681, WO 00/40968, WO 00/43507, WO 00/65057, WO 01/40310, WO 01/44301, EP 1134231 and WO 02/48193 of Unilever; WO 97/49805, WO 01/21817, WO 03/035694, WO 03/054016 and WO 03/055527 of the Vlaams Instituut voor Biotechnologie (VIB); WO 03/050531 of Algonomics N.V. and Ablynx N.V.; WO 01/90190 by the National Research Council of Canada; WO 03/025020 (=EP 1433793) by the Institute of Antibodies; as well as WO 04/041867, WO 04/041862, WO 04/041865, WO 04/041863, WO 04/062551, WO 05/044858, WO 06/40153, WO 06/079372, WO 06/122786, WO 06/122787 and WO 06/122825, by Ablynx N.V. and the further published patent applications by Ablynx N.V. Reference is also made to the further prior art mentioned in these applications, and in particular to the list of references mentioned on pages 41-43 of the International application WO 06/040153, which list and references are incorporated herein by reference. As described in these references, NANOBODIES® (in particular VHH sequences and partially humanized NANOBODIES®) can in particular be characterized by the presence of one or more "Hallmark residues" in one or more of the framework sequences. A further description of the NANOBODIES®, including humanization and/or camelization of NANOBODIES®, as well as other modifications, parts or fragments, derivatives or "Nanobody fusions", multivalent constructs (including some non-limiting examples of linker sequences) and different modifications to increase the half-life of the NANOBODIES® and their preparations may be found e.g. in WO 08/101985 and WO 08/142164. For a further general description of NANOBODIES®, reference is made to the prior art cited herein, such as e.g. described in WO 08/020079 (page 16).

"Domain antibodies", also known as "Dab"s, "Domain Antibodies", and "dAbs" (the terms "Domain Antibodies" and "dAbs" being used as trademarks by the GlaxoSmithKline group of companies) have been described in e.g., EP 0368684, Ward et al. (Nature 341: 544-546, 1989), Holt et al. (Tends in Biotechnology 21: 484-490, 2003) and WO 03/002609 as well as for example WO 04/068820, WO 06/030220, WO 06/003388 and other published patent applications of Domantis Ltd. Domain antibodies essentially correspond to the VH or VL domains of non-camelid mammalians, in particular human 4-chain antibodies. In order to bind an epitope as a single antigen binding domain, i.e., without being paired with a VL or VH domain, respectively, specific selection for such antigen binding properties is required, e.g. by using libraries of human single VH or VL domain sequences. Domain antibodies have, like VHHs, a molecular weight of approximately 13 to approximately 16 kDa and, if derived from fully human sequences, do not require humanization for e.g. therapeutical use in humans.

It should also be noted that, although less preferred in the context of the present invention because they are not of mammalian origin, single variable domains can be derived from certain species of shark (for example, the so-called "IgNAR domains", see for example WO 05/18629).

Thus, in the meaning of the present invention, the term "immunoglobulin single variable domain" or "single variable domain" comprises polypeptides which are derived from a non-human source, preferably a camelid, preferably a camelid heavy chain antibody. They may be humanized, as previously described. Moreover, the term comprises polypeptides derived from non-camelid sources, e.g. mouse or human, which have been "camelized", as e.g., described in Davies and Riechmann (FEBS 339: 285-290, 1994; Biotechnol. 13: 475-479, 1995; Prot. Eng. 9: 531-537, 1996) and Riechmann and Muyldermans (J. Immunol. Methods 231: 25-38, 1999).

The amino acid residues of a VHH domain are numbered according to the general numbering for $V_H$ domains given by Kabat et al. ("Sequence of proteins of immunological interest", US Public Health Services, NIH Bethesda, Md., Publication No. 91), as applied to VHH domains from Camelids, as shown e.g., in FIG. 2 of Riechmann and Muyldermans (J. Immunol. Methods 231: 25-38, 1999). Alternative methods for numbering the amino acid residues of $V_H$ domains, which methods can also be applied in an analogous manner to VHH domains, are known in the art. However, in the present description, claims and figures, the numbering according to Kabat applied to VHH domains as described above will be followed, unless indicated otherwise.

It should be noted that—as is well known in the art for $V_H$ domains and for VHH domains—the total number of amino acid residues in each of the CDRs may vary and may not correspond to the total number of amino acid residues indicated by the Kabat numbering (that is, one or more positions according to the Kabat numbering may not be occupied in the actual sequence, or the actual sequence may contain more amino acid residues than the number allowed for by the Kabat numbering). This means that, generally, the numbering according to Kabat may or may not correspond to the actual numbering of the amino acid residues in the actual sequence. The total number of amino acid residues in a VH domain and a VHH domain will usually be in the range of from 110 to 120, often between 112 and 115. It should however be noted that smaller and longer sequences may also be suitable for the purposes described herein.

Determination of CDR regions may also be done according to different methods. In the CDR determination according to Kabat, FR1 of a VHH comprises the amino acid residues at positions 1-30, CDR1 of a VHH comprises the amino acid residues at positions 31-35, FR2 of a VHH comprises the amino acids at positions 36-49, CDR2 of a VHH comprises the amino acid residues at positions 50-65, FR3 of a VHH comprises the amino acid residues at positions 66-94, CDR3 of a VHH comprises the amino acid residues at positions 95-102, and FR4 of a VHH comprises the amino acid residues at positions 103-113.

In the present application, however, CDR sequences were determined according to Kontermann and Dübel (Eds., Antibody Engineering, vol 2, Springer Verlag Heidelberg Berlin, Martin, Chapter 3, pp. 33-51, 2010). According to this method, FR1 comprises the amino acid residues at positions 1-25, CDR1 comprises the amino acid residues at positions 26-35, FR2 comprises the amino acids at positions 36-49, CDR2 comprises the amino acid residues at positions 50-58, FR3 comprises the amino acid residues at positions 59-94, CDR3 comprises the amino acid residues at positions 95-102, and FR4 comprises the amino acid residues at positions 103-113.

Immunoglobulin single variable domains such as Domain antibodies and NANOBODIES® (including VHH domains) may be subjected to humanization. In particular, humanized immunoglobulin single variable domains, such as NANOBODIES® (including VHH domains) may be immunoglobulin single variable domains that are as generally defined for in the previous paragraphs, but in which at least one amino acid residue is present (and in particular, in at least one of the framework residues) that is and/or that corresponds to a humanizing substitution (as defined herein). Potentially useful humanizing substitutions may be ascertained by comparing the sequence of the framework regions of a naturally occurring $V_{HH}$ sequence with the corresponding framework sequence of one or more closely related human $V_H$ sequences, after which one or more of the potentially useful humanizing substitutions (or combinations thereof) thus determined may be introduced into said $V_{HH}$ sequence (in any manner known per se, as further described herein) and the resulting humanized $V_{HH}$ sequences may be tested for affinity for the target, for stability, for ease and level of expression, and/or for other desired properties. In this way, by means of a limited degree of trial and error, other suitable humanizing substitutions (or suitable combinations thereof) may be determined by the skilled person based on the disclosure herein. Also, based on the foregoing, (the framework regions of) an immunoglobulin single variable domain, such as a NANOBODY® (including VHH domains) may be partially humanized or fully humanized.

Immunoglobulin single variable domains such as Domain antibodies and NANOBODIES® (including VHH domains and humanized VHH domains), can also be subjected to affinity maturation by introducing one or more alterations in the amino acid sequence of one or more CDRs, which alterations result in an improved affinity of the resulting immunoglobulin single variable domain for its respective antigen, as compared to the respective parent molecule. Affinity-matured immunoglobulin single variable domain molecules of the invention may be prepared by methods known in the art, for example, as described by Marks et al. (Biotechnology 10:779-783, 1992), Barbas, et al. (Proc. Nat. Acad. Sci, USA 91: 3809-3813, 1994), Shier et al. (Gene 169: 147-155, 1995), Yelton et al. (Immunol. 155: 1994-2004, 1995), Jackson et al. (J. Immunol. 154: 3310-9, 1995), Hawkins et al. (J. Mol. Biol. 226: 889 896, 1992), Johnson and Hawkins (Affinity maturation of antibodies using phage display, Oxford University Press, 1996).

The process of designing/selecting and/or preparing a polypeptide, starting from an immunoglobulin single variable domain such as an, $V_H$, $V_L$, $V_{HH}$, Domain antibody or a NANOBODY®, is also referred to herein as "formatting" said immunoglobulin single variable domain; and an immunoglobulin single variable domain that is made part of a polypeptide is said to be "formatted" or to be "in the format of" said polypeptide. Examples of ways in which an immunoglobulin single variable domain may be formatted and examples of such formats will be clear to the skilled person based on the disclosure herein; and such formatted immunoglobulin single variable domain form a further aspect of the invention.

For example, and without limitation, one or more immunoglobulin single variable domains may be used as a "binding unit", "binding domain" or "building block" (these terms are used interchangeably herein) for the preparation of a polypeptide, which may optionally contain one or more further immunoglobulin single variable domains that can serve as a binding unit (i.e., against the same or another epitope on CD40L and/or against one or more other antigens, proteins or targets than CD40L).

Monovalent polypeptides comprise or essentially consist of only one binding unit (such as e.g., immunoglobulin single variable domains). Polypeptides that comprise two or more binding units (such as e.g., immunoglobulin single variable domains) will also be referred to herein as "multivalent" polypeptides, and the binding units/immunoglobulin single variable domains present in such polypeptides will also be referred to herein as being in a "multivalent format". For example a "bivalent" polypeptide may comprise two immunoglobulin single variable domains, optionally linked via a linker sequence, whereas a "trivalent" polypeptide may comprise three immunoglobulin single variable domains, optionally linked via two linker sequences; whereas a "tetravalent" polypeptide may comprise four immunoglobulin single variable domains, optionally linked via three linker sequences, etc.

In a multivalent polypeptide, the two or more immunoglobulin single variable domains may be the same or different, and may be directed against the same antigen or antigenic determinant (for example against the same part(s) or epitope(s) or against different parts or epitopes) or may alternatively be directed against different antigens or antigenic determinants; or any suitable combination thereof. Polypeptides that contain at least two binding units (such as e.g., immunoglobulin single variable domains) in which at least one binding unit is directed against a first antigen (i.e., CD40L) and at least one binding unit is directed against a second antigen (i.e., different from CD40L) will also be referred to as "multispecific" polypeptides, and the binding units (such as e.g., immunoglobulin single variable domains) present in such polypeptides will also be referred to herein as being in a "multispecific format". Thus, for example, a "bispecific" polypeptide of the invention is a polypeptide that comprises at least one immunoglobulin single variable domain directed against a first antigen (i.e., CD40L) and at least one further immunoglobulin single variable domain directed against a second antigen (i.e., different from CD40L), whereas a "trispecific" polypeptide of the invention is a polypeptide that comprises at least one immunoglobulin single variable domain directed against a first antigen (i.e., CD40L), at least one further immunoglobulin single variable domain directed against a second antigen (i.e., different from CD40L) and at least one further immunoglobulin single variable domain directed against a third antigen (i.e., different from both CD40L and the second antigen); etc.

"Multiparatopic polypeptides", such as e.g., "biparatopic polypeptides" or "triparatopic polypeptides", comprise or essentially consist of two or more binding units that each have a different paratope.

Preferably, the polypeptide of the invention is a bispecific polypeptide comprising a first ISVD (e.g. an ISVD binding CD40L) and a second ISVD (e.g. an ISVD binding serum albumin).

A means to improve the efficacy of a therapeutic antibody is to increase its serum persistence, thereby allowing higher circulating levels, less frequent administration and reduced doses.

In the art, groups or moieties have been described that extend the half-life of a molecule in vivo, such as PEG groups of Fc regions.

However, the Fc region of an antibody not only mediates its serum half-life, but also effector functions, such as complement-dependent cytotoxicity (CDC), antibody-dependent cellular cytotoxicity (ADCC) and antibody-dependent cell phagocytosis (ADCP), which have a negative impact on safety.

However, as mentioned before, a recent finding demonstrated a 22-25% occurrence of anti-PEG antibodies in healthy blood donors. This development of anti-PEG antibodies, which may limit efficacy in some patients, is contrary to the general assumption that PEG is non-immunogenic. Hence, PEGylated therapeutic agents have potential implications for clinical use, especially in an immune-compromised disease setting. Moreover, it was reported that PEGylation of the anti-CD40L Fab' molecule decreased its activity by 4-5 fold (US2010/0104573).

The present inventors were able to re-engineer the ISVDs to not only outperform the benchmark CDP7657 but to also retain this performance upon half-life extension. In a specific, but non-limiting aspect of the invention, which will be further described herein, the polypeptides of the invention have an increased half-life in serum (as further described herein) compared to the immunoglobulin single variable domain binding CD40L.

The "half-life" of a polypeptide of the invention can generally be defined as described in paragraph o) on page 57 of WO 08/020079 and as mentioned therein refers to the time taken for the serum concentration of the polypeptide to be reduced by 50%, in vivo, for example due to degradation of the polypeptide and/or clearance or sequestration of the polypeptide by natural mechanisms. The in vivo half-life of a polypeptide of the invention may be determined in any manner known per se, such as by pharmacokinetic analysis. Suitable techniques will be clear to the person skilled in the art, and may for example generally be as described in paragraph o) on page 57 of WO 08/020079. As also mentioned in paragraph o) on page 57 of WO 08/020079, the half-life may be expressed using parameters such as the $t\frac{1}{2}$-α, $t\frac{1}{2}$-β and the area under the curve (AUC). Reference is for example made to the standard handbooks, such as Kenneth et al. (Chemical Stability of Pharmaceuticals: A Handbook for Pharmacists, John Wiley & Sons Inc, 1986) and Gibaldi & Perron ("Pharmacokinetics", Marcel Dekker, $2^{nd}$ Rev. Edition, 1982). The terms "increase in half-life" or "increased half-life" are also as defined in paragraph o) on page 57 of WO 08/020079 and in particular refer to an increase in the $t\frac{1}{2}$-β, either with or without an increase in the $t\frac{1}{2}$-α and/or the AUC or both.

In a specific aspect of the invention, a polypeptide of the invention has an increased half-life, compared to the corresponding polypeptide lacking an ISVD binding serum protein. Some preferred, but non-limiting examples of such polypeptides will become clear to the skilled person based on the further disclosure herein, and for example comprise polypeptides of the invention that comprise immunoglobulin single variable domains binding to a serum protein (such as serum albumin); or polypeptides of the invention which comprise at least one amino acid sequence of the invention that is linked to at least one moiety (and in particular at least one amino acid sequence) which increases the half-life of the amino acid sequence of the invention. Examples of polypeptides of the invention which comprise such half-life extending moieties or immunoglobulin single variable domains will become clear to the skilled person based on the further disclosure herein; and for example include, without limitation, polypeptides in which the one or more immunoglobulin single variable domains of the invention are suitably linked to one or more serum proteins or fragments thereof (such as (human) serum albumin or suitable fragments thereof) or to one or more binding units that can bind to serum proteins (such as, for example, ISVDs, domain antibodies, single domain antibodies, "dAb"'s, or NANOBODIES® that can bind to serum proteins such as serum albumin (such as human serum albumin), serum immunoglobulins such as IgG, or transferrin; reference is made to the further description and references mentioned herein); polypeptides of the invention comprising one or more small proteins or peptides that can bind to serum proteins, such as, without limitation, the proteins and peptides described in WO 91/01743, WO 01/45746, WO 02/076489, WO2008/068280, WO2009/127691 and PCT/EP2011/051559.

Generally, the compounds or polypeptides of the invention with increased half-life preferably have a half-life that is at least 1.5 times, preferably at least 2 times, such as at least 5 times, for example at least 10 times or more than 20 times, greater than the half-life of the corresponding amino acid sequence of the invention, e.g. the ISVD binding CD40L per se (without the ISVD binding serum albumin). For example, the compounds or polypeptides of the invention with increased half-life may have a half-life e.g., in humans that is increased with more than 1 hours, preferably more than 2 hours, more preferably more than 6 hours, such as more than 12 hours, or even more than 24, 48 or 72 hours, compared to the corresponding amino acid sequence of the invention, e.g. ISVD binding CD40L per se.

In a preferred, but non-limiting aspect of the invention, such compounds or polypeptides of the invention have a serum half-life, e.g. in humans that is increased with more than 1 hours, preferably more than 2 hours, more preferably more than 6 hours, such as more than 12 hours, or even more than 24, 48 or 72 hours, compared to the corresponding amino acid sequence of the invention, e.g. ISVD binding CD40L per se.

In another preferred, but non-limiting aspect of the invention, such compounds or polypeptides of the invention exhibit a serum half-life in human of at least about 12 hours, preferably at least 24 hours, more preferably at least 48 hours, even more preferably at least 72 hours or more. For example, compounds or polypeptides of the invention may have a half-life of at least 5 days (such as about 5 to 10 days), preferably at least 9 days (such as about 9 to 14 days), more preferably at least about 10 days (such as about 10 to 15 days), or at least about 11 days (such as about 11 to 16 days), more preferably at least about 12 days (such as about 12 to 18 days or more), or more than 14 days (such as about 14 to 19 days).

In a preferred aspect, the present invention also relates to a polypeptide as described herein, wherein said ISVD binding serum albumin essentially consists of 4 framework regions (FR1 to FR4, respectively) and 3 complementarity determining regions (CDR1 to CDR3 respectively), in which CDR1 is SEQ ID NO: 74, CDR2 is SEQ ID NO: 75 CDR1 is SEQ ID NO: 76 (see Table A-3).

In a particularly preferred but non-limiting aspect of the invention, the invention provides a polypeptide of the invention comprising at least one immunoglobulin single variable domain (ISVD) that specifically binds to CD40L and at least one ISVD binding serum albumin, e.g. ISVD binding serum albumin is chosen from the group consisting of ALB135 (SEQ ID NO: 15), ALB129 (SEQ ID NO: 13), ALB8 (SEQ ID NO: 11), ALB23 (SEQ ID NO: 12), and ALB132 (SEQ ID NO: 14), preferably SEQ ID NO: 15.

Immune responses to therapeutic protein products may pose problems for both patient safety and product efficacy. Thromboembolic events may also be due to pre-existing antibodies (PEAs) and/or anti-drug antibodies (ADAs) against a therapeutic protein. In this regard, immunogenicity is the propensity of the therapeutic protein product to generate immune responses to itself and to related proteins or to induce immunologically related adverse clinical events.

The present inventors were able to engineer polypeptides that were significantly safer than the prior art antibodies.

In the research leading up to the present invention, after having established that adding C-terminal extension (which may be as simple as a single C-terminal alanine residue, see again WO 12/175741, Example 3) to the C-terminal region or end of an ISVD essentially prevents/removes binding of pre-existing antibodies/factors in most samples of human subjects/patients, it was investigated whether samples obtained from human subjects (healthy volunteers and/or subjects suffering from a disease or disorder) possibly contain (other) pre-existing antibodies or factors that can bind to the exposed C-terminal region of a NANOBODY® (or other ISVD) even when a C-terminal extension is present. In doing so, the present inventors have found that, although essentially no such pre-existing antibodies binding to a C-terminally extended ISVD may be found in the blood or serum of healthy volunteers or in blood or serum obtained from human patients suffering from one of a number of different diseases (including some inflammatory diseases or auto-immune disorders—data not shown), some blood or serum samples that have been obtained from certain (but not all) human subjects suffering from certain severe (auto-) immune disorders (such as SLE) appear to contain some pre-existing antibodies/factors that can bind to ISVDs even when said ISVDs comprise a C-terminal extension.

The present inventors set out to provide improved ISVDs, which, when they have an exposed C-terminal region or end, are less prone to binding by pre-existing antibodies/factors, such as those that are found in blood or serum samples obtained from human subjects suffering from certain (auto-) immune diseases or disorders that severely impact/activate the immune system (such as SLE).

It was found that the binding of pre-existing antibodies/factors to an ISVD with an exposed C-terminal end may be (further) reduced by a mutation of the serine at position 112 (Kabat numbering) to either lysine (K) or glutamine (Q). In particular, it has been found that such an S112K or S112Q mutation can (further) reduce or essentially prevent/remove binding of pre-existing antibodies/factors that can bind to an ISVD that comprises a C-terminal extension (but no S112K or S112Q mutation), such as those pre-existing antibodies/factors that are found in the blood or serum of human subjects suffering from severe auto-immune disorders such as SLE.

This finding is broadly applicable.

The immunoglobulins (and in particular immunoglobulin single variable domains) of the invention may also contain the specific mutations/amino acid residues described in the following co-pending US provisional applications, all entitled "Improved immunoglobulin variable domains": U.S. 61/994,552 filed May 16, 2014; U.S. 61/014,015 filed Jun. 18, 2014; U.S. 62/040,167 filed Aug. 21, 2014; and U.S. 62/047,560, filed Sep. 8, 2014 (all assigned to Ablynx N.V.).

In particular, the present invention relates to a polypeptide as described herein, comprising an ISVD, preferably a C-terminally located ISVD, even more preferably said C-terminally located ISVD is an ISVD binding serum albumin, in which: (i) the amino acid residue at position 112 is one of K or Q; and/or (ii) the amino acid residue at position 89 is T; and/or (iii) the amino acid residue at position 89 is L and the amino acid residue at position 110 is one of K or Q; and (iv) in each of cases (i) to (iii), the amino acid at position 11 is preferably V; and in which said VH domain contains a C-terminal extension (X)n, in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I).

Accordingly, the present invention relates to a polypeptide as described herein, comprising an ISVD, preferably a C-terminally located ISVD, even more preferably said C-terminally located ISVD is an ISVD binding serum albumin, in which:

the amino acid residue at position 11 is one of L, V or K; and
the amino acid residue at position 14 is one of A or P; and
the amino acid residue at position 41 is one of A or P; and
the amino acid residue at position 89 is one of T, V or L; and
the amino acid residue at position 108 is one of Q or L; and
the amino acid residue at position 110 is one of T, K or Q; and
the amino acid residue at position 112 is one of S, K or Q;
in which either (i) the amino acid residue at position 112 is one of K or Q; and/or (ii) the amino acid residue at position 89 is T; and/or (iii) the amino acid residue at position 89 is L and the amino acid residue at position 110 is one of K or Q; and (iv) in each of cases (i) to (iii), the amino acid at position 11 is preferably V.

As mentioned in said co-pending US provisional applications, said mutations are effective in preventing or reducing binding of so-called "pre-existing antibodies" to the immunoglobulins and compounds of the invention. For this purpose, the immunoglobulins of the invention may also contain (optionally in combination with said mutations) a C-terminal extension (X)n (in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I)), for which reference is again made to said US provisional applications as well as to WO 12/175741. In particular, an immunoglobulin of the invention may contain such a C-terminal extension when it forms the C-terminal end of a protein, polypeptide or other compound or construct comprising the same (again, as further described in said US provisional applications as well as WO 12/175741).

Accordingly, the present invention relates to a polypeptide comprising at least one ISVD that specifically binds to CD40L and further comprises an ISVD binding serum albumin, wherein said ISVD binding serum albumin is chosen from Alb00129 (Alb11(L11V,V89T)-A) (SEQ ID NO: 13) and Alb00132 (Alb23 (L5V,L11V,V89T)-A) (SEQ ID NO: 14) and ALB11(S112K)-A (SEQ ID NO: 15). Preferably, the polypeptide of the invention is SEQ ID NO: 9.

The present invention further relates to a pharmaceutical composition comprising a polypeptide of the invention. It is also possible that the pharmaceutical composition comprises a nucleic acid encoding said polypeptide of the invention, a vector or vector system containing said nucleic acid and/or a preferably human cell producing said polypeptide of the invention. Optionally, the pharmaceutical composition comprises pharmaceutically acceptable excipients, adjuvants and/or carriers.

As exemplary excipients, disintegrators, binders, fillers, and lubricants may be mentioned. Examples of disintegrators include agar-agar, algins, calcium carbonate, cellulose, colloid silicon dioxide, gums, magnesium aluminium silicate, methylcellulose, and starch. Examples of binders include micro-crystalline cellulose, hydroxymethyl cellulose, hydroxypropylcellulose, and polyvinylpyrrolidone. Examples of fillers include calcium carbonate, calcium phosphate, tribasic calcium sulfate, calcium carboxymethylcellulose, cellulose, dextrin, dextrose, fructose, lactitol, lactose, magnesium carbonate, magnesium oxide, maltitol, maltodextrins, maltose, sorbitol, starch, sucrose, sugar, and xylitol. Examples of lubricants include agar, ethyl oleate, ethyl laureate, glycerin, glyceryl palmitostearate, hydrogenated vegetable oil, magnesium oxide, stearates, mannitol, poloxamer, glycols, sodium benzoate, sodium lauryl sulfate, sodium stearyl, sorbitol, and talc. Usual stabilizers, preservatives, wetting and emulsifying agents, consistency-improving agents, flavour-improving agents, salts for varying the osmotic pressure, buffer substances, solubilizers, diluents, emollients, colorants and masking agents and antioxidants come into consideration as pharmaceutical adjuvants.

Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting-point wax, cocoa butter, water, alcohols, polyols, glycerol, vegetable oils and the like.

The pharmaceutical composition may also comprise at least one further active agent, e.g. one or more further antibodies or antigen-binding fragments thereof, peptides, proteins, nucleic acids, organic and inorganic molecules.

In a preferred embodiment of the invention, the pharmaceutical compositions comprising a polypeptide of the invention are for use in medicine or diagnostics. Preferably, the pharmaceutical compositions are for use in human medicine, but they may also be used for veterinary purposes.

In particular, the polypeptide of the invention, the nucleic acids, the vector or vector system, the host or host cell of the invention, or a pharmaceutical composition comprising a polypeptide of the invention are for use in the diagnosis, prevention or treatment of disorders associated with, caused by or accompanied by elevated levels and/or activity of CD40L, and other diseases or conditions which may be beneficially diagnosed, prevented, or treated by inhibiting and/or neutralizing CD40L activity via the administration of a polypeptide of the invention as described supra. In a further embodiment, the present invention relates to methods for the diagnosis, prevention or treatment of disorders associated with, caused by or accompanied by elevated levels and/or activity of CD40L, and other diseases or conditions which may be beneficially diagnosed, prevented, or treated by inhibiting and/or neutralizing CD40L activity.

In an embodiment, the present invention relates to a polypeptide of the invention for use as a medicament.

In a further embodiment, the present invention relates to a polypeptide of the invention for use in treating or preventing a symptom of an autoimmune disease, Systemic Lupus Erythematosus (SLE), Lupus Nephritis, Immune Thrombocytopenic Purpura (ITP), transplant rejection, Crohn's Disease, Sjögren's Syndrome, Inflammatory Bowel Disease (IBD), colitis, asthma/allergy, atherosclerosis, Myasthenia Gravis, Multiple Sclerosis, Psoriasis, Rheumatoid Arthritis, Ankylosing Spondylitis, Coronary Heart Disease, Type 1 Diabetes and/or immune response to recombinant drug products, e.g., factor VII in hemophilia.

In an embodiment, the present invention relates to a method of treating prevention of diseases or disorders in an individual, for instance in which inappropriate activation of a CD40L/CD40-mediated pathway is involved, the method comprising administering the polypeptide of the invention to said individual in an amount effective to treat or prevent a symptom of said disease or disorder. Preferred medical indications are autoimmune or inflammatory diseases or conditions associated with elevated levels and/or activity of CD40L. The disease or condition may be selected from, for example, Systemic Lupus Erythematosus (SLE), Lupus Nephritis, Immune Thrombocytopenic Purpura (ITP), transplant rejection, Crohn's Disease, Inflammatory Bowel Disease (IBD), colitis, asthma/allergy, atherosclerosis, Myasthenia Gravis, Multiple Sclerosis, Psoriasis, Rheumatoid Arthritis, Ankylosing Spondylitis, Sjögren's Syndrome, Coronary Heart Disease, Type 1 Diabetes, amyotrophic lateral sclerosis (ALS; also known as Lou Gehrig's disease and Charcot disease) and immune response to recombinant drug products, e.g., factor VII in hemophilia. Particularly preferred indications are ITP, SLE and Lupus Nephritis.

A polypeptide of the invention or a pharmaceutical composition according to the invention may be administered to a subject in need thereof in an amount effective to obtain the desired therapeutic or prophylactic effect. For example, one desired effect to be achieved by said administration may be to block, inhibit and/or neutralize one or more biological function(s) of CD40L. In this context, administration may comprise contacting the polypeptide of the invention with cells or a tissue suspected of expressing CD40L, preferably at high and/or aberrant levels, under conditions, wherein the polypeptide is capable of blocking, inhibiting and/or neutralizing CD40L function. The contacting may be in vitro or in vivo.

Administration of suitable compositions may be effected in different ways, e.g., by intravenous, intraperitoneal, subcutaneous, intramuscular, topical, oral, intradermal, intranasal or intrabronchial administration. Administration may also be conducted directly at the target site.

The dosage regimen will be determined by the attending physician and clinical factors. As is well known in the medical arts, dosage for any one patient depends upon many factors, including the patient's size, weight, body surface area, age, the particular compound to be administered, the activity of the employed polypeptide (including antibodies), time and route of administration, general health, and combination with other therapies or treatments. Proteinaceous pharmaceutically active matter may be present in amounts between 1 g and 100 mg/kg body weight per dose; however, doses below or above this exemplary range are also envisioned. If the regimen is a continuous infusion, it may be in the range of 1 pg to 100 mg per kilogram of body weight per minute.

A neutralizing polypeptide of the invention may be employed at a concentration of, e.g., 0.01, 0.1, 0.5, 1, 2, 5, 10, 20 or 50 pg/ml in order to inhibit and/or neutralize a biological function of CD40L by at least about 50%, preferably 75%, more preferably 90%, 95% or up to 99%, and most preferably approximately 100% (essentially completely) as assayed by methods well known in the art.

According to further aspects of the invention, the polypeptide of the invention may be used in additional applications in vivo and in vitro. For example, polypeptides of the invention may be employed for diagnostic purposes, e.g. in assays designed to detect and/or quantify the presence of CD40L and/or to purify CD40L. Polypeptides may also be tested in animal models of particular diseases and for conducting toxicology, safety and dosage studies.

Finally, the invention relates to a kit comprising at least one polypeptide according to the invention, at least one nucleic acid sequence encoding said components, the vector or vector system of the invention, and/or a host cell according to the invention. It is contemplated that the kit may be offered in different forms, e.g. as a diagnostic kit.

The invention may be better understood based on the Examples that follow. However, one of skilled in the art will readily appreciate that the specific methods and results discussed are merely to be illustrative of the invention as described herein.

6 EXAMPLES

The following examples illustrate the methods and products of the invention. Suitable modifications and adaptations of the described conditions and parameters normally encountered in the art of molecular and cellular biology that are apparent to those skilled in the art are within the spirit and scope of the present invention.

6.1 Materials and Methods

6.1.1 Flow Cytometry (Binding)

Periplasmic extracts were analyzed via FACS for binding to human CD40L. $2\times10^5$ cells (stable CHO-K1/human CD40L transfected cells) were incubated with a 1/10 dilution of periplasmic extracts in FACS buffer (PBS, 10% fetal bovine serum (Sigma, F7524), 0.05% Na-azide) for 30 minutes at 4° C. Cells were then washed three times in FACS buffer and finally resuspended in FACS buffer containing Phycolink a-FLAG®-RPE (Prozyme, PJ315). This mixture was incubated for 30 minutes at 4° C. Cells were washed again three times in FACS buffer and dead cells were stained with TOPRO3 (Molecular probes, T3605). Samples were analyzed on a FACSARRAY® (BD Biosciences).

6.1.2 ALPHASCREEN® (Blocking)

In order to determine the CD40L/CD40 interaction blocking capacity of the NANOBODIES®, periplasmic extracts were screened in protein-based competition assays using the ALPHASCREEN® technology. In short, biotinylated human CD40L (HEK, R&D) was captured on the Donor beads and human CD40-Fc chimera was captured on anti-human Fc NANOBODY® coated Acceptor beads. To evaluate the blocking capacity of anti-CD40L NANOBODIES®, dilutions of the periplasmic extracts were pre-incubated with biotinylated CD40L. To this mixture, CD40-Fc, Acceptor beads and the streptavidin-coupled Donor beads were added and further incubated for 1 hour at room temperature. Fluorescence was measured using the EnVision Multilabel Plate Reader, using an excitation wavelength of 680 nm and an emission wavelength of 520 nm. Decrease in the ALPHASCREEN® signal indicates that the binding of biotinylated CD40L to the CD40 receptor is blocked by the NANOBODY® present in the periplasmic extract.

6.1.3 SPR (Off-Rates)

All off-rates were determined on a ProteOn XPR36 instrument (Bio-Rad Laboratories, Inc.). ProteOn GLC Sensor Chips were coated with 1200-1800 RU of recombinant human CD40L (R&D HEK) in 10 mM acetate buffer pH5.5 via amine coupling using EDC (1-Ethyl-3-[3-dimethyl-aminopropyl] carbodiimide hydrochloride) and sulfo-NHS (N-hydroxysuccinimide). 10-fold diluted periplasmic extracts of anti-CD40L NANOBODIES® expressing E. coli clones in running buffer ProteOn PBS/Tween (phosphate buffered saline, pH7.4 with 0.005% Tween 20) were flown over the sensor chips. Purified monovalent anti-CD40L NANOBODIES® were flown over the sensor chips at 100 nM. For affinity maturation (see Example 6.8.) experiments were carried out at 37° C., all other experiments were carried out at 25° C. Data obtained was double referenced by Interspot subtraction as well as subtraction of a blank buffer injection. Processed curves were used for off-rate analysis based on the Langmuir dissociation model.

6.1.4 Reporter Assay

In this assay, the effect of NANOBODIES® on inhibition of CD40L-induced CD40-signaling is quantified via an NF-κB-SEAP reporter system. By introduction of an NF-κB-inducible SEAP construct via stable transfection of HEK293T cells, ligand induction triggers the secretion of embryonic alkaline phosphatase. The SEAP construct consists of the SEAP reporter gene under the control of the IFN-6 minimal promoter fused to five NF-κB binding sites (InvivoGen, TDS HEK-Blue™ CD40L Cells, cat. Hkb-cd40).

Dilution series of NANO BODIES® were incubated for 16 h at 37° C. and 5% $CO_2$ in a wet chamber with membrane extracts of CHO hCD40L 4B11 cells and $5\times10^4$ HEK-Blue cells in assay medium (DMEM (Invitrogen, Cat 31966-021)+10% FBS (Sigma, Cat F7524)+1% Pen/Step (Invitrogen, Cat 15140-122)). Subsequently, a part of the suspension was added to the substrate and incubated for 1 h at room temperature. The SEAP levels were determined using the Envision (620 nm) (Perkin Elmer).

6.1.5 B-Cell Activation Assay

Dilution series of NANOBODIES® were incubated for 5 days at 37° C. and 5% CO2 in a wet chamber with irradiated $1\times10^4$ CHO hCD40L 4B11 cells and $5\times10^4$ B-cells in assay medium (RPMI-1640 (Invitrogen, Cat 72400-054)+10% FBS (Sigma, Cat F7524)+1% Pen/Step (Invitrogen, Cat 15140-122)). On the fifth day the plate was centrifuged for 5 minutes, 250 g at 4° C. Cells were then resuspended in antibody dilution (Mouse anti-human CD19-FITC (BD Pharmingen, cat.: 555412)+Mouse anti-human CD86-PE (BD Pharmingen, cat.: 555658)) and placed at 4° C. for 30 minutes. Afterwards cells were washed 3 times with MACS buffer and then resuspended in MACS buffer containing 1/1000 diluted TOPRO3 (Molecular Probes T3605). Samples were analyzed on the FACSCanto II.

6.1.6 B-Cell Proliferation Assay

Dilution series of NANO BODIES® were incubated for 4 days at 37° C. and 5% $CO_2$ in a wet chamber with membrane extracts of CHO hCD40L 4B11 cells and $5\times10^4$ B-cells in assay medium (RPMI-1640 (Invitrogen, Cat 72400-054)+10% FBS (Sigma, Cat F7524)+1% Pen/Step (Invitrogen, Cat 15140-122)). On the fourth day, Tritium-thymidine (Perkin Elmer, ref: NET027X001MC) was added to the plates. The plates were frozen after a 24 h incubation period with Tritium-thymidine. The following day, the plate was harvested and analyzed on the Top count (Perkin Elmer) ($H^3$ thymidine uptake assay).

6.1.7 Competition ELISA

To evaluate if the NANOBODIES® recognised different epitopes on the CD40L protein, purified NANOBODIES® were binned against a smaller set of NANOBODIES® displayed on phage in a competition ELISA. Each well of a 96-well F bottom plate Nunc-Immuno™ (NUNC) was incubated overnight at 4° C. with 50 ng of hCD40L (produced in HEK cells, R&D, cat #: 6420-CL/CF) protein in PBS. After blocking with 4% (w/v) skimmed-milk for 1 h at RT, NANOBODY®-phage were added in the presence or absence of 0.5 µM purified NANOBODY®. Bound NANOBODY®-phage were detected with anti-M13-HRP MAb (GE Healthcare; cat #27-9421-01) and colorimetric detection at 450 nm was performed using soluble (High Sensitivity) tetramethylbenzidine Substrate (es(HS)TMB) (SDT) as HRP substrate. The ratio between the absorbance at 450 nm in the presence and absence of purified NANOBODY® was used to determine if the binned NANOBODIES® recognised the same or (non-) overlapping epitopes on the CD40L molecule.

6.2 NANOBODY® Identification

In view of triggering an immune response against CD40L in llama, the homology across different species was assessed by calculating the percentage of identity and number of different residues of aligned sequences of CD40L of different species, but considering only the extracellular domain. The percentage identity with human CD40L ranged from 99.5% for rhesus monkey to 88% for llama and less than 75% for mouse and rat. The high homology of human CD40L (hCD40L) with llama CD40L confounds antibody generation. The low homology of human CD40L with rat and mouse CD40L complicates the finding of cross-reactive NANOBODIES®.

Five outbred llamas were immunized. Two llamas were immunized with recombinant human CD40L (PeproTech, 310-02). Three llamas were immunized with Llana cells expressing hCD40L. Notwithstanding the high homology between hCD40L and llama CD40L, all llamas showed a strong immune response against hCD40L.

Immune NANOBODY® phage display libraries were generated from cDNA prepared using total RNA extracted from blood samples of all llamas. The phage display libraries were probed using either recombinant human CD40L, human CD40L expressed on human cells or both antigen formats alternating between selection rounds.

Selection outputs were screened for NANOBODY® binding via FACS and for blocking in an ALPHASCREEN® competition assay according to Examples 6.1.1 and 6.1.2 above.

After one selection round, about 50% of the binding NANOBODIES® were also blocking the CD40L/CD40 interaction. The number of FACS binders and the fraction of blocking NANOBODIES® increased with selection rounds, except for NANOBODIES® selected on recombinant hCD40L produced in E. coli. Higher hit rates were observed for clones originating from animals immunized with CHO-CD40L cells.

More than 1500 NANOBODY® hits meeting the cut-off criteria in FACS and ALPHASCREEN® were subsequently sequenced, resulting in 689 unique clones belonging to 210 different NANOBODY® families. The off-rates of these clones were determined as set out in Example 6.1.3.

40 different NANOBODY® clones were selected for further characterization, i.e. the lead panel. Only clones which blocked the CD40/CD40L interaction in ALPHASCREEN®, which bound to the native conformation of CD40L (FACS) and which had an off-rate $<4\times10^{-3}$, were considered further.

6.3 In Vitro Characterization of the Lead Panel of 40 NANOBODIES®

The 40 NANOBODIES® of the lead panel were cloned into pAX205, produced in P. pastoris and purified for further characterization. Their potencies were determined via ALPHASCREEN® and in reporter- and B-cell activation assays (see Examples 6.1.4 and 6.1.5). In addition, the off-rates were confirmed. Epitope bins were determined by screening purified NANOBODIES® against NANOBODIES® displayed on phage in a competition ELISA (see Example 6.1.7).

7 different epitope bins were identified within the lead panel of 40 NANOBODIES®. NANOBODIES® C01000281302 (bin 6.2) and C01000461303 (bin 2.1) are in different epitope bins than CDP7657 (bin 1.1). The most potent clones belonged to epitope bin 6.2.

In view of the sequence conservation between human and llama CD40L, it was not expected that NANOBODIES® would be identified belonging to 7 different epitope bins.

6.4 Further In Vitro Selection of the Lead Panel of 15 NANOBODIES®

An important phenotype that is induced by the CD40L-CD40 interaction is B-cell activation and proliferation. The B-cell can present antigens to helper T-cells. If an activated T-cell recognizes the peptide presented by the B-cell, CD40L on the T-cell binds to the B-cell its CD40 receptor, causing resting B-cell activation. The T-cell also produces IL-4, which directly influences B-cells. As a result of these stimulations, the B-cell can undergo division.

15 NANOBODIES®, selected based on sequence diversity and their performance in the B-cell activation assay, were tested in a B-cell proliferation assay according to Example 6.1.6. The main difference between the B-cell activation and proliferation assay is the readout (being determination of CD86 levels and $H^3$ thymidine uptake, respectively) and the CD40L source used to activate the B-cells (UV-irradiated hCD40L expressing CHO cells and membrane extracts from hCD40L cells, respectively). For both assays the B-cells originated from healthy donors. $H^3$ thymidine uptake is a further downstream indicator of B-cell activation than CD86 expression and thus considered the more relevant functional readout. In the B-cell proliferation assay 6 out of the 15 clones were found to have potencies comparable to CDP7657 Fab.

6.5 Selection of 4 Lead Candidates

Based on the ALPHASCREEN®, reporter assay, B-cell activation assay and B-cell proliferation assay as set out above and physico-chemical stability data (data not shown), the lead panel was reduced to 4 lead candidates for the final characterization stage. From the most potent epitope bin (bin 6.2; see above), two lead candidates from different families were selected: C01000281302 ("28602") and C01000441307 ("44B07"). Although C01000281302 was one of the best clones in the B-cell proliferation assay, C01000441307 was the most potent clone in the B-cell activation assay and a very potent clone in the B-cell proliferation assay. Two additional lead candidates were selected. C0100029C10 ("29C10") of epitope bin 4.2, which was also a potent clone in the B-cell proliferation assay. Notwithstanding the above criteria, indicating that at least 9 clones performed better in various assays, the present inventors decided to select C01000461303 ("46B03") of epitope bin 2.1 as well, since it represented a different germline.

6.6 Formatting: Effect of Half-Life Extension (HLE)

Treatment of autoimmune diseases typically requires drugs to have a sustained availability in the patient, i.e. the drug should have a long half-life. Various means of half-life extension of drugs are available, including Fc-fusions, PEGylation and fusion to serum albumin and albumin-binders.

It was hypothesized that Fc-fusion is the least preferred option, since this would enable binding to the Fc Receptors present on human platelets, potentially resulting in platelet activation and aggregation. Moreover, PEGylation is not preferred since the PEG moiety is conjugated to the NANOBODY® in a separate production step, resulting in increased costs and decreased yields. Also, PEGylation often leads to a reduced binding affinity due to steric interference with the drug-target binding interaction and suffers from high PEAs. In view hereof, it was opted for half-life extension by fusion to an ISVD binding serum albumin.

In order to assess the influence of albumin binding on the lead candidates, half-life extended (HLE) (NB-35GS-Alb11-FLAG3-HIS6) and non-HLE monovalent ISVDs were constructed and tested in the B-cell proliferation assay in the absence and presence of human serum albumin (HSA) as indicated by $IC_{50}$:

C010000006 is C01000281302-Alb11-FLAG3-HIS6;
C010000008 is C01000029C10-Alb11-FLAG3-HIS6;
C010000004 is C010000441307-Alb11-FLAG3-HIS6; and
C010000010 is C010000461303-Alb11-FLAG3-HIS6.

The results are depicted in Table 6.6.

TABLE 6.6

Influence of fusion of half-life extension ISVD and HSA-binding on the potency of the lead NANOBODIES ® in the B-cell proliferation assay

| construct | IC50 (M) -HSA | IC50 (M) +HSA | fold diff -HSA | fold diff +HSA |
|---|---|---|---|---|
| C010000006 | 5.97E−10 | 1.33E−09 | 1 | 2.2 |
| C0100028B02 | | 2.81E−09 | | |
| C010000008 | 1.26E−09 | 2.06E−09 | 1 | 1.6 |
| C0100029C10 | | 1.06E−09 | | |
| C010000004 | 1.18E−09 | 1.88E−09 | 1 | 1.6 |
| C0100044B07 | | 1.14E−09 | | |
| C010000010 | 8.52E−10 | 1.72E−09 | 1 | 2 |
| C0100046B03 | | 2.38E−09 | | |

Only small differences in potency were observed, indicating a limited impact of half-life extension on the potencies of the molecules. In contrast to CDP7657 for which half-life extension of the Fab' moiety by PEGylation decreased activity by 4-5 fold (cf. US2010/0104573).

6.7 Species Cross-Reactivity and Selectivity 6.7.1 Species Cross-Reactivity

Considering different degrees of CD40L sequence homology with human CD40L, ranging from 99.5% for rhesus monkey to less than 75% for mouse and rat, species cross-reactivity was assessed to mouse, rat, cynomolgus and rhesus monkey CD40L.

To assess binding to mouse CD40L (UniProt accession number: P27548), ProteOn GLC Sensor Chips were coated with 3000-4000 RU of recombinant mouse CD40L (R&D NS0) in 10 mM acetate buffer pH5.5. Purified monovalent anti-CD40L NANOBODIES® in ProteOn running buffer: PBS/Tween (phosphate buffered saline, pH 7.4 with 0.005% Tween 20) were flown over the sensor chips at 100 nM. Processed curves were used for off-rate analysis based on the Langmuir dissociation model. All 40 lead panel clones were tested. However, none of them showed binding to mouse CD40L.

Cross-reactivity to rat CD40L (UniProt accession numbers: Q9Z2V2 and Q9R254 (secondary)) was tested in FACS. Purified NANOBODIES® were analyzed on FACS for binding to rat CD40L. 2×10⁵ cells (transiently transfected rat CD40L HEK cells) were incubated with the purified NANOBODIES® in FACS buffer for 30 minutes at 4° C. Cells were washed 3×, re-suspended and incubated for 30 minutes at 4° C. Cells were washed again 3× and dead cells were stained with TOPRO3 (Molecular probes, T3605). Samples were analyzed on a FACSarray™ (BD Biosciences). Only the final four lead candidates (C01000281302, C0100029C10, C01000441307 and C01000461303) were tested. No binding was observed for any of the NANOBODIES®.

Cross-reactivity to cynomolgus CD40L (UniProt accession number: G7PG38) and rhesus CD40L (UniProt accession number: G7N4M5) was tested in a ligand competition assay. Purified NANOBODIES® were analyzed on FACS for competition with biotinylated human CD40L binding to human/rhesus/cynomolgus CD40-expressing cells. Human CD40L was used as the soluble forms of human, rhesus and cynomolgus (cyno) monkey CD40L are identical in sequence. 2×10⁵ cells (transiently transfected HEK cells) were incubated with dilution series of the purified NANOBODIES® in FACS buffer for 30 minutes at 4° C. Cells were then washed 3× and finally resuspended in FACS buffer containing Streptavidin-PE (BD Pharmingen, #554061). This mixture was incubated for 30 minutes at 4° C. Cells were further handled as set out above. The results are depicted in Table 6.7.

TABLE 6.7

Human/cyno/rhesus cross-reactivity (ligand competition)

| Construct | human CD40 IC50 (M) | human CD40 % block[2]* | cyno CD40 IC50 (M) | cyno CD40 % block | rhesus CD40 IC50 (M) | rhesus CD40 % block |
|---|---|---|---|---|---|---|
| C0100028B02 | 4.43E−09 | 71 | 4.70E−09 | 75 | 4.55E−09 | 72 |
| C0100029C10 | 1.42E−10* | 98 | 8.07E−09 | 81 | 1.24E−08 | 87 |
| C0100044B07 | 5.89E−09 | 82 | 5.28E−09 | 79 | 5.41E−09 | 83 |
| C0100046B03 | 1.53E−08 | 96 | 2.27E−08 | 97 | 2.82E−08 | 100 |

*suboptimal curve fit;
[2]*maximum observed effect

For each of the NANOBODIES®, $IC_{50}$ values were identical within the experimental error for the different CD40L species.

6.7.2 Selectivity

The Basic Local Alignment Search Tool (BLAST) was used to identify the closest related protein in the human protein database. The closest related proteins (non-CD40L variants) were TNFα, HVEM-L (TNF14) and RANKL (TNF11) with a sequence identity of 27.9%, 27.9% and 25.4%, respectively. To assess selectivity for CD40L, MaxiSorp plates (Nunc, 430341) were coated overnight with human CD40L (4° C.) followed by one hour blocking (PBS, 1% casein) at RT. A fixed concentration of NANOBODY® was used together with a dilution series of competitor (TNFα, HVEM-L (TNF14) and hRANKL (TNF11); CD40L was used as positive control), starting at a 100-fold excess. The NANOBODIES® were detected with anti-FLAG®-HRP (Sigma (A8592)).

No binding towards human TNFα, HVEM-L (TNF14) and hRANKL (TNF11) was observed for any of C01000281302, C0100029C10, C01000441307 and C01000461303.

6.8 Affinity Maturation

The four selected NANOBODIES® (C01000281302, C0100029C10, C01000441307 and C01000461303) had potencies in the nanomolar range in the B-cell proliferation assay, as indicated by the $IC_{50}$ (see Table 6.8).

TABLE 6.8

Overview of potency data of the 4 leads in the B-cell proliferation assay

| NANOBODY ® | Average IC50 (M) | Standard deviation IC50 (M) |
|---|---|---|
| C0100028B02 | 1.15E−09 | 5.05E−10 |
| C0100029C10 | 1.26E−09 | 6.58E−10 |
| C0100044B07 | 9.71E−10 | 2.48E−10 |
| C0100046B03 | 2.18E−09 | 1.09E−09 |

In order to further increase potency, NANOBODIES® were affinity matured. For screening of affinity maturation variants of the parental NANO BODIES®, off-rates were determined.

Affinity maturation was performed by screening error prone libraries generated from each parental NANOBODY® clone. In this approach, amino acid substitutions result from random introduction of mutations in the NANO-BODY® encoding DNA via an error prone PCR. As a consequence, amino acid substitutions are found both in the CDRs and in the Framework Regions (FRs). 5 rounds of phage display selections were performed in solution using decreasing concentrations of recombinant CD40L (from 50 nM to 0.05 pM). Following phage display, individual NANOBODIES® were sequenced and off-rates were determined by SPR analysis (cf. Example 6.1.3). Based on the off-rate data, mutations with a beneficial effect were further investigated.

6.8.1 C0100028802 (28802)

413 sequences were obtained after selection, of which 294 clones were non-redundant based on sequencing. Of these unique clones, the off-rates of 271 clones were tested on the ProteOn.

In essence, the framework mutations (up to 6 in one clone), which were scattered all over the NANOBODIES®, did not or only minimally affect the off-rates (data not shown). None of the FR mutations were retained. The CDR mutations are depicted in the Tables below.

Approximately 25% of the clones displayed an up to 2-fold improved off-rate over the parental NANOBODY®.

3 mutations in CDR3 were selected for further investigation based on this dataset:

L100aF: This mutation resulted in a 1.3-fold improved off-rate (preferably in combination with K43R);

D101G: This mutation resulted in a 1.3-fold improvement in off-rate; and Y102F: This mutation resulted in a 1.8-fold improvement in off-rate.

The final variant was C010002366 (SEQ ID NO: 7).

6.8.2 C0100046803 (46803)

731 sequences were obtained of which 229 clones were non-redundant. All 229 clones were tested on the ProteOn.

In essence, the framework mutations (up to 6 in one clone), which were scattered all over the NANOBODIES®, did not or only minimally affect the off-rates (data not shown). None of the FR mutations were retained. The CDR mutations are depicted in the Tables below.

| 28B02 | CDR1* | | | | | | | | | |
|---|---|---|---|---|---|---|---|---|---|---|
| Kabat numbering | 26 | 27 | 28 | 29 | 30 | 31 | 32 | 33 | 34 | 35 |
| absolute numbering | 1 | 2 | 3 | 4 | 5 | 6 | 7 | 8 | 9 | 10 |
| wildtype sequence | G | F | T | L | E | Y | Y | A | I | G |
| mutations | | | S | Q | | | | N | L | A |
| mutations | | | N | S | | | | V | V | |
| mutations | | | A | M | | | | | | |
| mutations | | | I | G | | | | | | |

*Up to 2 CDR1 mutations in one clone

| 46B03 | CDR1* | | | | | | | | | |
|---|---|---|---|---|---|---|---|---|---|---|
| Kabat numbering | 26 | 27 | 28 | 29 | 30 | 31 | 32 | 33 | 34 | 35 |
| absolute numbering | 1 | 2 | 3 | 4 | 5 | 6 | 7 | 8 | 9 | 10 |
| wildtype sequence | G | R | T | P | L | N | Y | H | M | A |
| mutations | E | H | I | S | F | S | H | N | K | S |
| mutations | R | G | A | . | . | D | . | . | T | G |
| mutations | . | . | S | . | . | I | . | . | V | T |
| mutations | . | . | P | . | . | . | . | . | . | . |

*Up to 2 CDR1 mutations in one clone

| 28B02 | CDR2* | | | | | | | | |
|---|---|---|---|---|---|---|---|---|---|
| Kabat numbering | 50 | 51 | 52 | 53 | 54 | 55 | 56 | 57 | 58 |
| absolute numbering | 1 | 2 | 3 | 4 | 5 | 6 | 7 | 8 | 9 |
| wildtype sequence | C | I | S | S | E | G | S | T | S |
| mutations | . | V | G | . | G | S | G | A | I |
| mutations | . | . | . | . | . | . | N | P | R |
| mutations | . | . | . | . | . | . | T | I | G |
| mutations | . | . | . | . | . | . | I | S | . |

*Up to 2 CDR2 mutations in one clone

| 46B03 | CDR2* | | | | | | | | | |
|---|---|---|---|---|---|---|---|---|---|---|
| Kabat numbering | 50 | 51 | 52 | 52a | 53 | 54 | 55 | 56 | 57 | 58 |
| absolute numbering | 1 | 2 | 3 | 4 | 5 | 6 | 7 | 8 | 9 | 10 |
| xivildtype sequence | A | I | S | S | L | L | G | S | T | D |
| mutations | G | V | . | N | . | I | S | I | P | . |
| mutations | . | . | . | R | . | . | D | G | S | . |
| mutations | . | . | . | G | . | . | . | F | . | . |

*Up to 2 CDR1 mutations in one clone

| 28B02 | CDR3* | | | | | | | | | | | | | | | | | | | |
|---|---|---|---|---|---|---|---|---|---|---|---|---|---|---|---|---|---|---|---|---|
| Katat numbering | 95 | 96 | 97 | 98 | 99 | 100 | 100a | 100b | 100c | 100d | 100e | 100f | 100g | 100h | 100i | 100j | 100k | 100l | 101 | 102 |
| absolute numbering | 1 | 2 | 3 | 4 | 5 | 6 | 7 | 8 | 9 | 10 | 11 | 12 | 13 | 14 | 15 | 16 | 17 | 18 | 19 | 20 |
| wildtype sequence | D | P | D | R | G | F | L | G | S | S | C | D | T | Q | S | H | Q | Y | D | Y |
| mutations | . | . | . | S | . | . | F | D | G | N | . | G | N | H | P | N | L | F | G | F |
| mutations | . | . | . | . | . | . | M | A | N | G | . | N | A | K | T | Y | R | . | . | N |
| mutations | . | . | . | . | . | . | W | S | R | R | . | E | . | L | . | . | H | . | . | . |
| mutations | . | . | . | . | . | . | . | . | . | . | . | V | . | R | . | . | . | . | . | . |

*Up to 3 CDR mutations in one clone

| 46B03 | | | | | | | | CDR3* | | | | | | | | | | | | |
|---|---|---|---|---|---|---|---|---|---|---|---|---|---|---|---|---|---|---|---|---|
| Kabat numbering | 95 | 96 | 97 | 98 | 99 | 100 | 100a | 100b | 100c | 100d | 100e | 100f | 100g | 100h | 100i | 100j | 100k | 100l | 101 | 102 |
| absolute numbering | 1 | 2 | 3 | 4 | 5 | 6 | 7 | 8 | 9 | 10 | 11 | 12 | 13 | 14 | 15 | 16 | 17 | 18 | 19 | 20 |
| wildtype sequence | R | E | T | T | H | Y | S | T | S | D | R | V | N | E | M | R | H | Y | D | Y |
| mutations | Q | D | S | I | Y | H | T | I | N | A | S | . | D | V | V | K | N | . | N | H |
| mutations | L | K | M | S | N | N | G | A | R | . | G | . | V | A | K | S | L | . | . | F |
| mutations | . | . | A | A | . | . | N | . | . | . | . | . | S | D | T | W | Q | . | . | N |
| mutations | . | . | K | R | . | . | I | . | . | . | . | . | . | N | . | M | R | . | . | . |
| mutations | . | . | . | . | . | . | . | . | . | . | . | . | . | . | . | G | D | . | . | . |
| mutations | . | . | . | . | . | . | . | . | . | . | . | . | . | . | . | T | . | . | . | . |

*up to 4 CDR3 mutations in one clone

Approximately 25% of the clones displayed an up to 5.2-fold improved off-rate over the parental NANOBODY®. 6 positions were selected for further investigation based on this dataset:

Y100H: no effect on off-rate
Y100I: 1.5 fold improved off-rate
S100aT: no effect on off-rate
N100gD: effect not pronounced
E100hV: no effect on off-rate
M100iI: no effect on off-rate
H100 kN: single mutation 2.6-fold improved off-rate
H100kA: about 2-fold improved off-rate
H100kS: about 2-fold improved off-rate
The final variant was C010003290 (SEQ ID NO: 8).

6.9 Alb-Variants

In the research leading to the present invention it was discovered that adding a C-terminal extension to the C-terminal region of a NANOBODY® essentially prevents binding of pre-existing antibodies in the vast majority of plasma/serum samples of healthy human subjects (see below). However, blood and serum from a number of human subjects suffering from certain severe (auto-)immune disorders, including SLE, appear to contain some pre-existing antibodies/factors that can bind to NANOBODIES® even when said NANOBODIES® comprise a C-terminal extension.

In the examples below, the binding of pre-existing antibodies that are present in the samples used (i.e. from healthy volunteers and SLE patients) to the NANOBODIES® tested was determined using ProteOn as follows: Binding of pre-existing antibodies on NANOBODIES® captured on human serum albumin (HSA) was evaluated using the ProteOn XPR36 (Bio-Rad Laboratories, Inc.). PBS/Tween (phosphate buffered saline, pH7.4, 0.005% Tween20) was used as running buffer and the experiments were performed at 25° C. The ligand lanes of a ProteOn GLC Sensor Chip were activated with EDC/NHS (flow rate 30 µl/min) and HSA was injected at 10 µg/ml in ProteOn Acetate buffer pH4.5 (flow rate 100 µl/min) to render immobilization levels of approximately 3200 RU. After immobilization, surfaces were deactivated with ethanolamine HCl (flow rate 30 µl/min). NANOBODIES® were injected for 2 minutes at 45 µl/min over the HSA surface to render a NANOBODY® capture level of approximately 200 RU. The samples containing pre-existing antibodies were centrifuged for 2 minutes at 14,000 rpm and the supernatant was diluted 1:10 in PBS-Tween20 (0.005%) before being injected for 2 minutes at 45 µl/min followed by a subsequent 400 seconds dissociation step. After each cycle (i.e. before a new NANOBODY® capture and blood sample injection step) the HSA surfaces were regenerated with a 2 minute injection of HCl (100 mM) at 45 µl/min. Sensorgram processing and data analysis was performed with ProteOn Manager 3.1.0 (Bio-Rad Laboratories, Inc.). Sensorgrams showing pre-existing antibody binding were obtained after double referencing by subtracting 1) NANOBODY®-HSA dissociation and 2) non-specific binding to reference ligand lane. Binding levels of pre-existing antibodies were determined by setting report points at 125 seconds (5 seconds after end of association). Percentage reduction in pre-existing antibody binding was calculated relative to the binding levels at 125 seconds of a reference NANOBODY®. Reference A=Alb8 (SEQ ID NO: 16); Reference B=Alb8+A (SEQ ID NO: 17) (see Table 2).

6.9.1: Influence of S112K Mutation on Binding of Pre-Existing Antibodies that are Present in Human SLE Samples Reference A and Reference B were tested for binding by pre-existing antibodies from 7 serum samples obtained from patients who were confirmed positive for SLE. For comparison, plasma samples from two healthy human volunteers were included.

Binding of pre-existing antibodies in the samples tested to the NANOBODIES® was measured on ProteOn according to the general protocol outlined above. The results are shown in Table 6.9.1 below.

As can be seen from a comparison of the binding data for Reference A and Reference B and NANOBODIES® of the invention, the samples obtained from some of the SLE patients appear to contain certain pre-existing antibodies that can still bind to NANOBODIES® even in the presence of a C-terminal alanine residue (the C-terminal alanine residue did essentially prevent/remove (partially or essentially fully) all binding of the pre-existing antibodies that were present in the plasma samples from healthy volunteers).

It can further be seen that the binding of these pre-existing antibodies from SLE samples could be greatly reduced by mutations at positions 11 and 112 (and in case of position 112, in particular by S112K).

6.9.2: Influence of Combined Framework Mutations and C-Terminal Extension on Binding of Pre-Existing Antibodies that are Present in Human SLE Samples Four different NANOBODIES® (with specific framework mutations and with or without C-terminal alanine extension) were tested for binding of pre-existing antibodies from 5 serum samples obtained from patients who were confirmed positive for SLE. For comparison, one plasma sample from a healthy human volunteer was included.

Binding of pre-existing antibodies in the samples to the NANOBODIES® tested was measured on ProteOn according to the general protocol outlined above. The results are shown in Tables 6.9.2(a) and 6.9.2(b) below.

As can be seen from a comparison of the binding data for Reference A and Reference B, the samples obtained from SLE patients appear to contain certain pre-existing antibodies that can still bind to NANOBODIES® even in the presence of a C-terminal alanine residue. The C-terminal alanine residue did essentially prevent/remove all binding of the pre-existing antibodies that were present in the plasma samples from the healthy volunteer.

It can further be seen that the binding of these pre-existing antibodies from SLE samples could be greatly reduced by mutations at positions 11 and 112 (and in case of position 112, in particular by S112K).

6.9.3: Influence of a V89T Mutation on Binding of Pre-Existing Antibodies in Samples from SLE Patients.

As described herein, samples obtained from certain SLE patients appear to contain pre-existing antibodies/factors that can bind to the exposed C-terminal end of a VH domain, even when a C-terminal extension is present. It was investigated whether a V89T mutation could reduce or prevent/remove such binding, with or without the presence of a C-terminal extension. The results are also shown in Tables 6.9.2(b) and 6.9.3(a) below.

As can be seen, a V89T mutation could essentially prevent/remove binding of pre-existing antibodies that are present in samples obtained from SLE patients, to a similar degree as an S112K mutation. However, as can be seen from comparing the data given in Tables 6.9.2(b) and 6.9.3(a) for NANOBODIES® with a V89T mutation and without a C-terminal extension with similar NANOBODIES® with an S112K mutation and without a C-terminal extension, having a mutation at position 112 in a NANOBODY® without a C-terminal extension generally reduces binding of pre-existing antibodies in samples from a healthy volunteer to a larger degree than a V89T mutation (i.e. 100%, 85% and 64% of S112K NANOBODIES® vs. 9%, 11% and 16% for V89T NANOBODIES®, respectively). For this reason, the use of a mutation at position 112 (and in particular S112K or S112Q) will often be preferred over the use of a mutation at position 89 (such as V89T).

However, as can also be seen from the data in Tables 6.9.2(b) and 6.9.3(a), adding a C-terminal alanine to a V89T NANOBODY® completely prevented/removed the binding of pre-existing antibodies in a sample obtained from healthy volunteers, and for this reason a combination of a V89T mutation and a C-terminal extension as described herein will usually be preferred (i.e. over the use of a V89T without C-terminal extension) if the V89T NANOBODY® or VH domain has, or is intended to have, an exposed C-terminal region in the protein or polypeptide in which it will be present (for example, because it forms the C-terminal end of the same).

To confirm that the results/findings from the table above are broadly applicable, representative NANOBODIES® with S112K and/or V89T mutations were tested against a test panel of 96 (S112K) and 129 (V89T) human serum samples. Binding was determined on ProteOn using the protocol set out above.

The results are summarized in FIG. 1 and Table 6.9.3(b) (representative NANOBODY® with a S112K mutation). In FIG. 1, a NANOBODY® with a S112K mutation (Reference A+S112K+C-terminal alanine—see Table 6.9.2(b) above) was compared to a reference NANOBODY® (Reference A; SEQ ID NO: 16). The NANOBODY® with the S112K mutation and Reference A were both tested against each of the serum samples, and the binding level at 125 seconds (RU) was determined. The data was then plotted in FIG. 1, with each point presenting the binding measured in one sample for either Reference A (indicated as (1) in FIG. 1) or for the S112K mutant (indicated as (2) in FIG. 1). The dotted line indicates a measured binding level of 20 RU.

The same data is also represented numerically in Table 6.9.3(b), which mentions—for Reference A and the S112K mutant, respectively—the total number of samples tested that gave a level of binding at 125 seconds of more than 20RU, less than 20 RU (i.e. between 0 and 20 RU) and less than 10 RU.

As can be seen from the data plotted in FIG. 1 and shown in Table 6.9.3(b), for Reference A, more than half of the 96 samples tested gave a binding level of more than 20 RU (in some cases, as high as 150-200 RU), indicating that the pre-existing antibodies present in the sample were binding to Reference A. By comparison, for the S112K mutant, no sample gave a binding level of more than 20 RU (and most less than 10 RU), indicating that the S122K mutation was essentially capable of reducing/preventing binding of the pre-existing antibodies in all of the 96 samples tested.

A similar plot and similar data is shown in FIG. 2 and Table 6.9.3(c), respectively, for a representative NANOBODY® with a V89T mutation (Reference A+L11V+V89T+C-terminal alanine; see Table 6.9.3(a) above), tested against 129 serum samples and again compared to Reference A (indicated by (1) in FIG. 2; the V89T mutant is indicated by (2) in FIG. 2).

Again, from the plot in FIG. 2 and the data in Table 6.9.3(c), it can be seen that with a few exceptions (i.e. less than 10% of samples tested, which then each gave an absolute binding value after 125 seconds of about 100 RU or less), the V89T mutation was capable of reducing/preventing binding of the pre-existing antibodies in most of the 129 samples tested, whereas the reference without the V89T mutation was bound by pre-existing antibodies in most of the samples tested.

TABLE 6.9.3(b)

testing of representative Nanobody with S112K mutation against 96 serum samples.

| Nanobody tested | Binding level at 125 seconds < 10 RU | Binding level at 125 seconds < 20 RU | Binding level at 125 seconds > 20 RU |
|---|---|---|---|
| Reference A | 34 | 41 | 55 |
| Reference A + S112K + C-terminal alanine | 92 | 96 | 0 |

TABLE 6.9.3(c)

testing of Nanobody mutants with V89L and/or T100K/Q mutations against 129 serum samples.

| Nanobody tested | Binding level at 125 seconds < 10 RU | Binding level at 125 seconds < 20 RU | Binding level at 125 seconds > 20 RU |
|---|---|---|---|
| Reference A | 27 | 40 | 89 |
| Reference A + L11V + V89T + C-terminal alanine | 110 | 119 | 10 |

6.10 Final Format

Based on the data of optimizing Alb-variants to reduce binding of pre-existing antibodies (see Example 6.9), ISVDs binding CD40L were fused to optimized Alb-variants, and further tested.

6.10.1 Binding of Pre-Existing Antibodies on Final Format.

C01000281302 and C01000461303 were fused to both an Alb11- and an Alb23-variant, i.e. Alb00129 (Alb11(L11V, V89T)-A) and Alb00132 (Alb23(L5V,L11V,V89T)-A), respectively (see Table 6.10).

TABLE 6.10

HLE extended leads

| Nanobase ID | Description |
|---|---|
| C010003320 | C0100028B02(E1D, T60A, A74S, K83R, Y102F)-20GS-Alb11(L11V, V89T)-A |
| C010003323 | C0100028B02(E1D, T60A, A74S, K83R, Y102F)-20GS-Alb23(L5V, L11V, V89T)-A |
| C010003326 | C0100028B02(E1D, T60A, A74S, K83R, Y102F)-20GS-ALB11(S112K)-A |
| C010003313 | C0100046B03(E1D, A14P, S60A, L63V, D65G, A74S, A76T, R81Q, N82bS, K83R, Y100I, M100il, H100kN)-9GS-Alb11(L11V, V89T)-A |
| C010003315 | C0100046B03(E1D, A14P, S60A, L63V, D65G, A74S, A76T, R81Q, N82bS, K83R, Y100I, M100il, H100kN)-9GS-Alb23(L5V, L11V, V89T)-A |
| C010003318 | C0100046B03(E1D, A14P, S60A, L63V, D65G, A74S, A76T, R81Q, N82bS, K83R, Y100I, M100il, H100kN)-9GS-ALB11(S112K)-A |

The absence of binding to pre-existing antibodies was assessed for the final formats in essence as set out above in 6.9.

There was a significant reduction/prevention of binding of pre-existing antibodies to the HLE extended leads upon adding a C-terminal Alanine and engineering L11V and V89T in the Alb8 building block. Similar pre-existing antibodies binding profiles were seen for C010003313 ("3313") and C010003320 ("3320"). This also demonstrates that the binding profile of the pre-existing antibodies appears to be independent of the linker.

There was a significant reduction/prevention of binding of pre-existing antibodies to the HLE extended leads upon adding a C-terminal Ala and engineering S112K into the Alb8 building block.

Similar pre-existing antibodies binding profiles were seen for C010003318 ("3318") compared to C010003326 ("3326"). This again demonstrates that the reduction or prevention of pre-existing antibodies by adding an optimized Alb-variant appears to be independent of the linker used for linking the lead NANOBODY® to the optimized Alb-variant.

Moreover, this also demonstrates that in this case only the C-terminal building block (in this case the optimized Alb-variant) needs to be modified in order to acquire a significant reduction/prevention of binding of pre-existing antibodies to the whole construct.

6.11 Potency in B-Cell Activation and Proliferation Assays

The potency of the lead candidate C010003318 was assessed in a B-cell activation and B-cell proliferation assay (cf. Examples 6.1.6 and 6.4). The potency was compared to 5C8 and non-pegylated CDP7657. The results are summarized in Table 6.11.

TABLE 6.11

B-cell activation and B-cell proliferation assay

| IC50 (pM) | 5c8 | CDP7657* | C010003318 |
|---|---|---|---|
| B-cell activation | 119 | 101 | 212 |
| B-cell proliferation | 51 | 864 | 308 |

*non-pegylated CDP7657

Based on the B-cell proliferation data it was demonstrated that C010003318 has a higher potency than non-pegylated CDP7657, although C010003318 has a 10 to 6 fold lower potency compared to 5C8.

Based on the B-cell activation data it can be seen that non-pegylated CDP7657 and 5C8 appear to be about a factor 2 more potent than C010003318.

In conclusion, 5C8 is about 2-10 fold more potent than C010003318 in these in vitro assays. In the more relevant B-cell proliferation assay (cf. Example 6.4) C010003318 is patently more potent than CDP7657. In the B-cell activation assay it appears that CDP7657 is about a factor 2 more potent than C010003318. However, as indicated in Example 6.6, pegylation of CDP7657 decreased activity by 4-5 fold (cf. U52010/0104573).

Hence, C010003318 appears to be more potent than CDP7657 in all assays.

6.12 Affinity Towards CD40L

To define the affinity to hCD40L of the final bispecific HLE lead NANOBODIES®, a kinetic exclusion assay (KinExA) was run on a KinExA 3200 (Sapidyne Inc.).

Responses were then entered in the KinExA Pro Software v3.2.6 and percentages free NANOBODY® was plotted versus hCD40L concentrations. No outliers were excluded from the fit. Correction for drift or Ligand related non-specific binding was not necessary. Low variation was observed. The plotted values were fitted using the "Affinity, Standard" analysis method. The KD results are depicted in Table 6.12.

TABLE 6.12

Affinity (pM) of C010003318 and C010003326 in in-solution KinExA assay

| | KD (pM) [95% CI] |
|---|---|
| C010003318 | 17 pM [12-22 pM] |
| C010003326 | 4 pM [3-6 pM] |

6.13 TT Studies in Mouse and Cynomolgus Demonstrate that the NANOBODIES® are Efficacious in Neutralizing CD40L Activity In Vivo In order to assess in vivo the CD40L-neutralizing capacity of the lead NANOBODIES®, a tetanus toxoid (TT) challenge study was performed in humanized mice and cynomolgus monkey.

6.13.1 NANOBODIES® neutralize CD40L activity in TT studies in humanized mice.

Since the NANOBODIES® were not cross-reactive with mice CD40L (see Example 6.7.1), humanized mice were immunized day with tetanus toxin (TT) and the effect of CD40L neutralization on the TT-specific IgG antibody response was evaluated at different time points. NANOBODY® was administered prior to the TT challenge and every 3 days for a total of 10 administrations per individual. TT was administered on day 1 and day 31. The anti-CD40L 3318 NANOBODY® impaired the TT-IgG response in these mice and this effect was significant (data not shown). The immune suppressive effect was dose dependent, but all doses tested reduced the IgG response better than the control. The immune suppressive effect of the NANOBODIES® was confirmed by the absence of mature human B cells in the spleen of these NANOBODY®-treated mice. Similarly, in the mouse TT study, NANOBODIES® 3313 and 3320 were proven to be efficacious in significantly reducing the TT-IgG response when compared to the vehicle group. In addition, these NANOBODIES® impair the settling and growth of hu PBL in the spleen of TT immunized human PBMC engrafted immune deficient mice as well (data not shown).

Hence, all NANOBODIES® tested are efficacious in neutralizing CD40L activity in vivo.

6.13.2 NANOBODIES® Neutralize CD40L Activity in TT Studies in Cynomolgus Monkey.

The cynomolgus monkey TT study was performed similarly to Example 6.13.1. In short, cynomolgus monkeys were immunized daily with tetanus toxin and the effect of CD40L neutralization on the TT-specific IgG antibody response was evaluated at different time points. NANOBODY®, 5C8 and Vehicle were administered on Day 0 and Day 31. On Day 1+4 h and Day 31, TT was administered. As depicted in FIG. 7, the anti-CD40L C010003318 NANOBODY® impaired the TT-IgG response in these monkeys and this effect was significant. The immune suppressive effect was dose dependent, but all doses tested reduced the IgG response better than the control. The data are indicative of saturation of the soluble target at all NANOBODY® doses.

Hence, all NANOBODIES® tested are efficacious in neutralizing CD40L activity in vivo. The data in cynomolgus monkey confirm the data in mice and prove the broad applicability of the NANOBODIES®, even without a functional Fc region. Notably, an Fc effector function of anti-CD40L was shown to be influencing the humoral response to TT (Shock et al. 2015 Arthritis Research & Therapy 17:234).

6.14 In Vitro Evaluation of the Risk for TE/Thrombosis

As mentioned before, despite encouraging evidence of clinical effect, further development of hu5C8 was discontinued because of the increased incidence of treatment-emergent cardiovascular thrombotic events (TE). Also, in a study of 5C8 in rhesus monkey, numerous TEs including pulmonary vascular thrombi and vasculopathy were found after the administration of 5C8 (Wakefield et al. 2010 Arthritis Rheum. 62:1243).

Hence, before anti-CD40L NANOBODIES® can be used clinically, assessment of its safety is of the utmost importance. Safety was assessed in various systems in vivo and in vitro. The following methods and approaches were designed to evaluate the risk of TE and/or thrombosis in vitro.

6.14.1 Safety In Vitro—Platelet Assays.

As it has been described by Roth et al. that anti-CD40L mAbs can induce platelet activation and aggregation via immune complexes that cluster FcgRIIa on platelets, anti-CD40L NANOBODIES® were tested in platelet activation and aggregation assay to investigate their intrinsic potential to stimulate platelets (Roth et al., 2004 Transplantation 78:1238-9).

C010003313 and C010003318 were assayed in a platelet activation assay and platelet aggregation assay as set out before. 5C8 was taken along as a positive control in these assays as well as ADP. Both for healthy volunteers and SLE patients, platelet activation was observed for 5C8. In contrast, C010003313 and C010003318 demonstrated a non-activating profile in healthy volunteers and SLE patients (FIG. 3 and FIG. 4, respectively). In addition, these NANOBODIES® were tested in the platelet aggregation assay with healthy volunteer and SLE patient blood, and were concluded not to induce platelet aggregation, whereas 5C8 did. The results of the platelet aggregation assay are depicted in FIG. 5 (Healthy volunteers) and FIG. 6 (SLE patients).

Hence, in the in vitro platelet activation and aggregation assay it was demonstrated that the NANOBODIES® do not induce platelets whereas 5C8 does.

6.14.2 Safety In Vitro—Endothelial Cell Activation Systems

Membrane CD40L is transiently expressed on activated mature T cells, primarily restricted to CD4$^+$ T cells, but not on resting T cells. Expression of membrane CD40L has also been detected on cells other than T lymphocytes, namely activated platelets, primary cells, mast cells, basophils and eosinophils, while CD40 expression is demonstrated on B cells, natural killer cells, monocytes/macrophages, dendritic cells under certain conditions and widely on non-hematopoietic cells including endothelial cells, fibroblasts and epithelial cells. As endothelial cells are key players in hemostasis next to platelets, the influence of anti-CD40L agents on endothelium cells was assessed in two systems containing primary HUVECs (human umbilical vein endothelial cells): the stimulated 3C system (to mimic cardiovascular disease/chronic inflammation) and the unstimulated HNo system (to mimic healthy vascular endothelium)(Bioseek). The anti-CD40L NANOBODY®, an irrelevant control NANOBODY®, 5C8 and piclamilast as positive control were tested at four different concentrations in this system.

The results demonstrate that the NANOBODY® profile was considered not indicative of any effect on endothelial cells (data not shown). On the other hand, piclamilast was associated with an inflammatory status, while the most striking result was obtained with 5C8. So far no influences from 5C8 on endothelial cells have been reported, but in both cell systems a clear and dose-dependent response was observed. In particular, all markers monitored (inflammatory, immunomodulatory, tissue remodeling and hemostasis) were increased in one or both cell systems due to 5C8.

In conclusion, the tested NANOBODIES® did not induce activation of primary endothelial cells, whereas 5C8 did. Hence, anti-CD40L NANOBODIES® appear to be safe.

6.14.3 Safety In Vitro—Anti-CD40L NANOBODIES® do not Initiate Reverse Signaling The binding of CD40L to its receptor CD40 induces forward signals depending on the activation state of the cells and the expression levels of the receptors on the cells. Additionally, it is known that binding of ligands to TNFR family members (e.g. CD40) can initiate reverse signaling, regulating cell proliferation, cytokine secretion, oxidative burst, class switch, and T cell maturation. However, non-regulated or disproportionate reverse signaling by members of the TNFα family may result in a cytokine storm, which is generally known as an excessive or uncontrolled release of proinflammatory cytokines (Eissner et al., 2004 Cytokine & Growth Factor Reviews 15:353-366).

To further evaluate the safety, the potential of NANOBODIES® for a initiating a cytokine storm due to reverse signalling was assessed.

Human PBMC's from 10 healthy donors were stimulated with different compounds at different concentrations: Avastin, a monoclonal anti-CD3 antibody, CDP7657 and the anti-CD40L NANOBODY® C010003318. Also SEB and LPS were taken along to assess the responsiveness of the PBMC. Avastin was used as negative control (Min & Kawabata, 2009 in EMA Workshop "in vitro cytokine release assays") and the anti-CD3 antibody as positive control.

The method to assess in vitro cytokine release using human PBMC consists of three consecutive steps: isolation of human PBMC from buffy coats and freezing, thawing of the human PBMC and stimulation with different compounds and finally the quantification of the cytokines in the assay supernatant. Sample analysis was performed at Eurofins Panlabs Inc. using the Luminex platform (Life Technologies). The measured cytokines were IL-113, IL-2, IL-6, IL-10, TNF-α and IFN-γ. The cytokines were analysed in 2 different Luminex assays. The first assay measured IL-113, IL-2, IL-6 and IL-10 and the second assay measured TNF-α and IFN-γ. Based on the detection limits of the kits determined by the provider and the experiments performed at Ablynx in which an estimate was made on the grade of stimulation for each cytokine, the dilutions of the samples were adjusted for both assays. The assays were performed as indicated in the kit insert and each sample was analysed in duplicate. Statistical data analysis was performed on the obtained results to compare all compounds to the blank (unstimulated PBMC's).

The results demonstrate that the cytokine production induced by Avastin and the monoclonal anti-CD3 antibody on the human PBMC's was higher than that of the unstimulated PBMC's. Also the levels of the cytokines induced by the positive control compounds SEB and LPS were higher than those of the blank. For compound CDP7657 the levels of cytokines IL-2, TNF-α and IFN-γ were comparable to those of the blank, while for IL-113, IL-6 and IL-10 there were some differences observed dependent on the tested concentration. An illustrative result from the IL-6 induction upon the PBMC stimulation is depicted in FIG. 8. In particular, the overall cytokine inductions with the anti-CD3 compound and Avastin were demonstrated to be positive compared to the unstimulated samples. The induction with the CDP7657 compound resulted in IL-6 levels that were higher than that of the blank samples. The IL-6 levels induced by the NANOBODY® C010003318 were overall similar to the IL-6 levels measured in the unstimulated samples, except at the 20 nM concentration, where the measured IL-6 levels were higher than the blank, albeit minimally (which is believed to be an outlier). The positive control compounds SEB and LPS were shown to be positive compared to the blank.

Overall, the cytokine induction by the exemplary NANOBODY® C010003318 was comparable to that of the unstimulated PBMCs.

In conclusion, anti-CD40L NANOBODIES® do not initiate a cytokine storm due to reverse signalling in an in-vitro setting. This confirms again the safety of the NANOBODIES®.

6.15 Safety In Vivo—Anti-CD40L NANOBODIES® are Safe in Rhesus Monkey

A further study was set up to assess the safety of anti-CD40L NANOBODIES® in vivo. In particular, it was determined whether subcutaneous administration of anti-CD40L NANOBODIES® would translate also to a lack of TEs in vivo in rhesus monkeys.

The exemplary NANOBODY® C010003318 was administrated at a dose of 30 mg/kg, 100 mg/kg and 300 mg/kg each into 3 female rhesus monkeys, once weekly for 4 weeks.

The following parameters and end points were evaluated in this study: clinical signs, body weights, body weight changes, body temperature, clinical pathology parameters (haematology, coagulation, clinical chemistry, urinalysis and lymphocyte phenotyping), immunogenicity (anti-drug-antibody (ADA)), toxicokinetics, pharmacodynamics, gross necropsy findings, organ weights, and histopathologic examinations. The examinations included the following.

The in-life procedures, observations, and measurements listed below were performed for all animals. Animals were checked once in the morning and once in the afternoon each day for general health, mortality and moribidity. Moreover, animals were observed daily from Week −2. From Day 1 (on dosing days), animals were observed predose and at least 3 times after dosing. On non-dosing days animals were checked in the morning and in the afternoon. At least once a week, beginning Week −2, all animals received a detailed clinical observation. All animals were examined regularly throughout the day, on each day of dosing, for reaction to treatment. The onset, intensity and duration of signs were recorded; particular attention was paid to the animals during and for the first hour after dosing. Injection sites were monitored for reaction to treatment. Body weights were recorded weekly commencing from Week −2. A weight was recorded on the day of scheduled necropsy. All animals had a body temperature recorded once during pretreatment (in the afternoon at the expected time of postdose measurement). During the dosing period, all animals had a body temperature recorded weekly at approximately 8 h post dose on each dosing day and before necropsy.

Blood samples (0.5 mL) were collected into $K_2$EDTA tubes analysed for the parameters specified in Table 6.15A.

TABLE 6.15A

| Haematology parameters | |
|---|---|
| Red blood cell count | Mean platelet component |
| Haemoglobin | Mean platelet volume |
| Haematocrit | Platelet distribution width |
| Mean cell volume | White blood cell count |
| Mean cell haemoglobin | Neutrophils |
| Mean cell haemoglobin concentration | Lymphocytes |
| Haemoglobin distribution width | Monocytes |
| Reticulocytes | Eosinophils |
| Reticulocyte count (absolute) | Basophils |
| Red blood cell distribution width | Large unstained cells |
| Platelet count | Erythrocyte sedimentation rate |
| Plateletcrit | |

Blood samples (1 mL) were taken into tubes containing 3.8% (w/v) trisodium citrate and processed for plasma, which was analysed for the parameters activated partial thromboplastin time fibrinogen and prothrombin time.

Blood samples (1.5 mL) were taken into tubes containing lithium heparin and processed for plasma, which was analysed for the parameters specified in Table 6.156

TABLE 6.15B

| clinical chemistry parameters | |
|---|---|
| Urea | Total protein |
| Glucose | Albumin |
| Aspartate aminotransferase | Globulin |
| Alanine aminotransferase | Albumin/globulin ratio |
| Alkaline phosphatase | Cholesterol |
| Creative phosphokinase | LDL Cholesterol |
| Lactate dehydrogenase | HDL Cholesterol |
| Sodium | Creatinine |
| Potassium | Total bilirubin |
| Chloride | Calcium |
| Gamma glutamyl transferase | Inorganic phosphate |
| Glutamate dehydrogenase | Triglycerides |
| Alpha amylase | Total Bile Acids |
| | Immunoglobin G, M, A |

Representative samples of the tissues identified in Table 6.15C were collected from all animals and preserved in 10% neutral buffered formalin, unless otherwise indicated.

TABLE 6.15C

| Tissue collection and preservation | |
|---|---|
| Administration, site | Larynx |
| Animal identification | Liver |
| Artery, aorta | Lung |
| Bone marrow smears | Lymph node, mandibular |
| Bone marrow, femur | Lymph node, mesenteric |
| Bone marrow, sternum | Lymph node, drainage |

TABLE 6.15C-continued

Tissue collection and preservation

| | |
|---|---|
| Bone, femur | Muscle, skeletal |
| Bone, sternum | Nerve, optic[a] × 2 |
| Bone, stifle joint | Nerve, sciatic × 2 |
| Brain | Oesophagus |
| Cervix | Ovary × 2 |
| Eye[a] × 2 | Oviduct × 2 |
| Gallbladder | Pancreas |
| Gland, adrenal × 2 | Skin |
| Gland, lacrimal × 2 | Small intestine, duodenum |
| Gland, mammary × 2 | Small intestine, ileum |
| Gland, parathyroid × 2 | Small intestine, jejunum |
| Gland, pituitary | Spinal cord |
| Gland, salivary × 2 | Spleen |
| Gland, thyroid × 2 | Stomach |
| Gross lesions/masses | Thymus |
| Gut-associated lymphoid tissue (Peyer's patches) | Tongue |
| | Trachea |
| Heart | Ureter × 2 |
| Kidney × 2 | Urinary bladder |
| Large intestine, caecum | Uterus |
| Large intestine, colon | Vagina |
| Large intestine, rectum | |

[a]Preserved in Davidson's fixative.

The tissues identified in Table 6.15C were embedded in paraffin, sectioned (4-6 μm), mounted on glass sides, and stained with haematoxylin and eosin. Histopathological evaluation was performed by a veterinary pathologist with training and experience in laboratory animal pathology. A pathology peer review was conducted by a second pathologist at the Test Facility.

Subcutaneous administration of C010003318 to rhesus monkeys at 30, 100 or 300 mg/kg, once weekly for 4 weeks, was associated with microscopic findings of lymphoid depletion of germinal centres in the lymph nodes (axillary, inguinal, mandibular and mesenteric) at all dose levels and spleen, and hyalinisation of germinal centres in the spleen at 30 and 100 mg/kg. These findings were expected pharmacological effects of the test item and therefore considered not to be adverse. There were no test item-related effects on organ weights or gross pathology. There were no test item-related changes in clinical signs observed or changes in body weight. There were no test item-related effects in clinical pathology parameters.

In conclusion, administration of the exemplary NANOBODY® C010003318 subcutaneously once weekly for 4 weeks was well tolerated in female rhesus monkeys at levels of up to 300 mg/kg/week.

Target organ effects (lymphoid tissues) were observed at levels of 30 to 300 mg/kg/week but were considered to be a result of the pharmacological activity of the test item, and therefore not adverse. Based on these results, the no-observed-adverse-effect level (NOAEL) was considered to be 300 mg/kg/week as the highest dosage (tested).

Thus, even after prolonged high doses exposure there is no evidence that anti-CD40L NANOBODIES® induce TEs in vivo.

6.16 Immunogenicity (ADA) Evaluation

For assessment of immunogenicity, blood samples were collected from all animals (see Example 6.15) to determine the presence of pre-existing antibodies (PEA) (cf. Example 6.9) or emerging anti-drug antibodies (ADAs).

ADA sample analysis was performed to support toxicokinetic evaluation and/or safety evaluation. Plasma samples were evaluated for the presence of anti-drug antibodies (ADAs) using a validated electrochemiluminescence (ECL)-based bridging format for ADA sample analysis (on an MSD platform). Samples were collected from all 4 animal groups, either vehicle-treated (n=3) or treated with 30, 100 or 300 mg/kg NANOBODY®. The blood samples were collected from all animals before the start of the study (pre-study Day −7) and at Day 15 and Day 29 prior to administration on that day.

The responses from all samples were below the screening cut-point, so it was concluded that no pre-Ab were detected in the pre-study day −7 samples and no treatment-emergent ADA were detected in any of the samples from the vehicle-treated or the NANOBODY®-dosed animals. Also, these results corroborate the findings of Example 6.9.

Hence, no pre-existing or treatment emergent ADA were detected throughout the study, with a sufficiently sensitive and drug tolerant ADA assay.

The entire contents of all of the references (including literature references, issued patents, published patent applications, and co-pending patent applications) cited throughout this application are hereby expressly incorporated by reference, in particular for the teaching that is referenced hereinabove.

TABLE 1

Preferred Linker sequences of the invention

| Name of linker | SEQ ID NO: | Amino acid sequences |
|---|---|---|
| GS5 (5GS) | 18 | GGGGS |
| GS7 (7GS) | 19 | SGGSGGS |
| GS8 (8GS) | 20 | GGGGGGGS |
| GS9 (9GS) | 21 | GGGGSGGGS |
| GS10 (10GS) | 22 | GGGGSGGGGS |
| GS15 (15GS) | 23 | GGGGSGGGGSGGGGS |
| GS18 (18GS) | 24 | GGGGSGGGGSGGGGGGS |
| GS20 (20GS) | 25 | GGGGSGGGGSGGGGSGGGGS |
| GS25 (25GS) | 26 | GGGGSGGGGSGGGGSGGGGSGGGGS |
| GS30 (30GS) | 27 | GGGGSGGGGSGGGGSGGGGSGGGGSGGGGS |

TABLE 1-continued

Preferred Linker sequences of the invention

| Name of linker | SEQ ID NO: | Amino acid sequences |
|---|---|---|
| GS35 (35GS) | 28 | GGGGSGGGGSGGGGSGGGGSGGGGSGGGGSGGGGS |
| GS40 (40GS) | 29 | GGGGSGGGGSGGGGSGGGGSGGGGSGGGGSGGGGSGGGGS |
| A3 (3A) | 77 | AAA |

TABLE 2

Miscellaneous sequences

| Name | ID | Amino acid sequences |
|---|---|---|
| hCD40L (uniprot P29965-1) | 1 | MIETYNQTSPRSAATGLPISMKIFMYLLTVFLITQMIGSALFAVYLHRRLDKI EDERNLHEDFVFMKTIQRCNTGERSLSLLNCEEIKSQFEGFVKDIMLNKEETK KENSFEMQKGDQNPQIAAHVISEASSKTTSVLQWAEKGYYTMSNNLVTLENGK QLTVKRQGLYYIYAQVTFCSNREASSQAPFIASLCLKSPGRFERILLRAANTH SSAKPCGQQSIHLGGVFELQPGASVFVNVTDPSQVSHGTGFTSFGLLKL |
| hCD40 (uniprot Q6P2H9) | 2 | MVRLPLQCVLWGCLLTAVHPEPPTACREKQYLINSQCCSLCQPGQKLVSDCTE FTETECLPCGESEFLDTWNRETHFHQHKYCDPNLGLRVQQKGTSETDTICTCE EGWHCTSEACESCVLHRSCSPGFGVKQIDICQPHFPKDRGLNLLM |
| Ref A | 16 | HHHHHHEVQLVESGGGLVQPGNSLRLSCAASGFTFSSFGMSWVRQAPGKGLEW VSSISGSGSDTLYADSVKGRFTISRDNAKTTLYLQMNSLRPEDTAVYYCTIGG SLSRSSQGTLVTVSS |
| Ref B | 17 | HHHHHHEVQLVESGGGLVQPGNSLRLSCAASGFTFSSFGMSWVRQAPGKGLEW VSSISGSGSDTLYADSVKGRFTISRDNAKTTLYLQMNSLRPEDTAVYYCTIGG SLSRSSQGTLVTVSSA |
| MYC-HIS tag | 30 | AAAEQKLISEEDLNGAAHHHHHH |
| FLAG3-HIS6 tag | 31 | AAADYKDHDGDYKDHDIDYKDDDDKGAAHHHHHH |

TABLE A-1

Amino acid sequences of anti-CD40L constructs ("ID" refers to the SEQ ID NO as used herein)

| Name | ID | Sequence |
|---|---|---|
| C01000 28B02 | 3 | EVQLVESGGGLVQPGGSLRLSCAASGFTLEYYAIGWFRQAPGKEREGVSCISSEGSTSYTDSVKGRFTISR DNAKNTVYLQMNSLKPEDTAVYYCATDPDRGFLGSSCDTQSHQYDYWGQGTLVTVSS |
| C01000 29C10 | 4 | EVQLVESGGGLVQPGGSLRLSCAASGFTLDYYALGWFRQAPGKEREGVSCISSTESSDGSTYYADSVKGRF TISRDSAKNTVYLQMNSLKPEDTAVYYCATDQTLFGVCRGIATPDPGFWGQGTLVTVSS |
| C01000 44B07 | 5 | EVQLVESGGGLVQPGGRLRLSCAASGFTLDYYALAWFRQAPGKEREGVSCISSSEGSTDYADYADSVKGRF TISRDTAKNTVYLQMNNLKPEDTAVYYCATDETTFFSGSCTLSAATFGSWGQGTLVTVSS |
| C01000 46B03 | 6 | EVQLVESGGGLVQAGGSLRLSCAASGRTPLNYHMAWFRQAPGKEREFVAAISSLLGSTDYSDSLKDRFTIS RDNAKATLYLRMNNLKPEDTAVYYCAARETTHYSTSDRVNEMRHYDYWGQGTLVTVSS |
| C01000 2366 [28B02] | 7 | EVQLVESGGGLVQPGGSLRLSCAASGFTLEYYAIGWFRQAPGKEREGVSCISSEGSTSYADSVKGRFTISR DNSKNTVYLQMNSLRPEDTAVYYCATDPDRGFLGSSCDTQSHQYDFWGQGTLVTVSS |
| C01000 3320 28B02-Alb129 | 80 | DVQLVESGGGLVQPGGSLRLSCAASGFTLEYYAIGWFRQAPGKEREGVSCISSEGSTSYADSVKGRFTISR DNSKNTVYLQMNSLRPEDTAVYYCATDPDRGFLGSSCDTQSHQYDFWGQGTLVTVSSGGGGSGGGGSGGGG SGGGGSEVQLVESGGGVVQPGNSLRLSCAASGFTFSSFGMSWVRQAPGKGLEWVSSISGSGSDTLYADSVK GRFTISRDNAKTTLYLQMNSLRPEDTATYYCTIGGSLSRSSQGTLVTVSSA |
| C01000 3323 28B02-Alb23 | 81 | DVQLVESGGGLVQPGGSLRLSCAASGFTLEYYAIGWFRQAPGKEREGVSCISSEGSTSYADSVKGRFTISR DNSKNTVYLQMNSLRPEDTAVYYCATDPDRGFLGSSCDTQSHQYDFWGQGTLVTVSSGGGGSGGGGSGGGG SGGGGSEVQLVESGGGVVQPGGSLRLSCAASGFTFRSFGMSWVRQAPGKGPEWVSSISGSGSDTLYADSVK GRFTISRDNSKNTLYLQMNSLRPEDTATYYCTIGGSLSRSSQGTLVTVSSA |

TABLE A-1-continued

Amino acid sequences of anti-CD40L constructs ("ID" refers to the SEQ ID NO as used herein)

| Name | ID | Sequence |
|---|---|---|
| C01000 3326 28B02- Alb11 | 82 | DVQLVESGGGLVQPGGSLRLSCAASGFTLEYYAIGWFRQAPGKEREGVSCISSEGSTSYADSVKGRFTISR DNSKNTVYLQMNSLRPEDTAVYYCATDPDRGFLGSSCDTQSHQYDFWGQGTLVTVSSGGGGSGGGGSGGGG SGGGGSEVQLVESGGGLVQPGNSLRLSCAASGFTFSSFGMSWVRQAPGKGLEWVSSISGSGSDTLYADSVK GRFTISRDNAKTTLYLQMNSLRPEDTAVYYCTIGGSLSRSSQGTLVTVKSA |
| C01000 3290 [46B03] | 8 | DVQLVESGGGLVQPGGSLRLSCAASGRTPLNYHMAWFRQAPGKEREFVAAISSLLGSTDYADSVKGRFTIS RDNSKTTLYLQMNSLRPEDTAVYYCAARETTHISTSDRVNEIRNYDYWGQGTLVTVSS |
| C01000 3318 46B03-Alb | 9 | DVQLVESGGGLVQPGGSLRLSCAASGRTPLNYHMAWFRQAPGKEREFVAAISSLLGSTDYADSVKGRFTIS RDNSKTTLYLQMNSLRPEDTAVYYCAARETTHISTSDRVNEIRNYDYWGQGTLVTVSSGGGGSGGGSEVQL VESGGGLVQPGNSLRLSCAASGFTFSSFGMSWVRQAPGKGLEWVSSISGSGSDTLYADSVKGRFTISRDNA KTTLYLQMNSLRPEDTAVYYCTIGGSLSRSSQGTLVTVKSA |
| C01000 3313 46B03-Alb | 78 | DVQLVESGGGLVQPGGSLRLSCAASGRTPLNYHMAWFRQAPGKEREFVAAISSLLGSTDYADSVKGRFTIS RDNSKTTLYLQMNSLRPEDTAVYYCAARETTHISTSDRVNEIRNYDYWGQGTLVTVSS GGGGSGGGS EVQLVESGGGVVQPGNSLRLSCAASGFTFSSFGMSWVRQAPGKGLEWVSSISGSGSDTLYADSVKGRFTIS RDNAKTTLYLQMNSLRPEDTATYYCTIGGSLSRSSQGTLVTVSSA |
| C01000 3315 46B03-Alb | 79 | DVQLVESGGGLVQPGGSLRLSCAASGRTPLNYHMAWFRQAPGKEREFVAAISSLLGSTDYADSVKGRFTIS RDNSKTTLYLQMNSLRPEDTAVYYCAARETTHISTSDRVNEIRNYDYWGQGTLVTVSS GGGGSGGGS EVQLVESGGGVVQPGSLRLSCAASGFTFRSFGMSWVRQAPGKGPEWVSSISGSGSDTLYADSVKGRFTIS RDNSKNTLYLQMNSLRPEDTATYYCTIGGSLSRSSQGTLVTVSSA |

TABLE A-2

Sequences for CDRs and frameworks, plus preferred combinations as provided in formula I, namely FR1-CDR1-FR2-CDR2-FR3-CDR3-FR4 (the following terms: "ID" refers to the given SEQ ID NO.; the first column refers to ID of the whole ISVD)

| ID | construct ID | FR1 | ID | CDR1 | ID | FR2 | ID | CDR2 | ID | FR3 | ID | CDR3 | ID | FR4 |
|---|---|---|---|---|---|---|---|---|---|---|---|---|---|---|
| 3 | C01000 28B02 | EVQLVESGGGLVQP GGSLRLSCAAS | 39 | GFTLEYYA IG | 40 | WFRQAPGKE REGVS | 41 | CISSEGS TS | 42 | YTDSVKGRFTISRDNA KNTVYLQMNSLKPEDT AVYYCAT | 43 | DPDRGFLGSS CDTQSHQYDY | 44 | WGQGTLVTV SS | 45 |
| 4 | C01000 29C10 | EVQLVESGGGLVQP GGSLRLSCAAS | 46 | GFTLDYYA LG | 47 | WFRQAPGKE REGVS | 48 | CISSTES SDGSTY | 49 | YADSVKGRFTISRDSA KNTVYLQMNSLKPEDT AVYYCAT | 50 | DQTLFGVCRG IATPDPGF | 51 | WGQGTLVTV SS | 52 |
| 5 | C01000 44B07 | EVQLVESGGGLVQP GGRLRLSCAAS | 53 | GFTLDYYA LA | 54 | WFRQAPGKE REGVS | 55 | CISSSEG STDYAD | 56 | YADSVKGRFTISRDTA KNTVYLQMNNLKPEDT AVYYCAT | 57 | DETTFFSGSC TLSAATFGS | 58 | WGQGTLVTV SS | 59 |
| 6 | C01000 46B03 | EVQLVESGGGLVQA GGSLRLSCAAS | 60 | GRTPLNYH MA | 61 | WFRQAPGKE REFVA | 62 | AISSLLG STD | 63 | YSDSLKDRFTISRDNA KATLYLRMNNLKPEDT AVYYCAA | 64 | RETTHYSTSD RVNEMRHYDY | 65 | WGQGTLVTV SS | 66 |
| 7 | C01000 2366 (28B02) | DVQLVESGGGLVQP GGSLRLSCAAS | 67 | GFTLEYYA IG | 68 | WFRQAPGKE REGVS | 69 | CISEGS TS | 70 | YADSVKGRFTISRDNS KNTVYLQMNSLRPEDT AVYYCAT | 71 | DPDRGFLGSS CDTQSHQYDF | 72 | WGQGTLVTV SS | 73 |
| 8 | C01000 3290 (46B03) | DVQLVESGGGLVQP GGSLRLSCAAS | 32 | GRTPLNYH MA | 34 | WFRQAPGKE REFVA | 35 | AISSLLG STD | 36 | YADSVKGRFTISRDNS KTTLYLQMNSLRPEDT AVYYCAA | 37 | RETTHISTSD RVNEIRNYDY | 38 | WGQGTLVTV SS | 38 |

TABLE A-3

Amino acid sequences of ISVD binding serum albumin (Alb-Nanobodies; "ID" refers to the SEQ ID NO as used herein), including the CDR sequences

| Name | ID | Sequence |
|---|---|---|
| ALB8 (Myc-His6) | 10 | EVQLVESGGGLVQPGNSLRLSCAASGFTFSSFGMSWVRQAPGKGLEWVSSISGSGSDTLYADSVKGRFTISRDNAKT TLYLQMNSLRPEDTAVYYCTIGGSLSRSSQGTLVTVSSAAAEQKLISEEDLNGAAHHHHHH |
| Alb8 | 11 | EVQLVESGGGLVQPGNSLRLSCAASGFTFSSFGMSWVRQAPGKGLEWVSSISGSGSDTLYADSVKGRFTISRDNAKT TLYLQMNSLRPEDTAVYYCTIGGSLSRSSQGTLVTVSS |
| Alb23 | 12 | EVQLLESGGGLVQPGGSLRLSCAASGFTFRSFGMSWVRQAPGKGPEWVSSISGSGSDTLYADSVKGRFTISRDNSKN TLYLQMNSLRPEDTAVYYCTIGGSLSRSSQGTLVTVSS |
| Alb129 | 13 | EVQLVESGGGVVQPGNSLRLSCAASGFTFSSFGMSWVRQAPGKGLEWVSSISGSGSDTLYADSVKGRFTISRDNAKT TLYLQMNSLRPEDTATYYCTIGGSLSRSSQGTLVTVSSA |
| Alb132 | 14 | EVQLVESGGGVVQPGGSLRLSCAASGFTFRSFGMSWVRQAPGKGPEWVSSISGSGSDTLYADSVKGRFTISRDNSKN TLYLQMNSLRPEDTATYYCTIGGSLSRSSQGTLVTVSSA |
| Alb11(S112K)-A (ALB135) | 15 | EVQLVESGGGLVQPGNSLRLSCAASGFTFSSFGMSWVRQAPGKGLEWVSSISGSGSDTLYADSVKGRFTISRDNAKT TLYLQMNSLRPEDTAVYYCTIGGSLSRSSQGTLVTVKSA |
| ALB CDR1 | 74 | SFGMS |
| ALB CDR2 | 75 | SISGSGSDTLYADSVKG |
| ALB CDR3 | 76 | GGSLSR |

TABLE 6.9.1 comparison of mutations at positions 11 and 112 to a C-terminal alanine extension on binding of pre-existing antibodies present in sera from SLE patients

| | Serum samples obtained from SLE patients | | | | | | | | Plasma samples obtained from healthy volunteers | |
|---|---|---|---|---|---|---|---|---|---|---|
| Average binding on Reference A (RU) | | | | | | | | | | |
| Reference A | 45 | 61 | 38 | 40 | 43 | 20 | 69 | 128 | 171 | |
| Inhibition compared to binding on Reference A (%) | | | | | | | | | | |
| Reference B | 20 | 16 | 13 | 45 | 53 | 86 | 101 | 95 | 90 | |
| Reference A (L11E) | 63 | 88 | 117 | 61 | 87 | 88 | 92 | 68 | 21 | |
| Reference A (L11K) | 87 | 97 | 107 | 54 | 106 | 79 | 102 | 100 | 61 | |
| Reference A (L11V) | 68 | 84 | 49 | 56 | 95 | 91 | 21 | 23 | 6 | |
| Reference A (L11Y) | 27 | 71 | 111 | 37 | 84 | 74 | 72 | 13 | 3 | |
| Reference A (S112E) | 13 | 56 | 91 | 77 | 74 | 91 | 94 | 84 | 22 | |
| Reference A (S112F) | −6 | 18 | 26 | −13 | 62 | 69 | 117 | 74 | 43 | |
| Reference A (S112K) | 71 | 77 | 105 | 80 | 116 | 86 | 120 | 87 | 62 | |
| Reference A (S112L) | −36 | 36 | 48 | −24 | 123 | 19 | 84 | 91 | 3 | |

TABLE 6.9.2(a)

influence of different mutations of binding by pre-existing antibodies in samples obtained from SLE patients and human volunteers

| | Mutation(s) | | | | | Samples obtained from SLE patients | | | | Sample obtained from healthy volunteer |
|---|---|---|---|---|---|---|---|---|---|---|
| | L11K | L11V | V89T | S112K | 114A | SLE25 | SLE37 | SLE39 | SLE41 | NB13025-14 | 004-030-ABL-02 |
| Average binding to Reference A | | | | | | | | | | | |
| Average binding for Reference A | | | | | | 38 | 66 | 30 | 41 | 45 | 175 |
| Inhibition compared to average binding to Reference A captured on HSA (%) | | | | | | | | | | | |
| Reference A + V89T, no C-terminal extension | | | x | | x | 100 | 98 | 100 | 100 | 98 | 9 |

TABLE 6.9.2(a)-continued influence of different mutations of binding by pre-existing antibodies in samples obtained from SLE patients and human volunteers

| | Mutation(s) | | | | Samples obtained from SLE patients | | | | | Sample obtained from healthy volunteer |
|---|---|---|---|---|---|---|---|---|---|---|
| | L11K | L11V | V89T | S112K | 114A | SLE25 | SLE37 | SLE39 | SLE41 | NB13025-14 | 004-030-ABL-02 |
| Reference A + V89T + C-terminal alanine | | x | x | | x | 97 | 98 | 100 | 98 | 100 | 100 |
| Reference A + S112K, no C-terminal extension | X | | | x | | 100 | 100 | 100 | 100 | 98 | 100 |
| Reference A + S 112K + C-terminal alanine | X | | | x | x | 100 | 100 | 100 | 99 | 99 | 100 |

TABLE 6.9.2(b)

influence of different mutations of binding by pre-existing antibodies in samples obtained from SLE patients and human volunteers

| | Mutation | | | | Samples obtained from SLE patients | | | | | Sample obtained from healthy volunteer |
|---|---|---|---|---|---|---|---|---|---|---|
| | L11V | V89T | S112Q | 114A | SLE25 | SLE37 | SLE39 | SLE41 | NB13025-14 | 004-030-ABL-02 |
| Average binding to Reference A | | | | | | | | | | |
| Average binding for Reference A | | | | | ND | 71 | 51 | ND | 41 | 180 |
| Inhibition compared to average binding to Reference A captured on HSA (%) | | | | | | | | | | |
| Reference A + V89L + S 112Q + C-terminal alanine | | x | x | x | ND | 100 | 100 | ND | 100 | 97 |
| Reference A + L11V + S 112Q + C-terminal alanine | x | | x | x | ND | 100 | 100 | ND | 100 | 99 |
| Reference A + S 112Q + C-terminal alanine | | | x | x | ND | 92 | 85 | ND | 94 | 100 |

TABLE 6.9.3(a)

influence of different mutations on binding by pre-existing antibodies in samples from SLE patients and human volunteers

| | Mutation(s) | | | | | Samples obtained from SLE patients | | | | Sample obtained healthy volunteer |
|---|---|---|---|---|---|---|---|---|---|---|
| | L11V | V89L | V89T | S112K | 114A | SLE25 | SLE37 | SLE39 | SLE41 | NB13025-14 | 004-030-ABL-02 |
| Average binding to Reference A | | | | | | | | | | | |
| Reference A | | | | | | 28 | 44 | 26 | 33 | 30 | 151 |
| Inhibition compared to average binding to Reference A captured on HSA (%) | | | | | | | | | | | |
| Reference A + V89L, no C-terminal extension | | x | | | | 77 | 64 | 53 | 63 | 41 | 35 |
| Reference A + V89L + C-terminal alanine | | x | | | x | 35 | 27 | 63 | 42 | 46 | 83 |
| Reference A + V89T, no C-terminal extension | | | x | | | 68 | 12 | 84 | 100 | 71 | 11 |
| Reference A + V89T + C-terminal alanine | | | x | | x | 46 | 35 | 71 | 100 | 97 | 99 |
| Reference A + V89T + L11V, no C-terminal extension | x | | x | | | 100 | 97 | 100 | 100 | 100 | 16 |
| Reference A + V89T + L11V + C-terminal alanine | x | | x | | x | 100 | 100 | 100 | 100 | 100 | 67 |

TABLE 6.9.3(a)-continued influence of different mutations on binding by pre-existing antibodies in samples from SLE patients and human volunteers

| | Mutation(s) | | | | | Samples obtained from SLE patients | | | | | Sample obtained healthy volunteer |
|---|---|---|---|---|---|---|---|---|---|---|---|
| | L11V | V89L | V89T | S112K | 114A | SLE25 | SLE37 | SLE39 | SLE41 | NB13025-14 | 004-030-ABL-02 |
| Reference A + S112K + V89L,

```
Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
            245                 250                 255

Gly Leu Leu Lys Leu
            260

<210> SEQ ID NO 2
<211> LENGTH: 151
<212> TYPE: PRT
<213> ORGANISM: Artificial Sequence
<220> FEATURE:
<223> OTHER INFORMATION: hCD40

<400> SEQUENCE: 2

Met Val Arg Leu Pro Leu Gln Cys Val Leu Trp Gly Cys Leu Leu Thr
1               5                   10                  15

Ala Val His Pro Glu Pro Pro Thr Ala Cys Arg Glu Lys Gln Tyr Leu
            20                  25                  30

Ile Asn Ser Gln Cys Cys Ser Leu Cys Gln Pro Gly Gln Lys Leu Val
        35                  40                  45

Ser Asp Cys Thr Glu Phe Thr Glu Thr Glu Cys Leu Pro Cys Gly Glu
    50                  55                  60

Ser Glu Phe Leu Asp Thr Trp Asn Arg Glu Thr His Phe His Gln His
65                  70                  75                  80

Lys Tyr Cys Asp Pro Asn Leu Gly Leu Arg Val Gln Gln Lys Gly Thr
                85                  90                  95

Ser Glu Thr Asp Thr Ile Cys Thr Cys Glu Glu Gly Trp His Cys Thr
            100                 105                 110

Ser Glu Ala Cys Glu Ser Cys Val Leu His Arg Ser Cys Ser Pro Gly
        115                 120                 125

Phe Gly Val Lys Gln Ile Asp Ile Cys Gln Pro His Pro Lys Asp
    130                 135                 140

Arg Gly Leu Asn Leu Leu Met
145                 150

<210> SEQ ID NO 3
<211> LENGTH: 128
<212> TYPE: PRT
<213> ORGANISM: Artificial Sequence
<220> FEATURE:
<223> OTHER INFORMATION: anti-CD40L construct

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Glu Tyr Tyr
            20                  25                  30

Ala Ile Gly Trp Phe Arg Gln Ala Pro Gly Lys Glu Arg Glu Gly Val
        35                  40                  45

Ser Cys Ile Ser Ser Glu Gly Ser Thr Tyr Thr Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Ala
                85                  90                  95
```

Thr Asp Pro Asp Arg Gly Phe Leu Gly Ser Ser Cys Asp Thr Gln Ser
            100                 105                 110

His Gln Tyr Asp Tyr Trp Gly Gln Gly Thr Leu Val Thr Val Ser Ser
        115                 120                 125

<210> SEQ ID NO 4
<211> LENGTH: 130
<212> TYPE: PRT
<213> ORGANISM: Artificial Sequence
<220> FEATURE:
<223> OTHER INFORMATION: anti-CD40L construct

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Asp Tyr Tyr
            20                  25                  30

Ala Leu Gly Trp Phe Arg Gln Ala Pro Gly Lys Glu Arg Glu Gly Val
        35                  40                  45

Ser Cys Ile Ser Ser Thr Glu Ser Ser Asp Gly Ser Thr Tyr Tyr Ala
    50                  55                  60

Asp Ser Val Lys Gly Arg Phe Thr Ile Ser Arg Asp Ser Ala Lys Asn
65                  70                  75                  80

Thr Val Tyr Leu Gln Met Asn Ser Leu Lys Pro Glu Asp Thr Ala Val
                85                  90                  95

Tyr Tyr Cys Ala Thr Asp Gln Thr Leu Phe Gly Val Cys Arg Gly Ile
            100                 105                 110

Ala Thr Pro Asp Pro Gly Phe Trp Gly Gln Gly Thr Leu Val Thr Val
        115                 120                 125

Ser Ser
    130

<210> SEQ ID NO 5
<211> LENGTH: 131
<212> TYPE: PRT
<213> ORGANISM: Artificial Sequence
<220> FEATURE:
<223> OTHER INFORMATION: anti-CD40L construct

<400> SEQUENCE: 5

Glu Val Gln Leu Val Glu Ser Gly Gly Gly Leu Val Gln Pro Gly Gly
1               5                   10                  15

Arg Leu Arg Leu Ser Cys Ala Ala Ser Gly Phe Thr Leu Asp Tyr Tyr
            20                  25                  30

Ala Leu Ala Trp Phe Arg Gln Ala Pro Gly Lys Glu Arg Glu Gly Val
        35                  40                  45

Ser Cys Ile Ser Ser Ser Glu Gly Ser Thr Asp Tyr Ala Asp Tyr Ala
    50                  55                  60

Asp Ser Val Lys Gly Arg Phe Thr Ile Ser Arg Asp Thr Ala Lys Asn
65                  70                  75                  80

Thr Val Tyr Leu Gln Met Asn Asn Leu Lys Pro Glu Asp Thr Ala Val
                85                  90                  95

Tyr Tyr Cys Ala Thr Asp Glu Thr Thr Phe Phe Ser Gly Ser Cys Thr
            100                 105                 110

Leu Ser Ala Ala Thr Phe Gly Ser Trp Gly Gln Gly Thr Leu Val Thr
        115                 120                 125

Val Ser Ser
    130

```
<210> SEQ ID NO 6
<211> LENGTH: 129
<212> TYPE: PRT
<213> ORGANISM: Artificial Sequence
<220> FEATURE:
<223> OTHER INFORMATION: anti-CD40L construct

<400> SEQUENCE: 6

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Pro Leu Asn Tyr
            20                  25                  30

His Met Ala Trp Phe Arg Gln Ala Pro Gly Lys Glu Arg Glu Phe Val
        35                  40                  45

Ala Ala Ile Ser Ser Leu Leu Gly Ser Thr Asp Tyr Ser Asp Ser Leu
    50                  55                  60

Lys Asp Arg Phe Thr Ile Ser Arg Asp Asn Ala Lys Ala Thr Leu Tyr
65                  70                  75                  80

Leu Arg Met Asn Asn Leu Lys Pro Glu Asp Thr Ala Val Tyr Tyr Cys
                85                  90                  95

Ala Ala Arg Glu Thr Thr His Tyr Ser Thr Ser Asp Arg Val Asn Glu
            100                 105                 110

Met Arg His Tyr Asp Tyr Trp Gly Gln Gly Thr Leu Val Thr Val Ser
        115                 120                 125

Ser

<210> SEQ ID NO 7
<211> LENGTH: 128
<212> TYPE: PRT
<213> ORGANISM: Artificial Sequence
<220> FEATURE:
<223> OTHER INFORMATION: anti-CD40L construct

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Glu Tyr Tyr
            20                  25                  30

Ala Ile Gly Trp Phe Arg Gln Ala Pro Gly Lys Glu Arg Glu Gly Val
        35                  40                  45

Ser Cys Ile Ser Ser Glu Gly Ser Thr Ser Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Val Tyr Tyr Cys Ala
                85                  90                  95

Thr Asp Pro Asp Arg Gly Phe Leu Gly Ser Ser Cys Asp Thr Gln Ser
            100                 105                 110

His Gln Tyr Asp Phe Trp Gly Gln Gly Thr Leu Val Thr Val Ser Ser
        115                 120                 125

<210> SEQ ID NO 8
<211> LENGTH: 129
<212> TYPE: PRT
<213> ORGANISM: Artificial Sequence
<220> FEATURE:
<223> OTHER INFORMATION: anti-CD40L construct
```

<400> SEQUENCE: 8

Asp Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Pro Leu Asn Tyr
            20                  25                  30

His Met Ala Trp Phe Arg Gln Ala Pro Gly Lys Glu Arg Glu Phe Val
        35                  40                  45

Ala Ala Ile Ser Ser Leu Leu Gly Ser Thr Asp Tyr Ala Asp Ser Val
    50                  55                  60

Lys Gly Arg Phe Thr Ile Ser Arg Asp Asn Ser Lys Thr Thr Leu Tyr
65                  70                  75                  80

Leu Gln Met Asn Ser Leu Arg Pro Glu Asp Thr Ala Val Tyr Tyr Cys
                85                  90                  95

Ala Ala Arg Glu Thr Thr His Ile Ser Thr Ser Asp Arg Val Asn Glu
            100                 105                 110

Ile Arg Asn Tyr Asp Tyr Trp Gly Gln Gly Thr Leu Val Thr Val Ser
        115                 120                 125

Ser

<210> SEQ ID NO 9
<211> LENGTH: 254
<212> TYPE: PRT
<213> ORGANISM: Artificial Sequence
<220> FEATURE:
<223> OTHER INFORMATION: anti-CD40L construct

<400> SEQUENCE: 9

Asp Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Pro Leu Asn Tyr
            20                  25                  30

His Met Ala Trp Phe Arg Gln Ala Pro Gly Lys Glu Arg Glu Phe Val
        35                  40                  45

Ala Ala Ile Ser Ser Leu Leu Gly Ser Thr Asp Tyr Ala Asp Ser Val
    50                  55                  60

Lys Gly Arg Phe Thr Ile Ser Arg Asp Asn Ser Lys Thr Thr Leu Tyr
65                  70                  75                  80

Leu Gln Met Asn Ser Leu Arg Pro Glu Asp Thr Ala Val Tyr Tyr Cys
                85                  90                  95

Ala Ala Arg Glu Thr Thr His Ile Ser Thr Ser Asp Arg Val Asn Glu
            100                 105                 110

Ile Arg Asn Tyr Asp Tyr Trp Gly Gln Gly Thr Leu Val Thr Val Ser
        115                 120                 125

Ser Gly Gly Gly Gly Ser Gly Gly Gly Ser Glu Val Gln Leu Val Glu
    130                 135                 140

Ser Gly Gly Gly Leu Val Gln Pro Gly Asn Ser Leu Arg Leu Ser Cys
145                 150                 155                 160

Ala Ala Ser Gly Phe Thr Phe Ser Ser Phe Gly Met Ser Trp Val Arg
                165                 170                 175

Gln Ala Pro Gly Lys Gly Leu Glu Trp Val Ser Ser Ile Ser Gly Ser
            180                 185                 190

Gly Ser Asp Thr Leu Tyr Ala Asp Ser Val Lys Gly Arg Phe Thr Ile
        195                 200                 205

Ser Arg Asp Asn Ala Lys Thr Thr Leu Tyr Leu Gln Met Asn Ser Leu
    210                 215                 220

```
Arg Pro Glu Asp Thr Ala Val Tyr Tyr Cys Thr Ile Gly Gly Ser Leu
225                 230                 235                 240

Ser Arg Ser Ser Gln Gly Thr Leu Val Thr Val Lys Ser Ala
            245                 250

<210> SEQ ID NO 10
<211> LENGTH: 138
<212> TYPE: PRT
<213> ORGANISM: Artificial Sequence
<220> FEATURE:
<223> OTHER INFORMATION: ISVD binding serum albumin

<400> SEQUENCE: 10

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser Ala Ala Ala Glu Gln Lys Leu Ile Ser Glu Glu Asp Leu
        115                 120                 125

Asn Gly Ala Ala His His His His His His
    130                 135

<210> SEQ ID NO 11
<211> LENGTH: 115
<212> TYPE: PRT
<213> ORGANISM: Artificial Sequence
<220> FEATURE:
<223> OTHER INFORMATION: ISVD binding serum albumin

<400> SEQUENCE: 11

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115
```

<210> SEQ ID NO 12
<211> LENGTH: 115
<212> TYPE: PRT
<213> ORGANISM: Artificial Sequence
<220> FEATURE:
<223> OTHER INFORMATION: ISVD binding serum albumin

<400> SEQUENCE: 12

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 13
<211> LENGTH: 116
<212> TYPE: PRT
<213> ORGANISM: Artificial Sequence
<220> FEATURE:
<223> OTHER INFORMATION: ISVD binding serum albumin

<400> SEQUENCE: 13

Glu Val Gln Leu Val Glu Ser Gly Gly Gly Val Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Thr Tyr Tyr Cys
                85                  90                  95

Thr Ile Gly Gly Ser Leu Ser Arg Ser Ser Gln Gly Thr Leu Val Thr
            100                 105                 110

Val Ser Ser Ala
        115

<210> SEQ ID NO 14
<211> LENGTH: 116
<212> TYPE: PRT
<213> ORGANISM: Artificial Sequence
<220> FEATURE:
<223> OTHER INFORMATION: ISVD binding serum albumin

```
<400> SEQUENCE: 14

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Thr Tyr Tyr Cys
                85                  90                  95

Thr Ile Gly Gly Ser Leu Ser Arg Ser Ser Gln Gly Thr Leu Val Thr
            100                 105                 110

Val Ser Ser Ala
        115

<210> SEQ ID NO 15
<211> LENGTH: 116
<212> TYPE: PRT
<213> ORGANISM: Artificial Sequence
<220> FEATURE:
<223> OTHER INFORMATION: ISVD binding serum albumin

<400> SEQUENCE: 15

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Lys Ser Ala
        115

<210> SEQ ID NO 16
<211> LENGTH: 121
<212> TYPE: PRT
<213> ORGANISM: Artificial Sequence
<220> FEATURE:
<223> OTHER INFORMATION: Ref A

<400> SEQUENCE: 16

His His His His His His Glu Val Gln Leu Val Glu Ser Gly Gly Gly
1               5                   10                  15

Leu Val Gln Pro Gly Asn Ser Leu Arg Leu Ser Cys Ala Ala Ser Gly
            20                  25                  30

Phe Thr Phe Ser Ser Phe Gly Met Ser Trp Val Arg Gln Ala Pro Gly
        35                  40                  45
```

```
Lys Gly Leu Glu Trp Val Ser Ser Ile Ser Gly Ser Gly Ser Asp Thr
 50                  55                  60
Leu Tyr Ala Asp Ser Val Lys Gly Arg Phe Thr Ile Ser Arg Asp Asn
 65                  70                  75                  80
Ala Lys Thr Thr Leu Tyr Leu Gln Met Asn Ser Leu Arg Pro Glu Asp
                 85                  90                  95
Thr Ala Val Tyr Tyr Cys Thr Ile Gly Gly Ser Leu Ser Arg Ser Ser
                100                 105                 110
Gln Gly Thr Leu Val Thr Val Ser Ser
            115                 120
```

<210> SEQ ID NO 17
<211> LENGTH: 122
<212> TYPE: PRT
<213> ORGANISM: Artificial Sequence
<220> FEATURE:
<223> OTHER INFORMATION: Ref B

<400> SEQUENCE: 17

```
His His His His His His Glu Val Gln Leu Val Glu Ser Gly Gly Gly
 1               5                  10                  15
Leu Val Gln Pro Gly Asn Ser Leu Arg Leu Ser Cys Ala Ala Ser Gly
            20                  25                  30
Phe Thr Phe Ser Ser Phe Gly Met Ser Trp Val Arg Gln Ala Pro Gly
         35                 40                  45
Lys Gly Leu Glu Trp Val Ser Ser Ile Ser Gly Ser Gly Ser Asp Thr
 50                  55                  60
Leu Tyr Ala Asp Ser Val Lys Gly Arg Phe Thr Ile Ser Arg Asp Asn
 65                  70                  75                  80
Ala Lys Thr Thr Leu Tyr Leu Gln Met Asn Ser Leu Arg Pro Glu Asp
                 85                  90                  95
Thr Ala Val Tyr Tyr Cys Thr Ile Gly Gly Ser Leu Ser Arg Ser Ser
                100                 105                 110
Gln Gly Thr Leu Val Thr Val Ser Ser Ala
            115                 120
```

<210> SEQ ID NO 18
<211> LENGTH: 5
<212> TYPE: PRT
<213> ORGANISM: Artificial Sequence
<220> FEATURE:
<223> OTHER INFORMATION: Linker sequence

<400> SEQUENCE: 18

```
Gly Gly Gly Gly Ser
 1               5
```

<210> SEQ ID NO 19
<211> LENGTH: 7
<212> TYPE: PRT
<213> ORGANISM: Artificial Sequence
<220> FEATURE:
<223> OTHER INFORMATION: Linker sequence

<400> SEQUENCE: 19

```
Ser Gly Gly Ser Gly Gly Ser
 1               5
```

```
<210> SEQ ID NO 20
<211> LENGTH: 8
<212> TYPE: PRT
<213> ORGANISM: Artificial Sequence
<220> FEATURE:
<223> OTHER INFORMATION: Linker sequence

<400> SEQUENCE: 20

Gly Gly Gly Gly Gly Gly Gly Ser
1               5

<210> SEQ ID NO 21
<211> LENGTH: 9
<212> TYPE: PRT
<213> ORGANISM: Artificial Sequence
<220> FEATURE:
<223> OTHER INFORMATION: Linker sequence

<400> SEQUENCE: 21

Gly Gly Gly Gly Ser Gly Gly Gly Ser
1               5

<210> SEQ ID NO 22
<211> LENGTH: 10
<212> TYPE: PRT
<213> ORGANISM: Artificial Sequence
<220> FEATURE:
<223> OTHER INFORMATION: Linker sequence

<400> SEQUENCE: 22

Gly Gly Gly Gly Ser Gly Gly Gly Gly Ser
1               5                   10

<210> SEQ ID NO 23
<211> LENGTH: 15
<212> TYPE: PRT
<213> ORGANISM: Artificial Sequence
<220> FEATURE:
<223> OTHER INFORMATION: Linker sequence

<400> SEQUENCE: 23

Gly Gly Gly Gly Ser Gly Gly Gly Gly Ser Gly Gly Gly Gly Ser
1               5                   10                  15

<210> SEQ ID NO 24
<211> LENGTH: 18
<212> TYPE: PRT
<213> ORGANISM: Artificial Sequence
<220> FEATURE:
<223> OTHER INFORMATION: Linker sequence

<400> SEQUENCE: 24

Gly Gly Gly Gly Ser Gly Gly Gly Gly Ser Gly Gly Gly Gly Gly
1               5                   10                  15

Gly Ser

<210> SEQ ID NO 25
<211> LENGTH: 20
<212> TYPE: PRT
<213> ORGANISM: Artificial Sequence
<220> FEATURE:
<223> OTHER INFORMATION: Linker sequence
```

```
<400> SEQUENCE: 25

Gly Gly Gly Gly Ser Gly Gly Gly Gly Ser Gly Gly Gly Gly Ser Gly
1               5                  10                  15

Gly Gly Gly Ser
            20

<210> SEQ ID NO 26
<211> LENGTH: 25
<212> TYPE: PRT
<213> ORGANISM: Artificial Sequence
<220> FEATURE:
<223> OTHER INFORMATION: Linker sequence

<400> SEQUENCE: 26

Gly Gly Gly Gly Ser Gly Gly Gly Gly Ser Gly Gly Gly Gly Ser Gly
1               5                  10                  15

Gly Gly Gly Ser Gly Gly Gly Gly Ser
            20                  25

<210> SEQ ID NO 27
<211> LENGTH: 30
<212> TYPE: PRT
<213> ORGANISM: Artificial Sequence
<220> FEATURE:
<223> OTHER INFORMATION: Linker sequence

<400> SEQUENCE: 27

Gly Gly Gly Gly Ser Gly Gly Gly Gly Ser Gly Gly Gly Gly Ser Gly
1               5                  10                  15

Gly Gly Gly Ser Gly Gly Gly Gly Ser Gly Gly Gly Gly Ser
            20                  25                  30

<210> SEQ ID NO 28
<211> LENGTH: 35
<212> TYPE: PRT
<213> ORGANISM: Artificial Sequence
<220> FEATURE:
<223> OTHER INFORMATION: Linker sequence

<400> SEQUENCE: 28

Gly Gly Gly Gly Ser Gly Gly Gly Gly Ser Gly Gly Gly Gly Ser Gly
1               5                  10                  15

Gly Gly Gly Ser Gly Gly Gly Gly Ser Gly Gly Gly Gly Ser Gly Gly
            20                  25                  30

Gly Gly Ser
        35

<210> SEQ ID NO 29
<211> LENGTH: 40
<212> TYPE: PRT
<213> ORGANISM: Artificial Sequence
<220> FEATURE:
<223> OTHER INFORMATION: Linker sequencee

<400> SEQUENCE: 29

Gly Gly Gly Gly Ser Gly Gly Gly Gly Ser Gly Gly Gly Gly Ser Gly
1               5                  10                  15

Gly Gly Gly Ser Gly Gly Gly Gly Ser Gly Gly Gly Gly Ser Gly Gly
            20                  25                  30

Gly Gly Ser Gly Gly Gly Gly Ser
        35                  40
```

<210> SEQ ID NO 30
<211> LENGTH: 23
<212> TYPE: PRT
<213> ORGANISM: Artificial Sequence
<220> FEATURE:
<223> OTHER INFORMATION: MYC-HIS tag

<400> SEQUENCE: 30

```
Ala Ala Ala Glu Gln Lys Leu Ile Ser Glu Glu Asp Leu Asn Gly Ala
1               5                   10                  15

Ala His His His His His His
            20
```

<210> SEQ ID NO 31
<211> LENGTH: 34
<212> TYPE: PRT
<213> ORGANISM: Artificial Sequence
<220> FEATURE:
<223> OTHER INFORMATION: FLAG3-HIS6 tag

<400> SEQUENCE: 31

```
Ala Ala Ala Asp Tyr Lys Asp His Asp Gly Asp Tyr Lys Asp His Asp
1               5                   10                  15

Ile Asp Tyr Lys Asp Asp Asp Asp Lys Gly Ala Ala His His His His
            20                  25                  30

His His
```

<210> SEQ ID NO 32
<211> LENGTH: 25
<212> TYPE: PRT
<213> ORGANISM: Artificial Sequence
<220> FEATURE:
<223> OTHER INFORMATION: FR Sequence

<400> SEQUENCE: 32

```
Asp Val Gln Leu Val Glu Ser Gly Gly Gly Leu Val Gln Pro Gly Gly
1               5                   10                  15

Ser Leu Arg Leu Ser Cys Ala Ala Ser
            20                  25
```

<210> SEQ ID NO 33
<211> LENGTH: 10
<212> TYPE: PRT
<213> ORGANISM: Artificial Sequence
<220> FEATURE:
<223> OTHER INFORMATION: CDR Sequence

<400> SEQUENCE: 33

```
Gly Arg Thr Pro Leu Asn Tyr His Met Ala
1               5                   10
```

<210> SEQ ID NO 34
<211> LENGTH: 14
<212> TYPE: PRT
<213> ORGANISM: Artificial Sequence
<220> FEATURE:
<223> OTHER INFORMATION: FR Sequence

<400> SEQUENCE: 34

```
Trp Phe Arg Gln Ala Pro Gly Lys Glu Arg Glu Phe Val Ala
1               5                   10
```

```
<210> SEQ ID NO 35
<211> LENGTH: 10
<212> TYPE: PRT
<213> ORGANISM: Artificial Sequence
<220> FEATURE:
<223> OTHER INFORMATION: CDR Sequence

<400> SEQUENCE: 35

Ala Ile Ser Ser Leu Leu Gly Ser Thr Asp
1               5                   10

<210> SEQ ID NO 36
<211> LENGTH: 39
<212> TYPE: PRT
<213> ORGANISM: Artificial Sequence
<220> FEATURE:
<223> OTHER INFORMATION: FR Sequence

<400> SEQUENCE: 36

Tyr Ala Asp Ser Val Lys Gly Arg Phe Thr Ile Ser Arg Asp Asn Ser
1               5                   10                  15

Lys Thr Thr Leu Tyr Leu Gln Met Asn Ser Leu Arg Pro Glu Asp Thr
            20                  25                  30

Ala Val Tyr Tyr Cys Ala Ala
        35

<210> SEQ ID NO 37
<211> LENGTH: 20
<212> TYPE: PRT
<213> ORGANISM: Artificial Sequence
<220> FEATURE:
<223> OTHER INFORMATION: CDR Sequence

<400> SEQUENCE: 37

Arg Glu Thr Thr His Ile Ser Thr Ser Asp Arg Val Asn Glu Ile Arg
1               5                   10                  15

Asn Tyr Asp Tyr
            20

<210> SEQ ID NO 38
<211> LENGTH: 11
<212> TYPE: PRT
<213> ORGANISM: Artificial Sequence
<220> FEATURE:
<223> OTHER INFORMATION: FR Sequence

<400> SEQUENCE: 38

Trp Gly Gln Gly Thr Leu Val Thr Val Ser Ser
1               5                   10

<210> SEQ ID NO 39
<211> LENGTH: 25
<212> TYPE: PRT
<213> ORGANISM: Artificial Sequence
<220> FEATURE:
<223> OTHER INFORMATION: FR Sequence

<400> SEQUENCE: 39

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25
```

```
<210> SEQ ID NO 40
<211> LENGTH: 10
<212> TYPE: PRT
<213> ORGANISM: Artificial Sequence
<220> FEATURE:
<223> OTHER INFORMATION: CDR Sequence

<400> SEQUENCE: 40

Gly Phe Thr Leu Glu Tyr Tyr Ala Ile Gly
1               5                   10

<210> SEQ ID NO 41
<211> LENGTH: 14
<212> TYPE: PRT
<213> ORGANISM: Artificial Sequence
<220> FEATURE:
<223> OTHER INFORMATION: FR Sequence

<400> SEQUENCE: 41

Trp Phe Arg Gln Ala Pro Gly Lys Glu Arg Glu Gly Val Ser
1               5                   10

<210> SEQ ID NO 42
<211> LENGTH: 9
<212> TYPE: PRT
<213> ORGANISM: Artificial Sequence
<220> FEATURE:
<223> OTHER INFORMATION: CDR Sequence

<400> SEQUENCE: 42

Cys Ile Ser Ser Glu Gly Ser Thr Ser
1               5

<210> SEQ ID NO 43
<211> LENGTH: 39
<212> TYPE: PRT
<213> ORGANISM: Artificial Sequence
<220> FEATURE:
<223> OTHER INFORMATION: FR Sequence

<400> SEQUENCE: 43

Tyr Thr Asp Ser Val Lys Gly Arg Phe Thr Ile Ser Arg Asp Asn Ala
1               5                   10                  15

Lys Asn Thr Val Tyr Leu Gln Met Asn Ser Leu Lys Pro Glu Asp Thr
            20                  25                  30

Ala Val Tyr Tyr Cys Ala Thr
        35

<210> SEQ ID NO 44
<211> LENGTH: 20
<212> TYPE: PRT
<213> ORGANISM: Artificial Sequence
<220> FEATURE:
<223> OTHER INFORMATION: CDR Sequence

<400> SEQUENCE: 44

Asp Pro Asp Arg Gly Phe Leu Gly Ser Ser Cys Asp Thr Gln Ser His
1               5                   10                  15

Gln Tyr Asp Tyr
            20

<210> SEQ ID NO 45
<211> LENGTH: 11
<212> TYPE: PRT
<213> ORGANISM: Artificial Sequence
```

<220> FEATURE:
<223> OTHER INFORMATION: FR Sequence

<400> SEQUENCE: 45

Trp Gly Gln Gly Thr Leu Val Thr Val Ser Ser
1               5                   10

<210> SEQ ID NO 46
<211> LENGTH: 25
<212> TYPE: PRT
<213> ORGANISM: Artificial Sequence
<220> FEATURE:
<223> OTHER INFORMATION: FR Sequence

<400> SEQUENCE: 46

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 47
<211> LENGTH: 10
<212> TYPE: PRT
<213> ORGANISM: Artificial Sequence
<220> FEATURE:
<223> OTHER INFORMATION: CDR Sequence

<400> SEQUENCE: 47

Gly Phe Thr Leu Asp Tyr Tyr Ala Leu Gly
1               5                   10

<210> SEQ ID NO 48
<211> LENGTH: 14
<212> TYPE: PRT
<213> ORGANISM: Artificial Sequence
<220> FEATURE:
<223> OTHER INFORMATION: FR Sequence

<400> SEQUENCE: 48

Trp Phe Arg Gln Ala Pro Gly Lys Glu Arg Glu Gly Val Ser
1               5                   10

<210> SEQ ID NO 49
<211> LENGTH: 13
<212> TYPE: PRT
<213> ORGANISM: Artificial Sequence
<220> FEATURE:
<223> OTHER INFORMATION: CDR Sequence

<400> SEQUENCE: 49

Cys Ile Ser Ser Thr Glu Ser Ser Asp Gly Ser Thr Tyr
1               5                   10

<210> SEQ ID NO 50
<211> LENGTH: 39
<212> TYPE: PRT
<213> ORGANISM: Artificial Sequence
<220> FEATURE:
<223> OTHER INFORMATION: FR Sequence

```
<400> SEQUENCE: 50

Tyr Ala Asp Ser Val Lys Gly Arg Phe Thr Ile Ser Arg Asp Ser Ala
1               5                   10                  15

Lys Asn Thr Val Tyr Leu Gln Met Asn Ser Leu Lys Pro Glu Asp Thr
            20                  25                  30

Ala Val Tyr Tyr Cys Ala Thr
        35

<210> SEQ ID NO 51
<211> LENGTH: 18
<212> TYPE: PRT
<213> ORGANISM: Artificial Sequence
<220> FEATURE:
<223> OTHER INFORMATION: CDR Sequence

<400> SEQUENCE: 51

Asp Gln Thr Leu Phe Gly Val Cys Arg Gly Ile Ala Thr Pro Asp Pro
1               5                   10                  15

Gly Phe

<210> SEQ ID NO 52
<211> LENGTH: 11
<212> TYPE: PRT
<213> ORGANISM: Artificial Sequence
<220> FEATURE:
<223> OTHER INFORMATION: FR Sequence

<400> SEQUENCE: 52

Trp Gly Gln Gly Thr Leu Val Thr Val Ser Ser
1               5                   10

<210> SEQ ID NO 53
<211> LENGTH: 25
<212> TYPE: PRT
<213> ORGANISM: Artificial Sequence
<220> FEATURE:
<223> OTHER INFORMATION: FR Sequence

<400> SEQUENCE: 53

Glu Val Gln Leu Val Glu Ser Gly Gly Gly Leu Val Gln Pro Gly Gly
1               5                   10                  15

Arg Leu Arg Leu Ser Cys Ala Ala Ser
            20                  25

<210> SEQ ID NO 54
<211> LENGTH: 10
<212> TYPE: PRT
<213> ORGANISM: Artificial Sequence
<220> FEATURE:
<223> OTHER INFORMATION: CDR Sequence

<400> SEQUENCE: 54

Gly Phe Thr Leu Asp Tyr Tyr Ala Leu Ala
1               5                   10

<210> SEQ ID NO 55
<211> LENGTH: 14
<212> TYPE: PRT
<213> ORGANISM: Artificial Sequence
<220> FEATURE:
<223> OTHER INFORMATION: FR Sequence
```

```
<400> SEQUENCE: 55

Trp Phe Arg Gln Ala Pro Gly Lys Glu Arg Glu Gly Val Ser
1               5                   10

<210> SEQ ID NO 56
<211> LENGTH: 13
<212> TYPE: PRT
<213> ORGANISM: Artificial Sequence
<220> FEATURE:
<223> OTHER INFORMATION: CDR Sequence

<400> SEQUENCE: 56

Cys Ile Ser Ser Ser Glu Gly Ser Thr Asp Tyr Ala Asp
1               5                   10

<210> SEQ ID NO 57
<211> LENGTH: 39
<212> TYPE: PRT
<213> ORGANISM: Artificial Sequence
<220> FEATURE:
<223> OTHER INFORMATION: FR Sequence

<400> SEQUENCE: 57

Tyr Ala Asp Ser Val Lys Gly Arg Phe Thr Ile Ser Arg Asp Thr Ala
1               5                   10                  15

Lys Asn Thr Val Tyr Leu Gln Met Asn Asn Leu Lys Pro Glu Asp Thr
            20                  25                  30

Ala Val Tyr Tyr Cys Ala Thr
        35

<210> SEQ ID NO 58
<211> LENGTH: 19
<212> TYPE: PRT
<213> ORGANISM: Artificial Sequence
<220> FEATURE:
<223> OTHER INFORMATION: CDR Sequence

<400> SEQUENCE: 58

Asp Glu Thr Thr Phe Phe Ser Gly Ser Cys Thr Leu Ser Ala Ala Thr
1               5                   10                  15

Phe Gly Ser

<210> SEQ ID NO 59
<211> LENGTH: 11
<212> TYPE: PRT
<213> ORGANISM: Artificial Sequence
<220> FEATURE:
<223> OTHER INFORMATION: FR Sequence

<400> SEQUENCE: 59

Trp Gly Gln Gly Thr Leu Val Thr Val Ser Ser
1               5                   10

<210> SEQ ID NO 60
<211> LENGTH: 25
<212> TYPE: PRT
<213> ORGANISM: Artificial Sequence
<220> FEATURE:
<223> OTHER INFORMATION: FR Sequence
```

```
<400> SEQUENCE: 60

Glu Val Gln Leu Val Glu Ser Gly Gly Gly Leu Val Gln Ala Gly Gly
1               5                   10                  15

Ser Leu Arg Leu Ser Cys Ala Ala Ser
            20                  25

<210> SEQ ID NO 61
<211> LENGTH: 10
<212> TYPE: PRT
<213> ORGANISM: Artificial Sequence
<220> FEATURE:
<223> OTHER INFORMATION: CDR Sequence

<400> SEQUENCE: 61

Gly Arg Thr Pro Leu Asn Tyr His Met Ala
1               5                   10

<210> SEQ ID NO 62
<211> LENGTH: 14
<212> TYPE: PRT
<213> ORGANISM: Artificial Sequence
<220> FEATURE:
<223> OTHER INFORMATION: FR Sequence

<400> SEQUENCE: 62

Trp Phe Arg Gln Ala Pro Gly Lys Glu Arg Glu Phe Val Ala
1               5                   10

<210> SEQ ID NO 63
<211> LENGTH: 10
<212> TYPE: PRT
<213> ORGANISM: Artificial Sequence
<220> FEATURE:
<223> OTHER INFORMATION: CDR Sequence

<400> SEQUENCE: 63

Ala Ile Ser Ser Leu Leu Gly Ser Thr Asp
1               5                   10

<210> SEQ ID NO 64
<211> LENGTH: 39
<212> TYPE: PRT
<213> ORGANISM: Artificial Sequence
<220> FEATURE:
<223> OTHER INFORMATION: FR Sequence

<400> SEQUENCE: 64

Tyr Ser Asp Ser Leu Lys Asp Arg Phe Thr Ile Ser Arg Asp Asn Ala
1               5                   10                  15

Lys Ala Thr Leu Tyr Leu Arg Met Asn Asn Leu Lys Pro Glu Asp Thr
            20                  25                  30

Ala Val Tyr Tyr Cys Ala Ala
        35

<210> SEQ ID NO 65
<211> LENGTH: 20
<212> TYPE: PRT
<213> ORGANISM: Artificial Sequence
<220> FEATURE:
<223> OTHER INFORMATION: CDR Sequence
```

```
<400> SEQUENCE: 65

Arg Glu Thr Thr His Tyr Ser Thr Ser Asp Arg Val Asn Glu Met Arg
1               5                   10                  15

His Tyr Asp Tyr
            20

<210> SEQ ID NO 66
<211> LENGTH: 11
<212> TYPE: PRT
<213> ORGANISM: Artificial Sequence
<220> FEATURE:
<223> OTHER INFORMATION: FR Sequence

<400> SEQUENCE: 66

Trp Gly Gln Gly Thr Leu Val Thr Val Ser Ser
1               5                   10

<210> SEQ ID NO 67
<211> LENGTH: 25
<212> TYPE: PRT
<213> ORGANISM: Artificial Sequence
<220> FEATURE:
<223> OTHER INFORMATION: FR Sequence

<400> SEQUENCE: 67

Asp Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 68
<211> LENGTH: 10
<212> TYPE: PRT
<213> ORGANISM: Artificial Sequence
<220> FEATURE:
<223> OTHER INFORMATION: CDR Sequence

<400> SEQUENCE: 68

Gly Phe Thr Leu Glu Tyr Tyr Ala Ile Gly
1               5                   10

<210> SEQ ID NO 69
<211> LENGTH: 14
<212> TYPE: PRT
<213> ORGANISM: Artificial Sequence
<220> FEATURE:
<223> OTHER INFORMATION: FR Sequence

<400> SEQUENCE: 69

Trp Phe Arg Gln Ala Pro Gly Lys Glu Arg Glu Gly Val Ser
1               5                   10

<210> SEQ ID NO 70
<211> LENGTH: 9
<212> TYPE: PRT
<213> ORGANISM: Artificial Sequence
<220> FEATURE:
<223> OTHER INFORMATION: CDR Sequence

<400> SEQUENCE: 70

Cys Ile Ser Ser Glu Gly Ser Thr Ser
1               5
```

```
<210> SEQ ID NO 71
<211> LENGTH: 39
<212> TYPE: PRT
<213> ORGANISM: Artificial Sequence
<220> FEATURE:
<223> OTHER INFORMATION: FR Sequence

<400> SEQUENCE: 71

Tyr Ala Asp Ser Val Lys Gly Arg Phe Thr Ile Ser Arg Asp Asn Ser
1               5                   10                  15

Lys Asn Thr Val Tyr Leu Gln Met Asn Ser Leu Arg Pro Glu Asp Thr
            20                  25                  30

Ala Val Tyr Tyr Cys Ala Thr
        35

<210> SEQ ID NO 72
<211> LENGTH: 20
<212> TYPE: PRT
<213> ORGANISM: Artificial Sequence
<220> FEATURE:
<223> OTHER INFORMATION: CDR Sequence

<400> SEQUENCE: 72

Asp Pro Asp Arg Gly Phe Leu Gly Ser Ser Cys Asp Thr Gln Ser His
1               5                   10                  15

Gln Tyr Asp Phe
            20

<210> SEQ ID NO 73
<211> LENGTH: 11
<212> TYPE: PRT
<213> ORGANISM: Artificial Sequence
<220> FEATURE:
<223> OTHER INFORMATION: FR Sequence

<400> SEQUENCE: 73

Trp Gly Gln Gly Thr Leu Val Thr Val Ser Ser
1               5                   10

<210> SEQ ID NO 74
<211> LENGTH: 5
<212> TYPE: PRT
<213> ORGANISM: Artificial Sequence
<220> FEATURE:
<223> OTHER INFORMATION: ISVD binding serum albumin CDR Sequence

<400> SEQUENCE: 74

Ser Phe Gly Met Ser
1               5

<210> SEQ ID NO 75
<211> LENGTH: 17
<212> TYPE: PRT
<213> ORGANISM: Artificial Sequence
<220> FEATURE:
<223> OTHER INFORMATION: ISVD binding serum albumin CDR Sequence

<400> SEQUENCE: 75

Ser Ile Ser Gly Ser Gly Ser Asp Thr Leu Tyr Ala Asp Ser Val Lys
1               5                   10                  15

Gly
```

```
<210> SEQ ID NO 76
<211> LENGTH: 6
<212> TYPE: PRT
<213> ORGANISM: Artificial Sequence
<220> FEATURE:
<223> OTHER INFORMATION: ISVD binding serum albumin CDR Sequence

<400> SEQUENCE: 76

Gly Gly Ser Leu Ser Arg
1               5

<210> SEQ ID NO 77
<211> LENGTH: 3
<212> TYPE: PRT
<213> ORGANISM: Artificial Sequence
<220> FEATURE:
<223> OTHER INFORMATION: Linker sequence

<400> SEQUENCE: 77

Ala Ala Ala
1

<210> SEQ ID NO 78
<211> LENGTH: 254
<212> TYPE: PRT
<213> ORGANISM: Artificial Sequence
<220> FEATURE:
<223> OTHER INFORMATION: anti-CD40L construct

<400> SEQUENCE: 78

Asp Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Pro Leu Asn Tyr
            20                  25                  30

His Met Ala Trp Phe Arg Gln Ala Pro Gly Lys Glu Arg Glu Phe Val
        35                  40                  45

Ala Ala Ile Ser Ser Leu Leu Gly Ser Thr Asp Tyr Ala Asp Ser Val
    50                  55                  60

Lys Gly Arg Phe Thr Ile Ser Arg Asp Asn Ser Lys Thr Thr Leu Tyr
65                  70                  75                  80

Leu Gln Met Asn Ser Leu Arg Pro Glu Asp Thr Ala Val Tyr Tyr Cys
                85                  90                  95

Ala Ala Arg Glu Thr Thr His Ile Ser Thr Ser Asp Arg Val Asn Glu
            100                 105                 110

Ile Arg Asn Tyr Asp Tyr Trp Gly Gln Gly Thr Leu Val Thr Val Ser
        115                 120                 125

Ser Gly Gly Gly Gly Ser Gly Gly Gly Ser Glu Val Gln Leu Val Glu
    130                 135                 140

Ser Gly Gly Gly Val Val Gln Pro Gly Asn Ser Leu Arg Leu Ser Cys
145                 150                 155                 160

Ala Ala Ser Gly Phe Thr Phe Ser Ser Phe Gly Met Ser Trp Val Arg
                165                 170                 175

Gln Ala Pro Gly Lys Gly Leu Glu Trp Val Ser Ser Ile Ser Gly Ser
            180                 185                 190

Gly Ser Asp Thr Leu Tyr Ala Asp Ser Val Lys Gly Arg Phe Thr Ile
        195                 200                 205

Ser Arg Asp Asn Ala Lys Thr Thr Leu Tyr Leu Gln Met Asn Ser Leu
    210                 215                 220
```

```
Arg Pro Glu Asp Thr Ala Thr Tyr Tyr Cys Thr Ile Gly Gly Ser Leu
225                 230                 235                 240

Ser Arg Ser Ser Gln Gly Thr Leu Val Thr Val Ser Ser Ala
                245                 250

<210> SEQ ID NO 79
<211> LENGTH: 254
<212> TYPE: PRT
<213> ORGANISM: Artificial Sequence
<220> FEATURE:
<223> OTHER INFORMATION: anti-CD40L construct

<400> SEQUENCE: 79

Asp Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Pro Leu Asn Tyr
            20                  25                  30

His Met Ala Trp Phe Arg Gln Ala Pro Gly Lys Glu Arg Glu Phe Val
        35                  40                  45

Ala Ala Ile Ser Ser Leu Leu Gly Ser Thr Asp Tyr Ala Asp Ser Val
    50                  55                  60

Lys Gly Arg Phe Thr Ile Ser Arg Asp Asn Ser Lys Thr Thr Leu Tyr
65                  70                  75                  80

Leu Gln Met Asn Ser Leu Arg Pro Glu Asp Thr Ala Val Tyr Tyr Cys
                85                  90                  95

Ala Ala Arg Glu Thr Thr His Ile Ser Thr Ser Asp Arg Val Asn Glu
            100                 105                 110

Ile Arg Asn Tyr Asp Tyr Trp Gly Gln Gly Thr Leu Val Thr Val Ser
        115                 120                 125

Ser Gly Gly Gly Gly Ser Gly Gly Gly Ser Glu Val Gln Leu Val Glu
    130                 135                 140

Ser Gly Gly Gly Val Val Gln Pro Gly Gly Ser Leu Arg Leu Ser Cys
145                 150                 155                 160

Ala Ala Ser Gly Phe Thr Phe Arg Ser Phe Gly Met Ser Trp Val Arg
                165                 170                 175

Gln Ala Pro Gly Lys Gly Pro Glu Trp Val Ser Ser Ile Ser Gly Ser
            180                 185                 190

Gly Ser Asp Thr Leu Tyr Ala Asp Ser Val Lys Gly Arg Phe Thr Ile
        195                 200                 205

Ser Arg Asp Asn Ser Lys Asn Thr Leu Tyr Leu Gln Met Asn Ser Leu
    210                 215                 220

Arg Pro Glu Asp Thr Ala Thr Tyr Tyr Cys Thr Ile Gly Gly Ser Leu
225                 230                 235                 240

Ser Arg Ser Ser Gln Gly Thr Leu Val Thr Val Ser Ser Ala
                245                 250

<210> SEQ ID NO 80
<211> LENGTH: 264
<212> TYPE: PRT
<213> ORGANISM: Artificial Sequence
<220> FEATURE:
<223> OTHER INFORMATION: anti-CD40L construct

<400> SEQUENCE: 80

Asp Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Glu Tyr Tyr
            20                  25                  30
```

Ala Ile Gly Trp Phe Arg Gln Ala Pro Gly Lys Glu Arg Glu Gly Val
                35                  40                  45

Ser Cys Ile Ser Ser Glu Gly Ser Thr Ser Tyr Ala Asp Ser Val Lys
 50                  55                  60

Gly Arg Phe Thr Ile Ser Arg Asp Asn Ser Lys Asn Thr Val Tyr Leu
 65                  70                  75                  80

Gln Met Asn Ser Leu Arg Pro Glu Asp Thr Ala Val Tyr Tyr Cys Ala
                 85                  90                  95

Thr Asp Pro Asp Arg Gly Phe Leu Gly Ser Ser Cys Asp Thr Gln Ser
                100                 105                 110

His Gln Tyr Asp Phe Trp Gly Gln Gly Thr Leu Val Thr Val Ser Ser
                115                 120                 125

Gly Gly Gly Gly Ser Gly Gly Gly Ser Gly Gly Gly Gly Ser Gly
                130                 135                 140

Gly Gly Gly Ser Glu Val Gln Leu Val Glu Ser Gly Gly Gly Val Val
145                 150                 155                 160

Gln Pro Gly Asn Ser Leu Arg Leu Ser Cys Ala Ala Ser Gly Phe Thr
                165                 170                 175

Phe Ser Ser Phe Gly Met Ser Trp Val Arg Gln Ala Pro Gly Lys Gly
                180                 185                 190

Leu Glu Trp Val Ser Ser Ile Ser Gly Ser Gly Ser Asp Thr Leu Tyr
                195                 200                 205

Ala Asp Ser Val Lys Gly Arg Phe Thr Ile Ser Arg Asp Asn Ala Lys
                210                 215                 220

Thr Thr Leu Tyr Leu Gln Met Asn Ser Leu Arg Pro Glu Asp Thr Ala
225                 230                 235                 240

Thr Tyr Tyr Cys Thr Ile Gly Gly Ser Leu Ser Arg Ser Ser Gln Gly
                245                 250                 255

Thr Leu Val Thr Val Ser Ser Ala
                260

<210> SEQ ID NO 81
<211> LENGTH: 264
<212> TYPE: PRT
<213> ORGANISM: Artificial Sequence
<220> FEATURE:
<223> OTHER INFORMATION: anti-CD40L construct

<400> SEQUENCE: 81

Asp Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Leu Glu Tyr Tyr
                 20                  25                  30

Ala Ile Gly Trp Phe Arg Gln Ala Pro Gly Lys Glu Arg Glu Gly Val
                 35                  40                  45

Ser Cys Ile Ser Ser Glu Gly Ser Thr Ser Tyr Ala Asp Ser Val Lys
 50                  55                  60

Gly Arg Phe Thr Ile Ser Arg Asp Asn Ser Lys Asn Thr Val Tyr Leu
 65                  70                  75                  80

Gln Met Asn Ser Leu Arg Pro Glu Asp Thr Ala Val Tyr Tyr Cys Ala
                 85                  90                  95

Thr Asp Pro Asp Arg Gly Phe Leu Gly Ser Ser Cys Asp Thr Gln Ser
                100                 105                 110

His Gln Tyr Asp Phe Trp Gly Gln Gly Thr Leu Val Thr Val Ser Ser
                115                 120                 125

-continued

Gly Gly Gly Gly Ser Gly Gly Gly Ser Gly Gly Gly Ser Gly
    130                 135                 140

Gly Gly Gly Ser Glu Val Gln Leu Val Glu Ser Gly Gly Val Val
145                 150                 155                 160

Gln Pro Gly Gly Ser Leu Arg Leu Ser Cys Ala Ala Ser Gly Phe Thr
                    165                 170                 175

Phe Arg Ser Phe Gly Met Ser Trp Val Arg Gln Ala Pro Gly Lys Gly
                180                 185                 190

Pro Glu Trp Val Ser Ser Ile Ser Gly Ser Gly Ser Asp Thr Leu Tyr
                195                 200                 205

Ala Asp Ser Val Lys Gly Arg Phe Thr Ile Ser Arg Asp Asn Ser Lys
210                 215                 220

Asn Thr Leu Tyr Leu Gln Met Asn Ser Leu Arg Pro Glu Asp Thr Ala
225                 230                 235                 240

Thr Tyr Tyr Cys Thr Ile Gly Gly Ser Leu Ser Arg Ser Ser Gln Gly
                    245                 250                 255

Thr Leu Val Thr Val Ser Ser Ala
            260

<210> SEQ ID NO 82
<211> LENGTH: 264
<212> TYPE: PRT
<213> ORGANISM: Artificial Sequence
<220> FEATURE:
<223> OTHER INFORMATION: anti-CD40L construct

<400> SEQUENCE: 82

Asp Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Glu Tyr Tyr
            20                  25                  30

Ala Ile Gly Trp Phe Arg Gln Ala Pro Gly Lys Glu Arg Glu Gly Val
        35                  40                  45

Ser Cys Ile Ser Ser Glu Gly Ser Thr Ser Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Val Tyr Tyr Cys Ala
                85                  90                  95

Thr Asp Pro Asp Arg Gly Phe Leu Gly Ser Ser Cys Asp Thr Gln Ser
            100                 105                 110

His Gln Tyr Asp Phe Trp Gly Gln Gly Thr Leu Val Thr Val Ser Ser
        115                 120                 125

Gly Gly Gly Gly Ser Gly Gly Gly Ser Gly Gly Gly Ser Gly
    130                 135                 140

Gly Gly Ser Glu Val Gln Leu Val Glu Ser Gly Gly Gly Leu Val
145                 150                 155                 160

Gln Pro Gly Asn Ser Leu Arg Leu Ser Cys Ala Ala Ser Gly Phe Thr
                    165                 170                 175

Phe Ser Ser Phe Gly Met Ser Trp Val Arg Gln Ala Pro Gly Lys Gly
                180                 185                 190

Leu Glu Trp Val Ser Ser Ile Ser Gly Ser Gly Ser Asp Thr Leu Tyr
                195                 200                 205

Ala Asp Ser Val Lys Gly Arg Phe Thr Ile Ser Arg Asp Asn Ala Lys
210                 215                 220

-continued

```
Thr Thr Leu Tyr Leu Gln Met Asn Ser Leu Arg Pro Glu Asp Thr Ala
225                 230                 235                 240

Val Tyr Tyr Cys Thr Ile Gly Gly Ser Leu Ser Arg Ser Ser Gln Gly
                245                 250                 255

Thr Leu Val Thr Val Lys Ser Ala
            260
```

The invention claimed is:

1. A polypeptide comprising at least one immunoglobulin single variable domain (ISVD) that binds CD40L, wherein said ISVD essentially consists of 4 framework regions (FR1 to FR4, respectively) and 3 complementarity determining regions (CDR1 to CDR3 respectively), in which:
   (i) CDR1 is selected from the group consisting of SEQ ID NO: 33 and amino acid sequences that have 1, 2 or 3 amino acid difference(s) with SEQ ID NO: 33; CDR2 is selected from the group consisting of SEQ ID NO: 35 and amino acid sequences that have 1, 2 or 3 amino acid difference(s) with SEQ ID NO: 35; and CDR3 is selected from the group consisting of SEQ ID NO: 37 and amino acid sequences that have 1, 2, 3 or 4 amino acid difference(s) with SEQ ID NO: 37; or
   (ii) CDR1 is selected from the group consisting of SEQ ID NO: 61 and amino acid sequences that have 1, 2 or 3 amino acid difference(s) with SEQ ID NO: 61; CDR2 is selected from the group consisting of SEQ ID NO: 63 and amino acid sequences that have 1, 2 or 3 amino acid difference(s) with SEQ ID NO: 63; and CDR3 is selected from the group consisting of SEQ ID NO: 65 and amino acid sequences that have 1, 2, 3 or 4 amino acid difference(s) with SEQ ID NO: 65; or
   (iii) CDR1 is selected from the group consisting of SEQ ID NO: 40 and amino acid sequences that have 1, 2 or 3 amino acid difference(s) with SEQ ID NO: 40; CDR2 is selected from the group consisting of SEQ ID NO: 42 and amino acid sequences that have 1, 2 or 3 amino acid difference(s) with SEQ ID NO: 42; and CDR3 is selected from the group consisting of SEQ ID NO: 44 and amino acid sequences that have 1, 2, 3 or 4 amino acid difference(s) with SEQ ID NO: 44; or
   (iv) CDR1 is selected from the group consisting of SEQ ID NO: 68 and amino acid sequences that have 1, 2 or 3 amino acid difference(s) with SEQ ID NO: 68; CDR2 is selected from the group consisting of SEQ ID NO: 70 and amino acid sequences that have 1, 2 or 3 amino acid difference(s) with SEQ ID NO: 70; and CDR3 is selected from the group consisting of SEQ ID NO: 72 and amino acid sequences that have 1, 2, 3 or 4 amino acid difference(s) with SEQ ID NO: 72.

2. The polypeptide according to claim 1, in which CDR1 is chosen selected from the group consisting of
   (a) SEQ ID NO: 61; and
   (b) amino acid sequences that have 1, 2 or 3 amino acid difference(s) with SEQ ID NO: 61, wherein
      at position 1 the G has been changed into E or R;
      at position 2 the R has been changed into H or G;
      at position 3 the T has been changed into I, A, S or P;
      at position 4 the P has been changed into S;
      at position 5 the L has been changed into P;
      at position 6 the N has been changed into S, D or I;
      at position 7 the Y has been changed into H;
      at position 8 the H has been changed into N;
      at position 9 the M has been changed into K, T or V; and/or
      at position 10 the A has been changed into G, S or T;
   and in which CDR2 is selected from the group consisting of
   (a) SEQ ID NO: 63; and
   (b) amino acid sequences that have 1, 2 or 3 amino acid difference(s) with SEQ ID NO: 63, wherein
      at position 1 the A has been changed into G;
      at position 2 the I has been changed into V;
      at position 4 the S has been changed into N, R or G;
      at position 6 the L has been changed into I;
      at position 7 the G has been changed into S or D;
      at position 8 the S has been changed into G, I or F; and/or
      at position 9 the T has been changed into P or S;
   and in which CDR3 is selected from the group consisting of
   (a) SEQ ID NO: 65; and
   (b) amino acid sequences that have 1, 2, 3 or 4 amino acid difference(s) with SEQ ID NO: 65, wherein
      at position 1 the R has been changed into Q or L;
      at position 2 the E has been changed into D or K;
      at position 3 the T has been changed into S, M, A or K;
      at position 4 the T has been changed into I, S, A or R;
      at position 5 the H has been changed into Y or N;
      at position 6 the Y has been changed into I, H or N;
      at position 7 the S has been changed into T, G, N or I;
      at position 8 the T has been changed into I or A;
      at position 9 the S has been changed into N or R;
      at position 10 the D has been changed into A;
      at position 11 the R has been changed into S or G;
      at position 13 the N has been changed into D, Y or S;
      at position 14 the E has been changed into V, A, D or N;
      at position 15 the M has been changed into I, V, K or T;
      at position 16 the R has been changed into K, S, W, M, G or T;
      at position 17 the H has been changed into N, L, Q, R or D;
      at position 19 the D has been changed into N; and/or
      at position 20 the Y has been changed into H, F or N.

3. The polypeptide according to claim 1, in which:
   CDR1 is SEQ ID NO: 33, CDR2 is SEQ ID NO: 35 and CDR3 is SEQ ID NO: 37; or
   CDR1 is SEQ ID NO: 61, CDR2 is SEQ ID NO: 63 and CDR3 is SEQ ID NO: 65.

4. The polypeptide according to claim 1, in which said ISVD is SEQ ID NO: 8 or SEQ ID NO: 6.

5. The polypeptide according to claim 1, in which CDR1 is selected from the group consisting of
   (a) SEQ ID NO: 40; and
   (b) amino acid sequences that have 1, 2 or 3 amino acid difference(s) with SEQ ID NO: 40, wherein
      at position 3 the T has been changed into S, N, A or I;
      at position 4 the L has been changed into Q, S, M or G;
      at position 8 the A has been changed into N or V;
      at position 9 the I has been changed into L or V; and/or
      at position 10 the G has been changed into A; and in which CDR2 is selected from the group consisting of
(a) SEQ ID NO: 42; and
(b) amino acid sequences that have 1, 2 or 3 amino acid difference(s) with SEQ ID NO: 42, wherein
at position 2 the I has been changed into V;
at position 3 the S has been changed into G;
at position 5 the E has been changed into G;
at position 6 the G has been changed into S;
at position 7 the S has been changed into G, N, T or I;
at position 8 the T has been changed into A, P, I or S; and/or
at position 9 the S has been changed into I, R or G; and
in which CDR3 is selected from the group consisting of
(a) SEQ ID NO: 44; and
(b) amino acid sequences that have 1, 2, 3 or 4 amino acid difference(s) with SEQ ID NO: 44, wherein
at position 4 the R has been changed into S;
at position 7 the L has been changed into F, M or W;
at position 8 the G has been changed into D, A or S;
at position 9 the S has been changed into G, N or R;
at position 10 the S has been changed into G, N, T or R;
at position 12 the D has been changed into G, N, E or V;
at position 13 the T has been changed into N or A;
at position 14 the Q has been changed into H, K, L or R;
at position 15 the S has been changed into P or T;
at position 16 the H has been changed into N or Y;
at position 17 the Q has been changed into L, R or H;
at position 18 the Y has been changed into F;
at position 19 the D has been changed into G; and/or
at position 20 the Y has been changed into F or N.

6. The polypeptide according to claim 1, in which:
CDR1 is SEQ ID NO: 40, CDR2 is SEQ ID NO: 42 and CDR3 is SEQ ID NO: 44; or
CDR1 is SEQ ID NO: 68, CDR2 is SEQ ID NO: 70, and CDR3 is SEQ ID NO: 72.

7. The polypeptide according to claim 1, wherein said polypeptide binds to CD40L:
with a $K_D$ between $1E^{-07}$ M and $1E^{-13}$ M, between $1E^{-08}$ M and $1E^{-12}$ M, at most $1E^{-07}$ M, lower than $1E^{-08}$ M or $1E^{-09}$ M, or lower than $1E^{-10}$ M, $5E^{-11}$ M, $4E^{-11}$ M, $2E^{-11}$ M, $1.7E^{-11}$ M, $1E^{-11}$, $5E^{-12}$ M, $4E^{-12}$ M, $3E^{-12}$ M, or $1E^{-12}$ M;
with an $IC_{50}$ between $1E^{-07}$ M and $1E^{-12}$ M, between $1E^{-08}$ M and $1E^{-11}$ M;
with an $IC_{50}$ of at most $1E^{-07}$ M, $1E^{-08}$ M, $1E^{-09}$ M, $5E^{-10}$ M, $4E^{-10}$ M, $3E^{-10}$ M, $2E^{-10}$ M, or $1E^{-10}$ M; and/or
with an off-rate of less than $5E^{-04}$ $(s^{-1})$.

8. The polypeptide according to claim 1, wherein said CD40L is human CD40L, optionally SEQ ID NO: 1.

9. The polypeptide according to claim 1, wherein binding of the ISVD to CD40L modulates an activity of CD40L, wherein said modulation of an activity is
antagonizing an activity of CD40L;
blocking the binding of CD40L to CD40 of at least 20%, 30%, 40%, 50%, 60%, 70%, 80%, 90%, or 95%;
antagonizing CD40 mediated induction of T-cell costimulatory molecules and/or immunostimulatory molecules;
inhibiting B-cell activation;
not substantially inducing JNK phosphorylation in Jurkat T cells;
not substantially inducing IFNγ secretion by Jurkat T cells co-stimulated with anti-CD3 antibody;
not substantially inducing activation of primary endothelial cells; and/or
not substantially inducing platelet activation or platelet aggregation.

10. The polypeptide according to claim 1, wherein the polypeptide further comprises an ISVD that binds serum albumin, wherein said ISVD essentially consists of 4 framework regions (FR1 to FR4, respectively) and 3 complementarity determining regions (CDR1 to CDR3 respectively), in which CDR1 is SEQ ID NO: 74, CDR2 is SEQ ID NO: 75, and CDR3 is SEQ ID NO: 76; optionally wherein said ISVD binding serum albumin is selected from the group consisting of ALB8 (SEQ ID NO: 11) and ALB23 (SEQ ID NO: 12).

11. A method of inhibiting binding of CD40L to CD40 in an individual, the method comprising administering the polypeptide according to claim 1 to said individual.

12. The method according to claim 11, wherein the subject has a disease or disorder is selected from the group consisting of an autoimmune disease, Systemic Lupus Erythematosus (SLE), Lupus Nephritis, Immune Thrombocytopenic Purpura (ITP), transplant rejection, Crohn's Disease, Sjögren's Syndrome, Inflammatory Bowel Disease (IBD), colitis, asthma/allergy, atherosclerosis, Myasthenia Gravis, Multiple Sclerosis, Psoriasis, Rheumatoid Arthritis, Ankylosing Spondylitis, Coronary Heart Disease, Type 1 Diabetes, amyotrophic lateral sclerosis (ALS) and immune response to recombinant drug products.

13. The polypeptide according to claim 1, in which in which said ISVD is SEQ ID NO: 7 or SEQ ID NO: 3.

* * * * *

UNITED STATES PATENT AND TRADEMARK OFFICE
CERTIFICATE OF CORRECTION

| | | |
|---|---|---|
| PATENT NO. | : 11,248,055 B2 | Page 1 of 1 |
| APPLICATION NO. | : 15/778677 | |
| DATED | : February 15, 2022 | |
| INVENTOR(S) | : Pattyn et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 672 days.

Signed and Sealed this
Eleventh Day of February, 2025

Coke Morgan Stewart
*Acting Director of the United States Patent and Trademark Office*